(12) United States Patent
Simmons

(10) Patent No.: US 7,918,808 B2
(45) Date of Patent: Apr. 5, 2011

(54) ASSISTIVE CLOTHING

(76) Inventor: John C. Simmons, Germantown, TN (US)

(*) Notice: Subject to any disclaimer, the term of this patent is extended or adjusted under 35 U.S.C. 154(b) by 2461 days.

(21) Appl. No.: 10/202,414

(22) Filed: Jul. 22, 2002

(65) Prior Publication Data
US 2003/0120183 A1 Jun. 26, 2003

Related U.S. Application Data

(63) Continuation-in-part of application No. 09/960,293, filed on Sep. 20, 2001, now Pat. No. 6,805,677.

(60) Provisional application No. 60/234,191, filed on Sep. 20, 2000.

(51) Int. Cl.
A61B 5/103 (2006.01)
A61B 5/117 (2006.01)
G09B 21/00 (2006.01)

(52) U.S. Cl. .................. 600/590; 345/156; 340/825.19

(58) Field of Classification Search .......... 600/587–595; 178/18.01; 340/825.19; 341/21; 715/865
See application file for complete search history.

(56) References Cited

U.S. PATENT DOCUMENTS

| 4,983,786 | A | * | 1/1991 | Stevens et al. | ............. 178/18.01 |
| 5,583,303 | A | * | 12/1996 | Franz | ....................... 73/862.046 |
| 6,222,524 | B1 | * | 4/2001 | Salem et al. | .................. 345/157 |
| 6,598,006 | B1 | * | 7/2003 | Honda et al. | .................. 702/116 |

* cited by examiner

Primary Examiner — Max Hindenburg
Assistant Examiner — Jonathan M Foreman

(57) ABSTRACT

An apparatus and process for empowering those in wheelchairs and others with loss of limb control to walk, climb stairs, sit in ordinary chairs, use normal bathroom facilities and stand at normal height with their peers. It also provides a means to speed rehabilitation of the injured and a means to deliver more comfortable and effective prostheses while providing superior physical therapy without draining professional resources which includes new simulation and training means. Most of the apparatus is worn under normal clothing allowing them to enjoy a normal appearance. Additional advancements include improved actuator design, user interface, visual means and advanced responsive virtual reality.

38 Claims, 21 Drawing Sheets

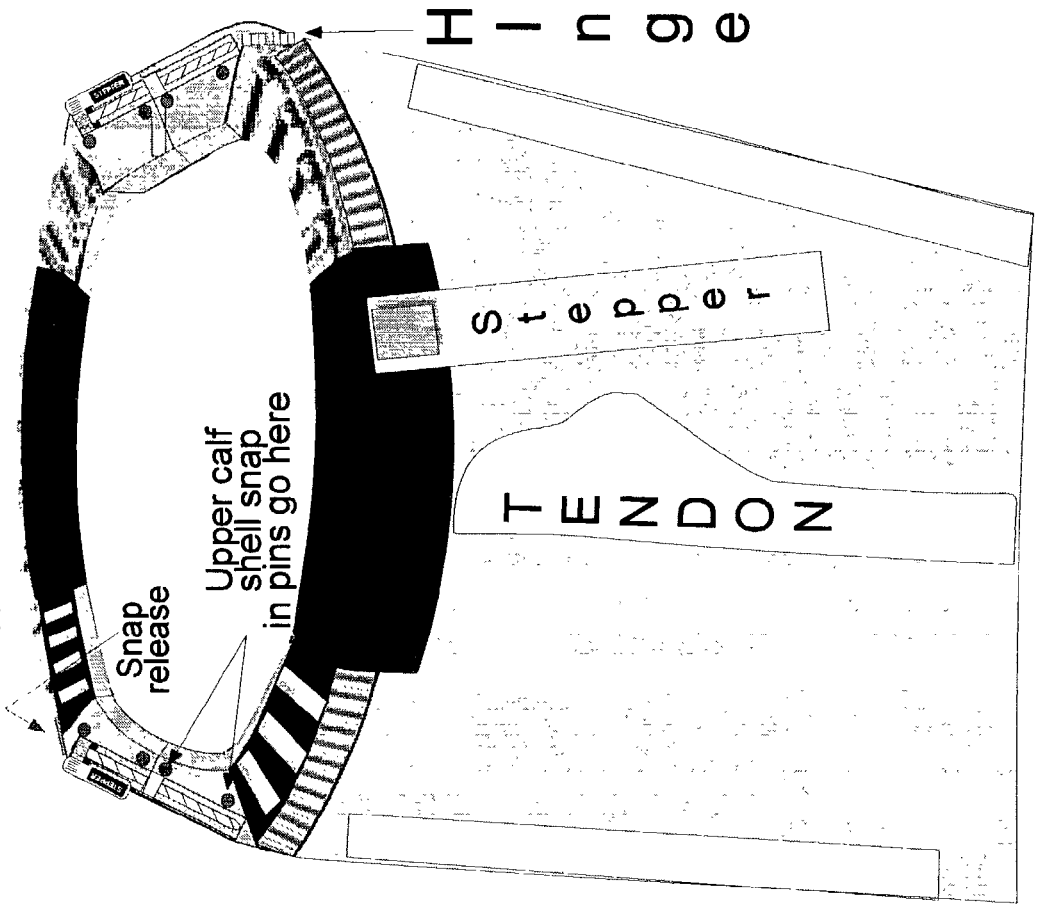
Fig. 4
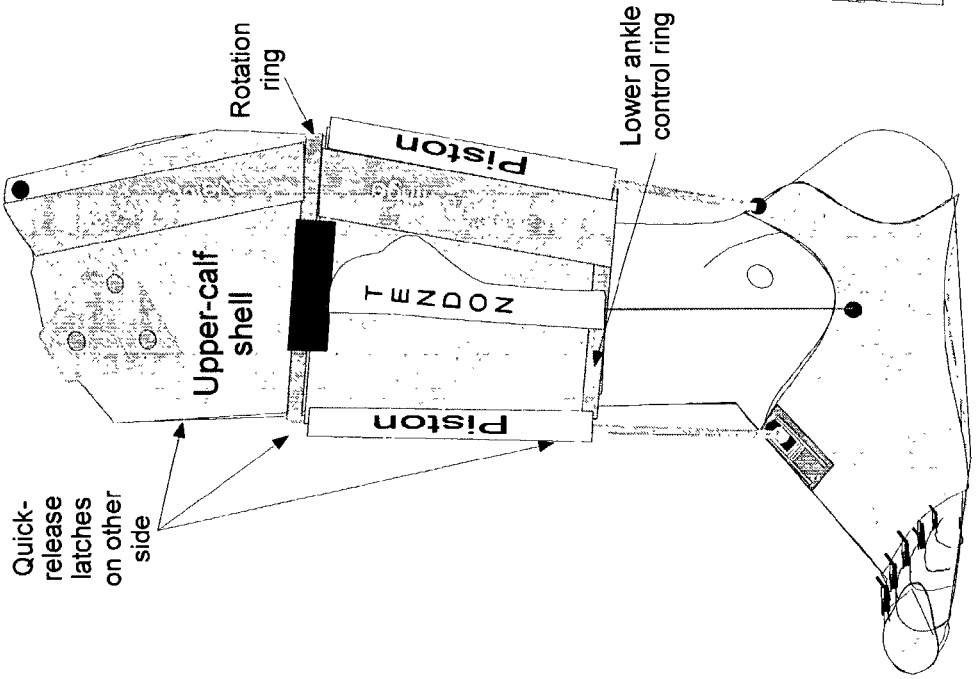

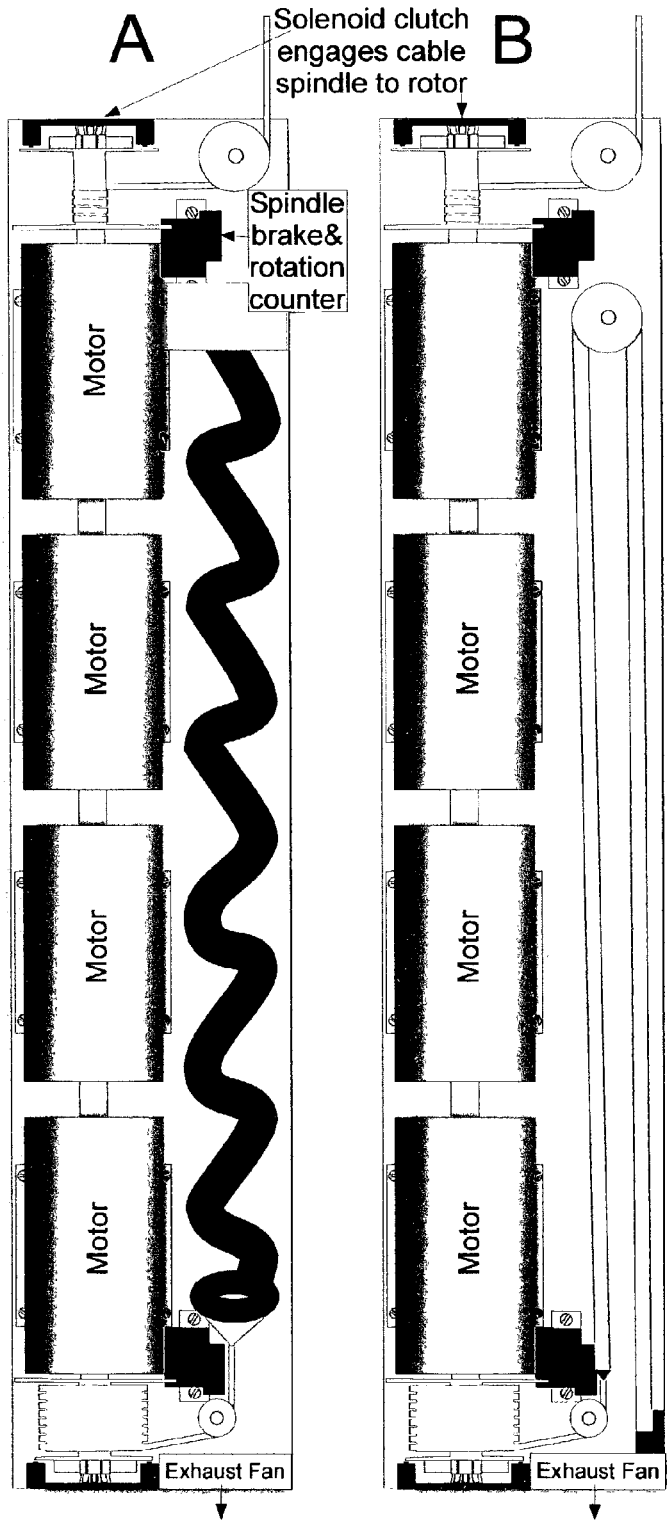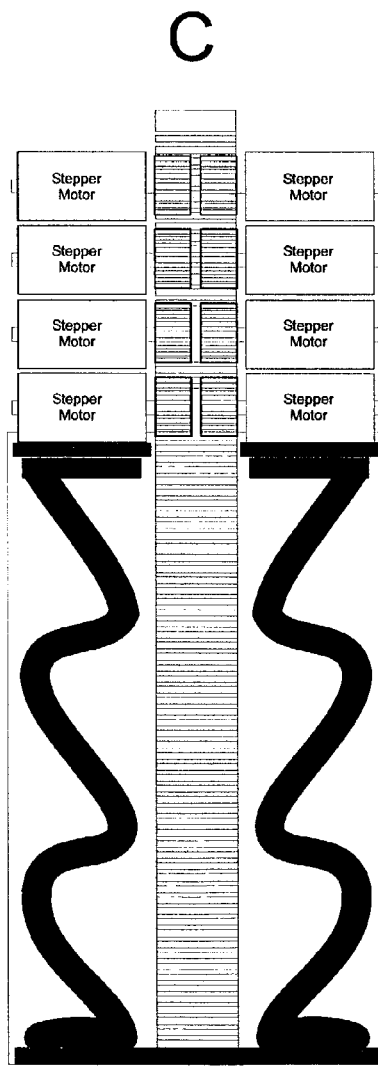
Fig. 6
Extra-Flat Strong-Side Biased, automatically adjustable & configurable actuator Arrays

Figure 12
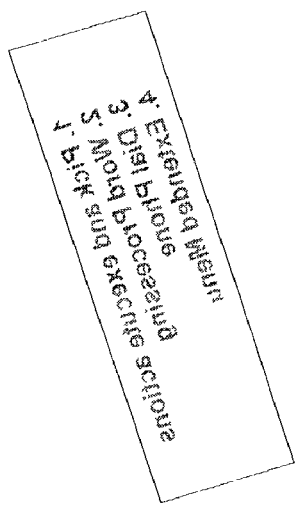
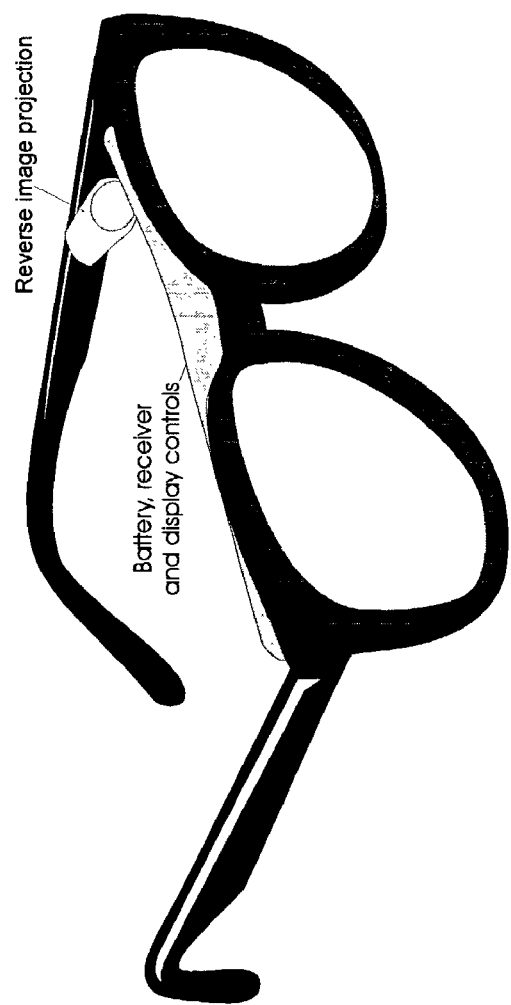

Fig. 15
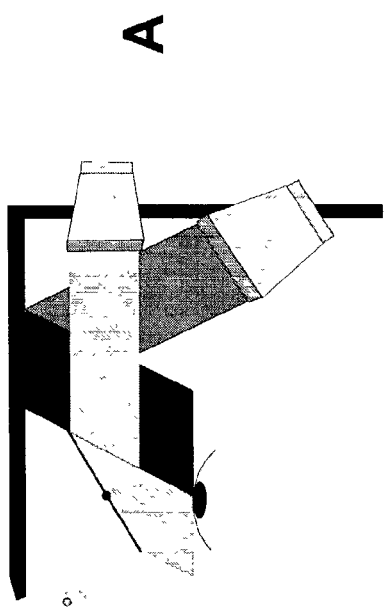
A
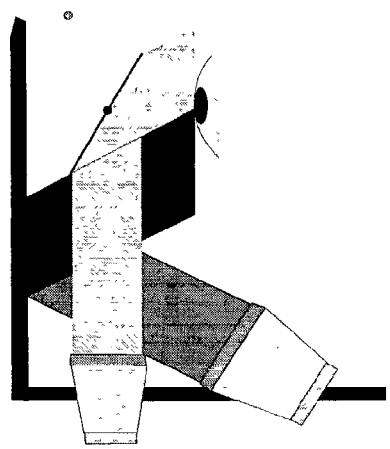
APPARENT IMAGE
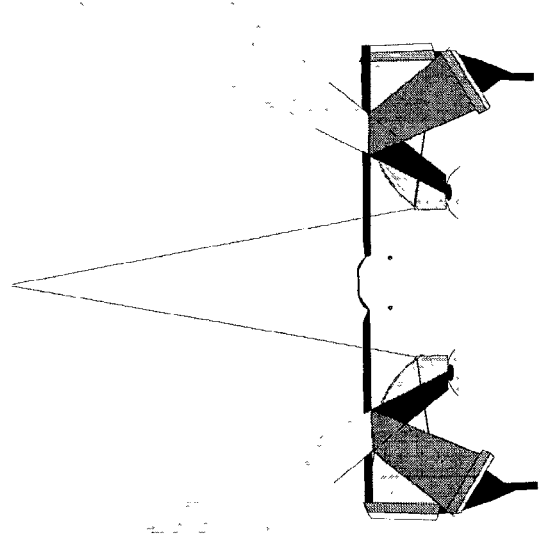
B

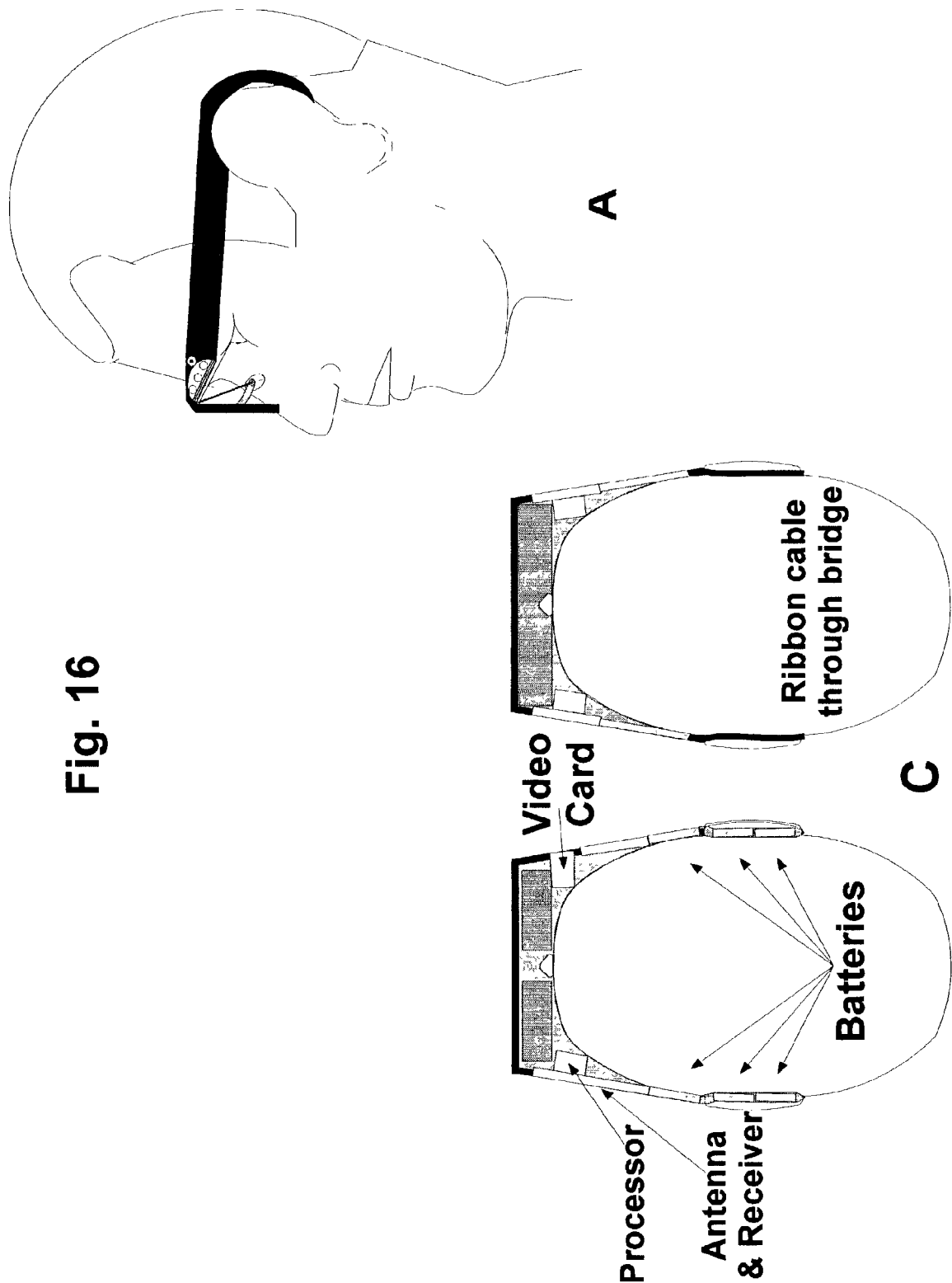

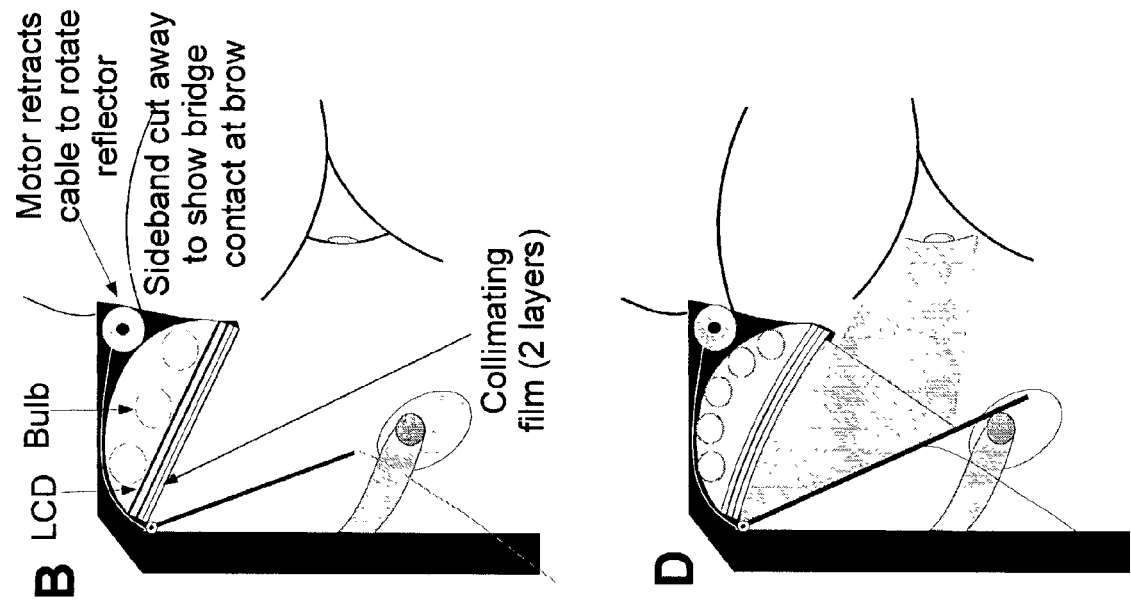

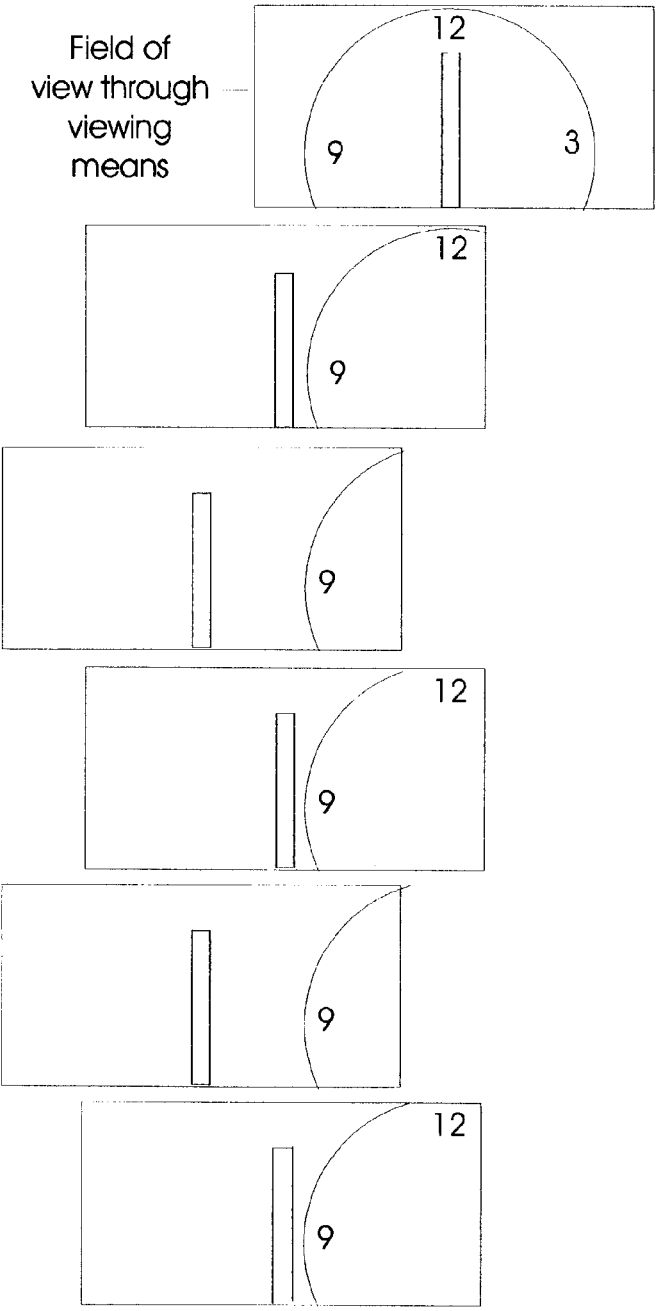

Field of view through viewing means

Initially all things point forward. There is a light line below the dark line that can't be seen yet. The dark line stays in the middle of the screen indicating the user's current desired yaw.
Note the clock viewed through the glasses that never moves.

Then the user points his head to the left. The dark line (where he wants to go) stays in the middle. The light line moves out to his actual yaw which hasn't had time to change. The light vertical bar continues to be to the right or left of the dark bar in the amount (relative degrees) of the difference between the yaw of the head and the direction of the body. Other calculation means can be used to home in on positions, but this is used as an example.

As directed by the software, the next footstep or adjustment within the current footstep moves the body (with head on it) to turning ½ the degrees of the head's turn above (just an example amount). The yellow line accurately indicates current actual yaw (it was the body that turned).

At this point, before the next step, the user continues to "home in" on his desired target-- this time moving his head to the right till the blue line is over his intended destination.

Note that the light bar doesn't move in the display view because, in this example, the body direction didn't change Since the 2 bars are still out of sync, In the next step, the software directs the body to correct another ½ the distance (just an example amount).

Fig. 18

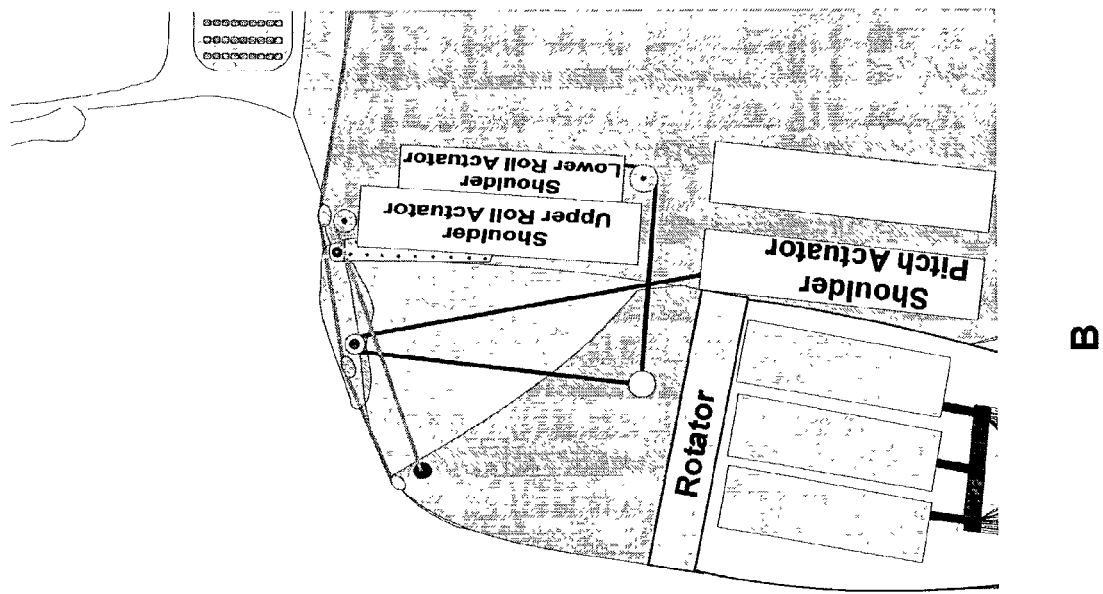
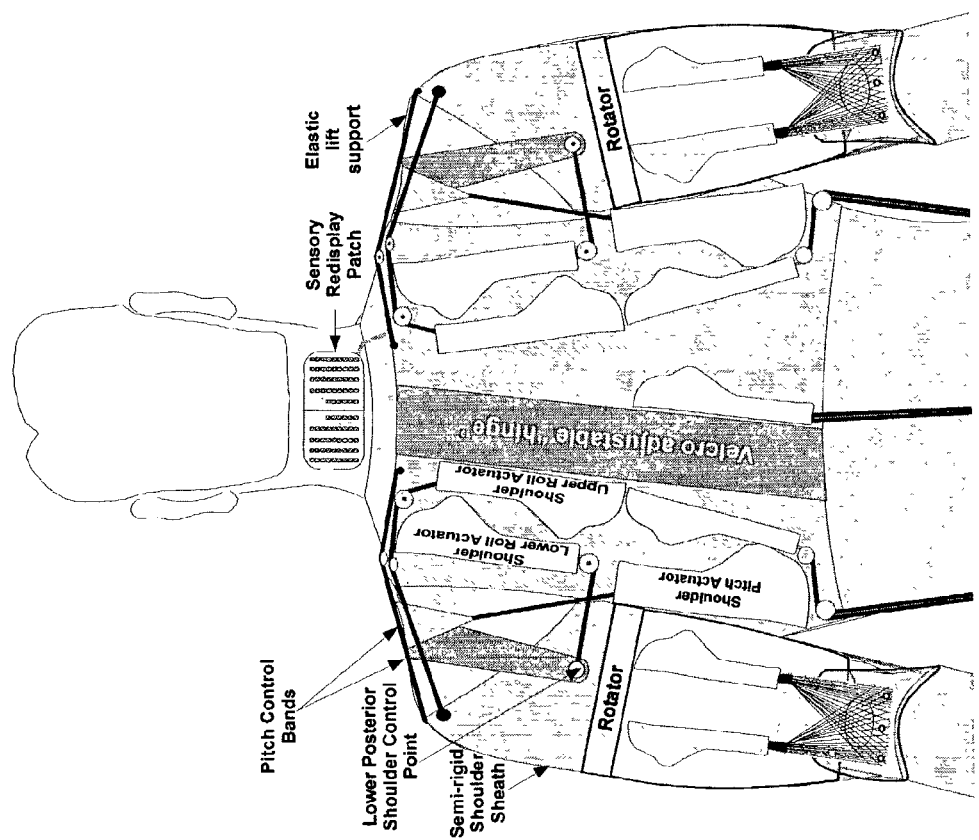
Fig. 19

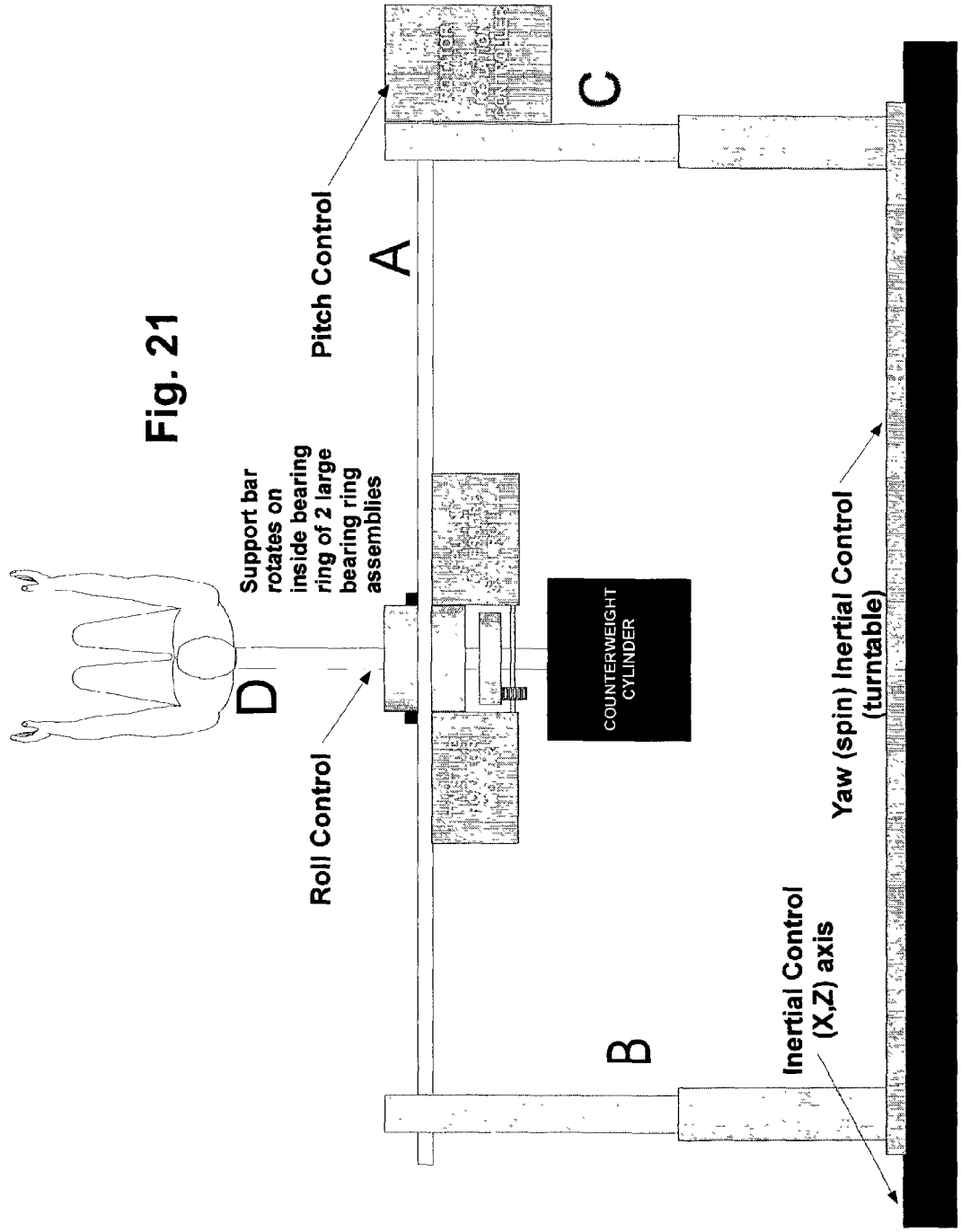

ASSISTIVE CLOTHING

The present application is a Continuation-in-Part of U.S. utility patent application Ser. No. 09/960,293 titled "Wheelless Walking Support and Rehabilitation Device" which application was filed Sep. 20, 2001 now U.S. Pat. No. 6,805,677 and which claims the benefit of provisional application 60/234,191 which was filed on Sep. 20, 2000.

BACKGROUND OF THE INVENTION

It should be noted on the front end that taking a person who is currently confined to a wheelchair and must blow or suck into a straw to gain even limited mobility and allowing them to stand up and walk normally at eye level with their peers, care for their own personal needs and function independently with comfortable and inexpensive prosthetics that are concealed by normal clothing is a daunting task. Attesting to just how difficult to impossible that task has been to this point are the facts that:

1. The current design of a wheelchair, except for the addition of power, is not much improved in functionally over the original invented by Eric Von Bulenheimer in 1672.
2. Perhaps the greatest advancement since then has been a chair on wheels that can climb stairs but must be navigated backwards, doesn't work on many staircases including but not limited to spiral staircases and short depth staircases, depends on the traction of its wheels even on slippery stairs for stability, requires some strength to manage the handrail and is still a heavy (202 pounds) wheelchair that must be accommodated (lugged) everywhere the user goes including airplanes, cars, escalators, bathrooms, etc.
3. In the United States alone we spend billions every year to accommodate just wheelchair supported handicaps.
4. Millions of people who want to work are not able to even care for themselves with that additional cost measured not only in human tragedy but in the loss of the productivity of good and willing minds.
5. This patent disclosure, in order to overcome the seeming endless spectrum of technical and human problems that have prevented the provision of a real solution, requires well over 100 pages just to recite on paper the uncommon number of new technologies and processes required to work together to effectively solve the inherent problems.

Thousands of people struggle with crutches and wheelchairs and uncomfortable prosthetics all their life. There are new wheel-based chair solutions that include balancing features but stairs, which have always been impossible, though climbable while balanced on wheels, can be very dangerous if the user is bumped or encounters a slippery or faulty surface and it's neither a smooth ride or an impressive entrance. Also, some paraplegics can only crudely control a powered wheelchair by awkwardly blowing into a straw and then only under almost ideal, smooth terrain circumstances and within a very limited scope of activities. For many, hands and feet, etc. are useless making them helpless dependents on others.

Many forms of prostheses have been attempted to aid in the direction of assistive equipment and for full replacement of lost limbs (both walking related and others) with some success. However rejection rates are high due to difficulty of use, long training periods, expense of professional support, burdens on parents, overhead of maintenance, lack of delicacy due to the absence of tactile response, tight prostheses, uncomfortable fits, raw friction areas on the patient's skin, itching, hot spots and poor circulation. Many can't afford a good prosthesis because the concept of standard parts with its incumbent economies of scale and ability to serve a broad market has not completely reached the prosthetics world due to the lack of success in developing a "one size fits many" prosthesis. It is normative for even minor prosthetics to be custom designed and custom fitted and then must be adjusted over time particularly in children.

Further, research and development has been limited by inadequate simulation and modeling facilities that require tedious setup unique to each test patient as well as inefficient and awkward means to communicate complex human motions to a virtual body and to communicate/recreate virtual body motions in a human body.

The current invention overcomes all of these shortcomings.

SUMMARY OF THE INVENTION

The assistive clothing apparatus and process is designed to provide independence, freedom of mobility and a new approach to prostheses that allows more functional replacement of limbs, nerve-damage rehabilitation, the addition of sensory means to replace those lost and to provide an improved means for more rapid support of research, development and training in the areas of rehabilitation as well as any other areas benefiting from simulation supported modeling, training and research.

Therefore, it is an object of the current invention to provide an apparatus and process for rapidly capturing data reflective of, potentially, an entire body's positions and precise vectors of motion (of every limb or selected groups of limbs) along with timing, attitude and load/pressure data in an easily stored, concise format that is easily applied to recreating those precise attitudes and actions on a living or mechanical body in an accurate and fluid manner.

It is also an object of the current invention to provide an effective means to accurately and fluidly place and firmly but flexibly support any number of body limbs in a precise position with said means functioning comfortably, where appropriate, under normal clothing.

It is also an object of the current invention to use this captured information and precision body control apparatus to provide a means to recreate both a previously modeled activity or an active user session in a virtual environment. There, virtual bodies with effectively congruent joint and musculature to the human user's can be guided by either stored, historical user body actions or live user motions that are then recreated in the virtual environment where results can be tested and/or the user can feel and experience the virtual environment through the assistive clothing for training, product testing, etc.

It is also an object of the current invention to apply the above described means along with programmatically driven controls to allow disabled users in wheelchairs to walk, climb stairs, use normal bathroom facilities and stand at eye level with their peers to overcome their disability and simultaneously use and regularly place the burden of their weight on their own joints and bones to prevent bone degeneration.

In addition to the humiliation that can be caused by the uncontrolled flailing associated with spasms in an already fragile patient, substantial damage is caused by snapping against restraints (tie-downs), hitting nearby objects and spasm induced falls out of a chair or while attempting to walk. It is an object of the current invention to control these spasms to the degree that they are actually less distractive to bystanders while preventing injuries to the patient and others as well as falls even when the patient is walking.

It is also an object of the current invention to extend the lifetime of powered prosthetics and the range of those used for personal mobility allowing user's to go greater distances with less power consumption.

It is also an object of the current invention to provide lightweight, inexpensive equipment using actuators that provide more power where needed with less weight and size.

It is also an object of the current invention to provide a superior form of prosthesis that has a lower rejection rate and allows longer periods of comfortable use due to ease of training, fast and simple mounting and removal, reduction in itching and hot-spots, elimination of tight-fitting prosthesis at rub points, self-ventilation and programmatically controlled muscle and capillary circulation support.

It is also an object of the current invention to prevent the degenerative effects of both hyper-rigid and asymmetrical gaits by enforcing appropriate gait and additionally providing rest at contact and friction points by cyclically varying the gait in a user or programmatically controlled but natural fashion.

It is also an object of the current invention to provide a prosthetic that does not require continual refitting (particularly in children) by the current invention's unique ability so self-resize and to do so programmatically.

It is also an object of the current invention to provide for the user a simpler and faster process for putting on prostheses which also shortens patient training time and minimizes professional oversight expenses.

It is also an object of the current invention to provide a more effective prosthetic that automatically aligns, positions and adjusts itself both while being put on and during the day as it is used so that the precision alignment doesn't degrade or change over time.

It is also an object of the current invention to provide an improved prosthesis platform that allows for replacement of multiple joint disarticulations in a single limb with functionality even in the joints in the $6^{th}$ level of extremity.

It is a further object of the current invention to provide a user equipment design that more closely resembles "standard parts" that can be mass produced rather than each element being painfully and expensively custom configured around each individual allowing the assistive clothing technology to be more rapidly and inexpensively brought to the many waiting for an escape from the confinements of a wheelchair.

It is also an object of the current invention to provide users who have inadequate or non-existent feeling in limbs a sense of touch allowing the user to more quickly adapt to new prostheses and providing a more useful and delicate control of them.

It is also an object of the current invention to provide a means to rapidly set up a simulated environment made up of standard virtual parts that can quickly be virtually assembled to precisely match the appearance and actions of real-world bodies and applications being simulated.

It is also an object of the current invention to provide an effective training device to teach complex or intricate procedures from batting to surgery in a manner that both actually moves the body in a perfect form and that can be set to resist motion outside the planned script or programmatic procedure.

BRIEF DESCRIPTION OF THE DRAWINGS

In FIG. 3A the ankle uses the aforementioned split-rotator process. It, like the waist version of FIG. 3B (which is enlarged at the bottom of 3B) is supportive of a closer, less bulky fit, automatic self-adjustment and ease of dressing. The waist assembly of 3B rotates on compact bearings with the vertical tendons firmly maintaining upper-torso position and, in coordination with the twin low-friction ribbons (shown here as a broad diagonal band from lower front of upper-torso to the back side of the rotator with slight and controlled elasticity across the front), with one such ribbon being on each side, the waist rotation stepper motors on both sides, move the upper-torso as directed by the processing means. In FIG. 3A, however, an embodiment is shown in which the entire waist assembly is reduced to a lighter, semi-rigid, internally friction intensive, waffle-vented broad-belt which is tendon directed from above the waist assembly to bend and rotate the upper torso.

FIG. 3A also illustrates on the right knee (cutaway view) an optional means for increasing, for example, step-climbing capacity without increasing the size of the actuators responsible for leg extension at the knee under full load thus removing the concentrated load from that single actuator assembly and allowing the opposing (flexion) actuator to help indirectly by carrying a consequently heavier load in the ensuing flexion cycle. This, along with several other actuator-power-enhancing elements of the current invention, allows more usable power from smaller actuators.

Actuators of different pedigrees may be interchangeable and even mixed and matched together in the same environment. Actuators shown above the knee in FIG. 3A are strong-side-biased electric motor actuators (such as those shown in FIG. 6) while actuators for the same functions are illustrated in FIG. 3B using hydraulic actuators (such as those seen in FIG. 11). An optional additional vertically strung abduction tendon (not shown) from the center of the waist assembly (where the sensors are shown) directly down to the thigh shell) provides additional leg abduction strength where needed. Also not shown is the optional single medial adduction tendon which attaches medially to the upper left leg and passes through an eyelet attached medially on the upper right leg on the way to the actuator so that, when retracted, the adduction force of the medial rotation and adduction crossed-tendon pair are reinforced.

Figure 3:
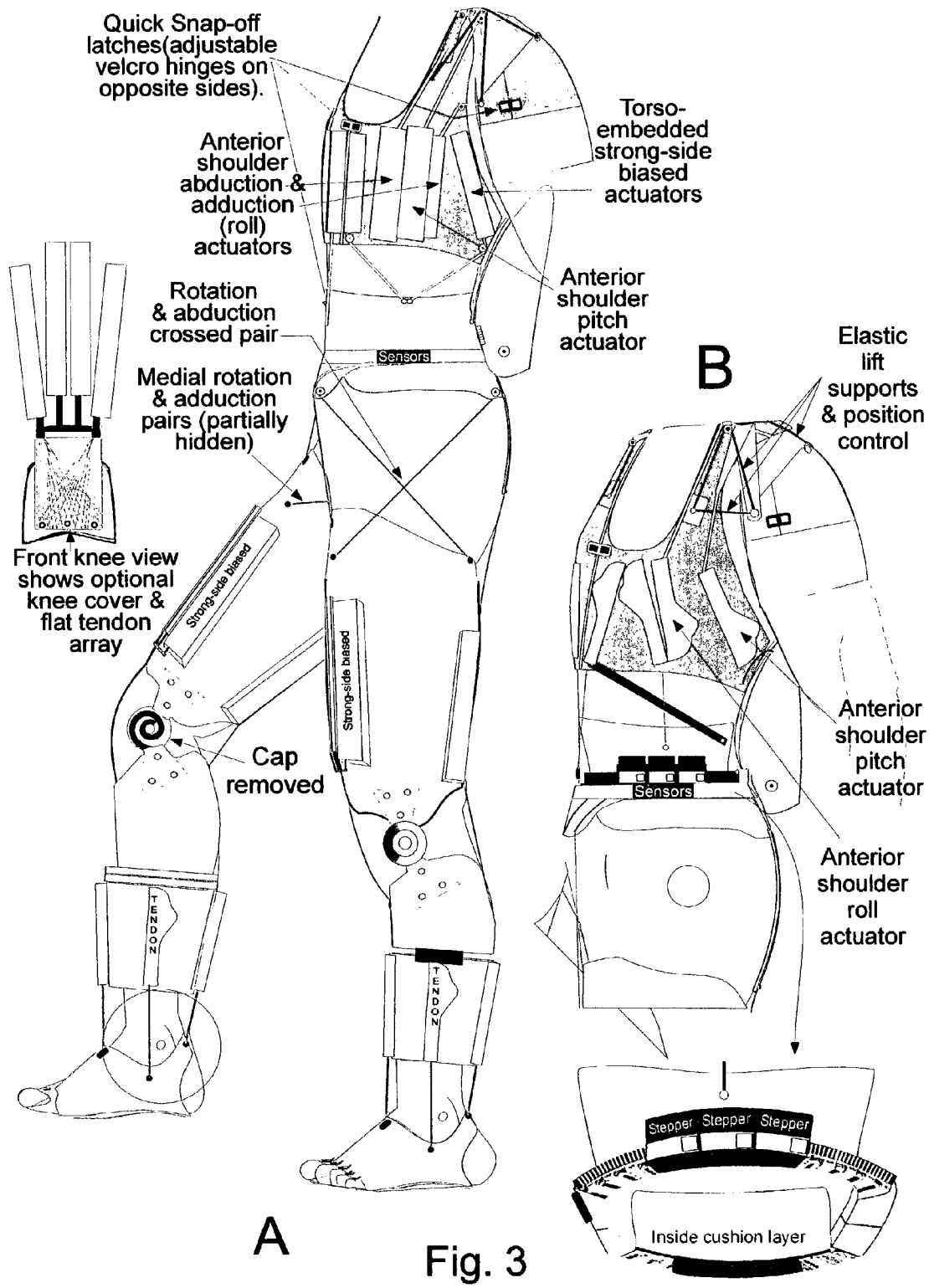
FIG. 3 illustrates a standing body wearing two of the applicable embodiments (FIG. 3A and FIG. 3B). Both embodiments include the same custom-adjustable, quick snap-off removal and assembly as well as expansion means to support automatic adjustment and circulation/comfort enhancing massage (better illustrated in a similar application in FIG. 5).

FIG. 4 illustrates the split-rotator option of FIG. 3 applied to the ankle and also illustrates the use of non-tendon based actuators to achieve the same joint manipulation results as other tendon based embodiments of the current invention. A side view enlargement of the upper part of the ankle rotator is shown to its right. As the stepper or servo motor turns its gear against the ankle housing's geared lip, the ankle housing below it, which is itself suspended here on roller bearings, is thus rotated which rotates the areas below. Although multiple synchronized motors (on each side) can be used to increase power, only one motor is shown here because that is all that is needed to move the free lower portion. Also illustrated are the three snap release latches indicated (but out of view) on the left of FIG. 4 and located at the left on FIG. 5. Also, opposite them, the opposing hinges, shown at left in FIG. 4, are simply Velcro side B taped over the already Velcro side A covered vertical sides of the thus joined prosthetic additionally providing easy adjustment for larger or smaller ankles. The upper-calf shell attaches to the rotator ring with snap-in male pins placed into the 8 slots shown for them in the rotator ring leaving enough vertical space at the sides for the bearing-riding strip's travel. To visualize the motion, note that the rotator ring and the upper-calf shell do not move but the lower portion of the ankle assembly moves under (supported by) it.

Figure 5:
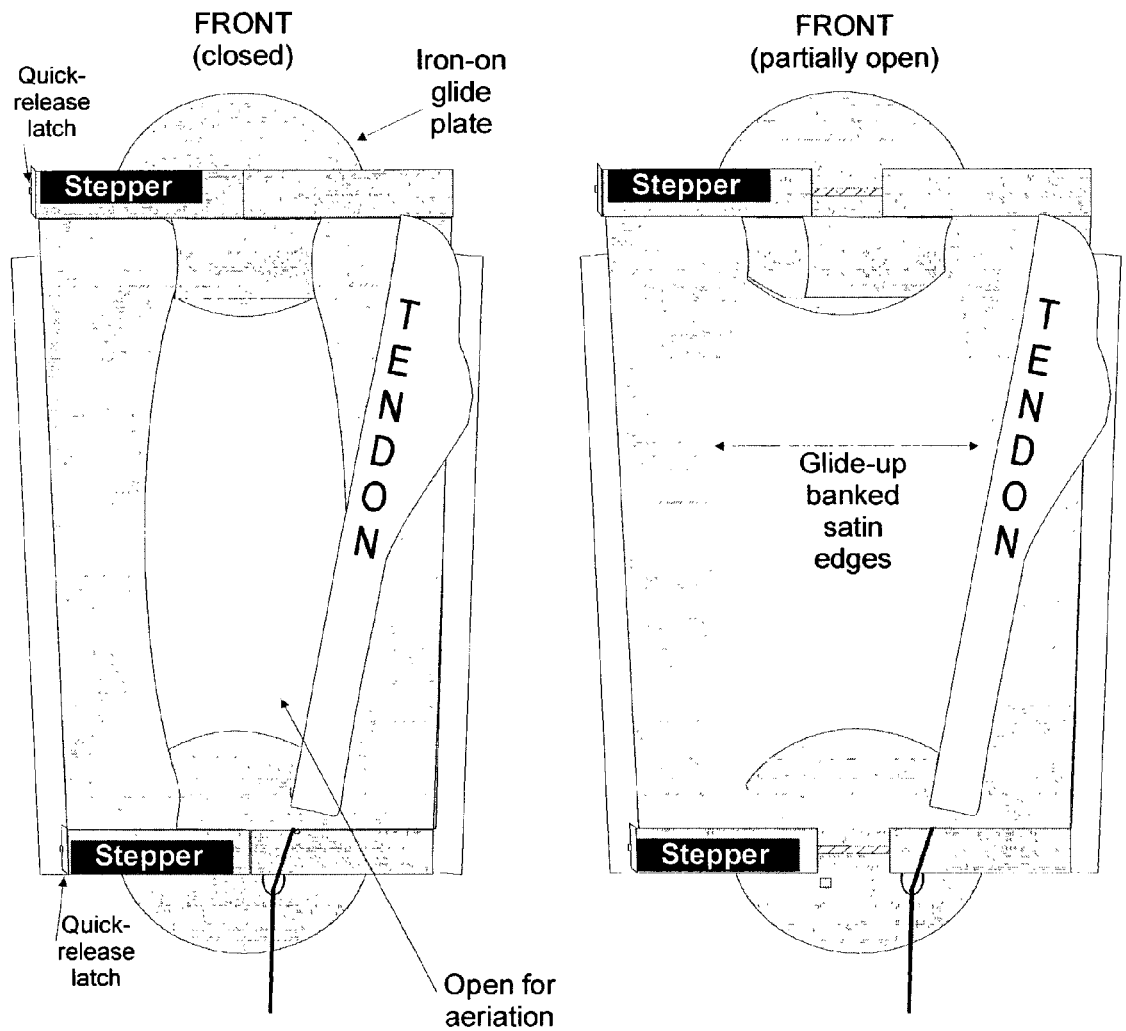

FIG. 5 provides, on the left, a front view of the ankle split-rotator of FIG. 4 and, on the right, a front view with a stepper or servo-driven separation in process. This separation is not along the vertical cuts used for quick separation but along a separate vertical cut especially for expansion. As the motors turn their gears, potentially independently of each other, the anchored but rotating screw columns moves the anchored nuts on the opposite side of the joiner (and thus move the other side of the joiner to which they are anchored) closer or further away. A somewhat rigid but narrow smooth plastic glide plate is ironed onto the thin satin undergarment just below the front opening and the back opening. This eliminates pinching or rubbing as the prosthesis tightens and loosens.

FIG. 6 illustrates three embodiments of a power-enhanced, automatically adjustable strong-side-biased actuator that, as applied in the example embodiment, can be used to reduce the amount of energy spent for certain applications and, in other applications, does the job typically done by a large 100 pound capacity actuator with a smaller, lighter 53.5 pound capacity actuator reducing the weight and size of the required equipment and delivering, in example applications, over 186% of the actuator's power. Amount of bias leverage is adjustable by modifying the size of the spindles or spring(s) in FIG. 6A and by modifying the size of the springs or gear ratio in FIG. 6B. Optional means to support the programmatic adjusting of these values to either increase power or efficiency and to provide stability and control between moves as well as to automatically adjust the equipment to a specific user body is illustrated in FIG. 6A in the form of clutches to engage/disengage spindles and brakes to temporarily fix their positions operatively connected to each of the spindles. FIG. 6B is an ultra-light version using a rubber-like elastic band as the elastic means. FIG. 6C, an alternative to tendon-based actuators, shows a pushing rod or piston-like embodiment which pushes the vertical upward from the bottom as the elastic means retracts. The exhaust fan at the bottom of FIGS. 6A and B draws air through the system from the top of each figure (through ventilation holes and the cable opening at the top) isolated by the semi-sealed area that effectively seals off the right (elastic means) side of the device (shown cut away) to force fresh air over each motor to allow extra power cycles (where coils are overpowered for large increase in torque) without overheating. 4 motors are shown which may be stepper motors or, since a shaft rotation position counter is present on the main drive spindle, any motor as directed by servo-based or otherwise position-precise direction.

Figure 7:
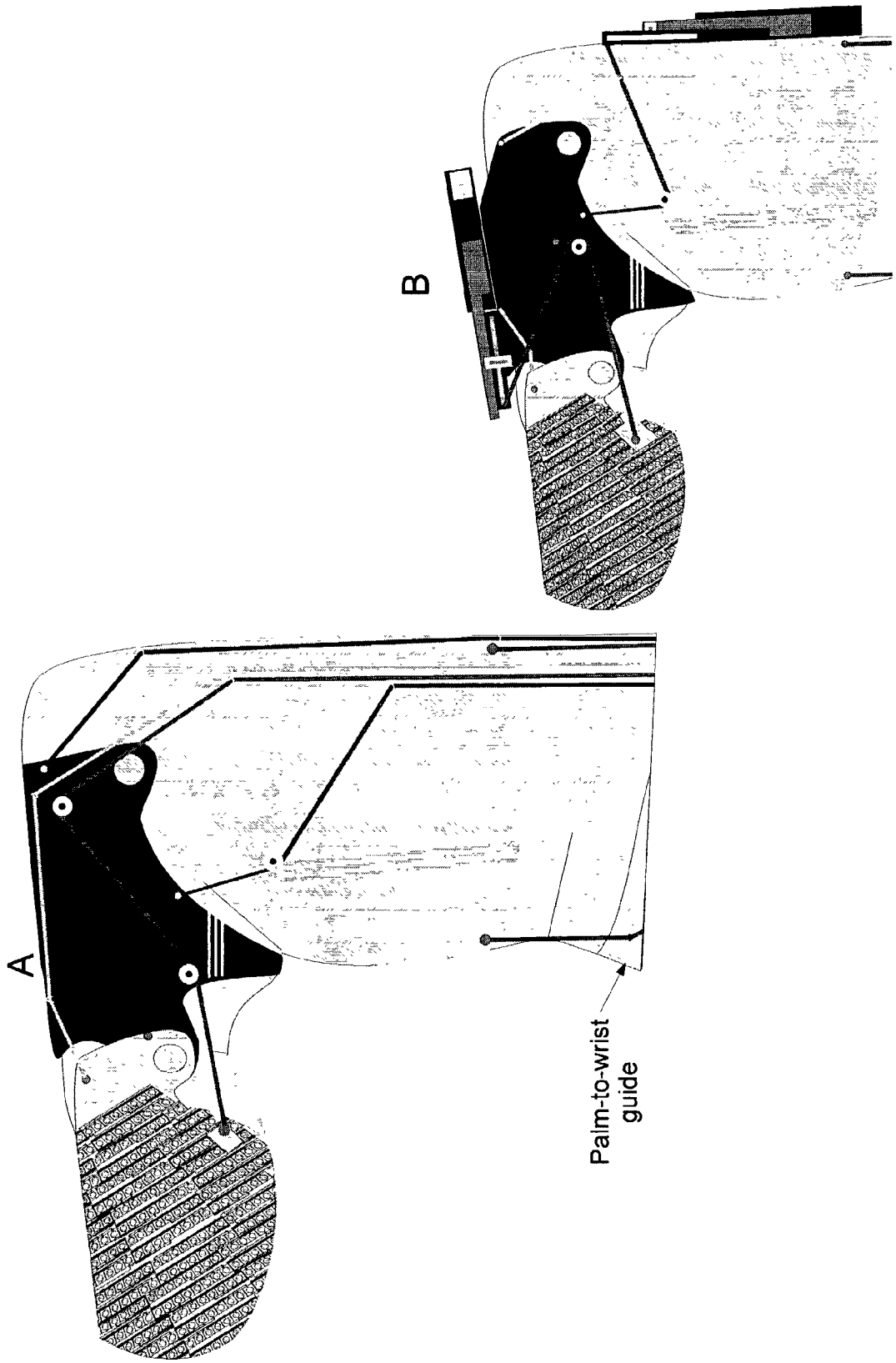

FIG. 7A illustrates one embodiment providing control mechanism for the fingers and touch sensitive sensors. Tendons follow pulleys (particularly in heavy load areas, here only to support the typically heavier flexion force) and slide-guides along the finger and past the slightly flexible (and/or jointed) at palm/wrist intersection palm-to-wrist guide (which is better visible in FIG. 1) and then to small actuators in the wrist assembly. FIG. 7B, however, illustrates one embodiment of finger-mounted actuators (here using rotary hydraulic with tubes, not shown, running past the wrist and arm to pressure means in the posterior pouch) requiring no tendons run to the wrist as reflected in FIG. 1. The touch means, better seen in FIG. 10, are connected to processing means by micro-ribbon cable running alongside the rotary hydraulic actuators on the upper-right side of the finger (not seen in side view).

Figure 8:
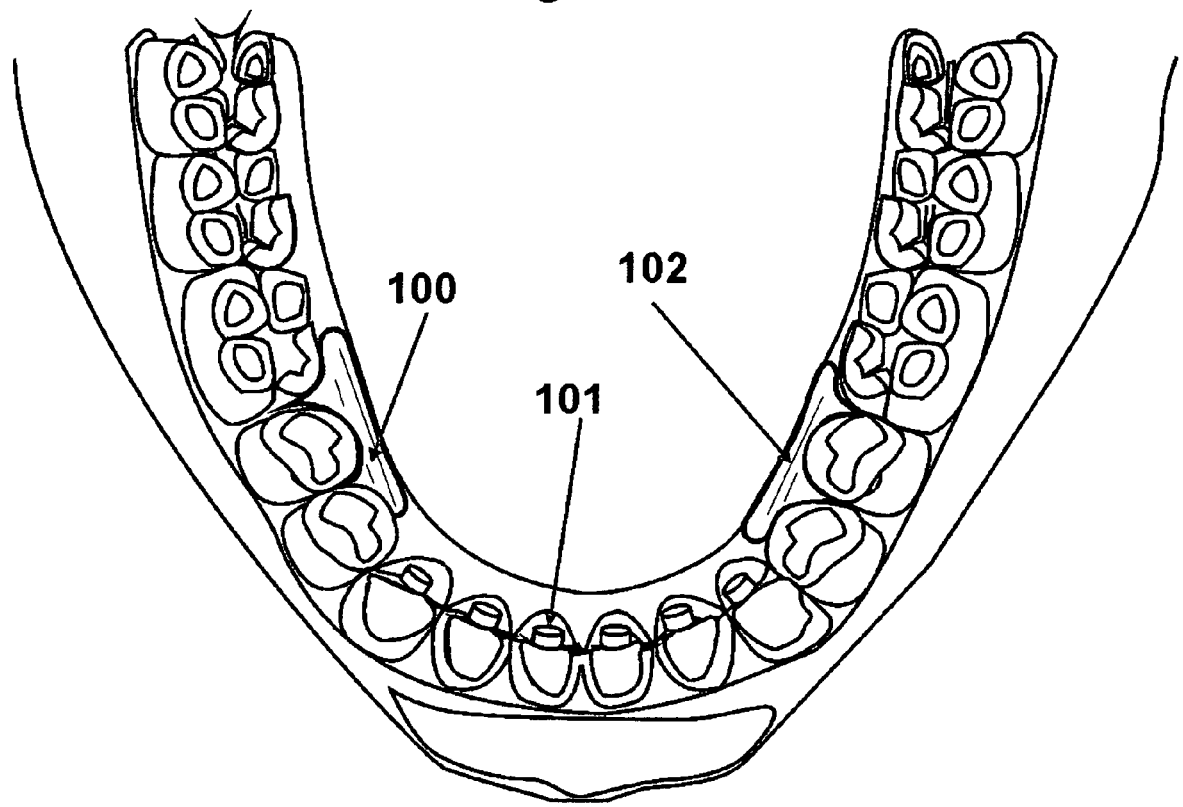

FIG. 8 illustrates a new user-interface means that allows a user to touch keys, ex. 101, located in a convenient-to-tap with the tongue location such as on or in front of the lower teeth. Also shown are the tiny wires carrying the keypress signal to the transmitter, 102, with one wire serving as an antennae for the transmitter. The transmitter transmits the keypress event to a nearby receiver. Battery means, 100, is shown to the left.

Figure 9:
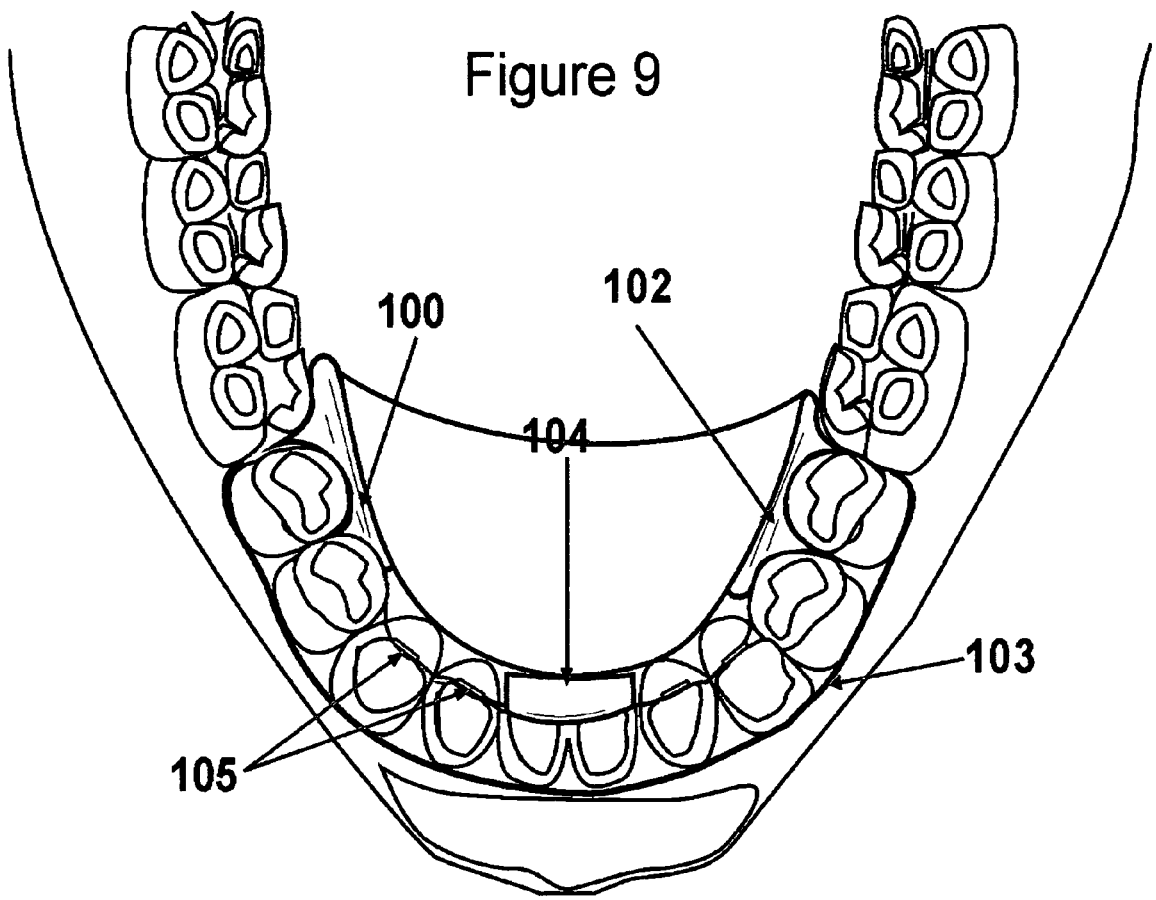

FIG. 9 adds a touchpad or mousepad, 104, for the tongue to the device of FIG. 8 and also displays flat, contact, heat and/or galvanic response sensitive keys, 105, requiring less user effort. This illustration also displays the optional fully removable assembly which fits into the user's mouth like an orthodontist's retainer. Stiffer connective wires, ex. 103, and/or a stronger connective sheath connect the keys and the touchpad with the full connective assembly allowing easy removal for charging, cleaning, exchanging, etc.

Figure 10:
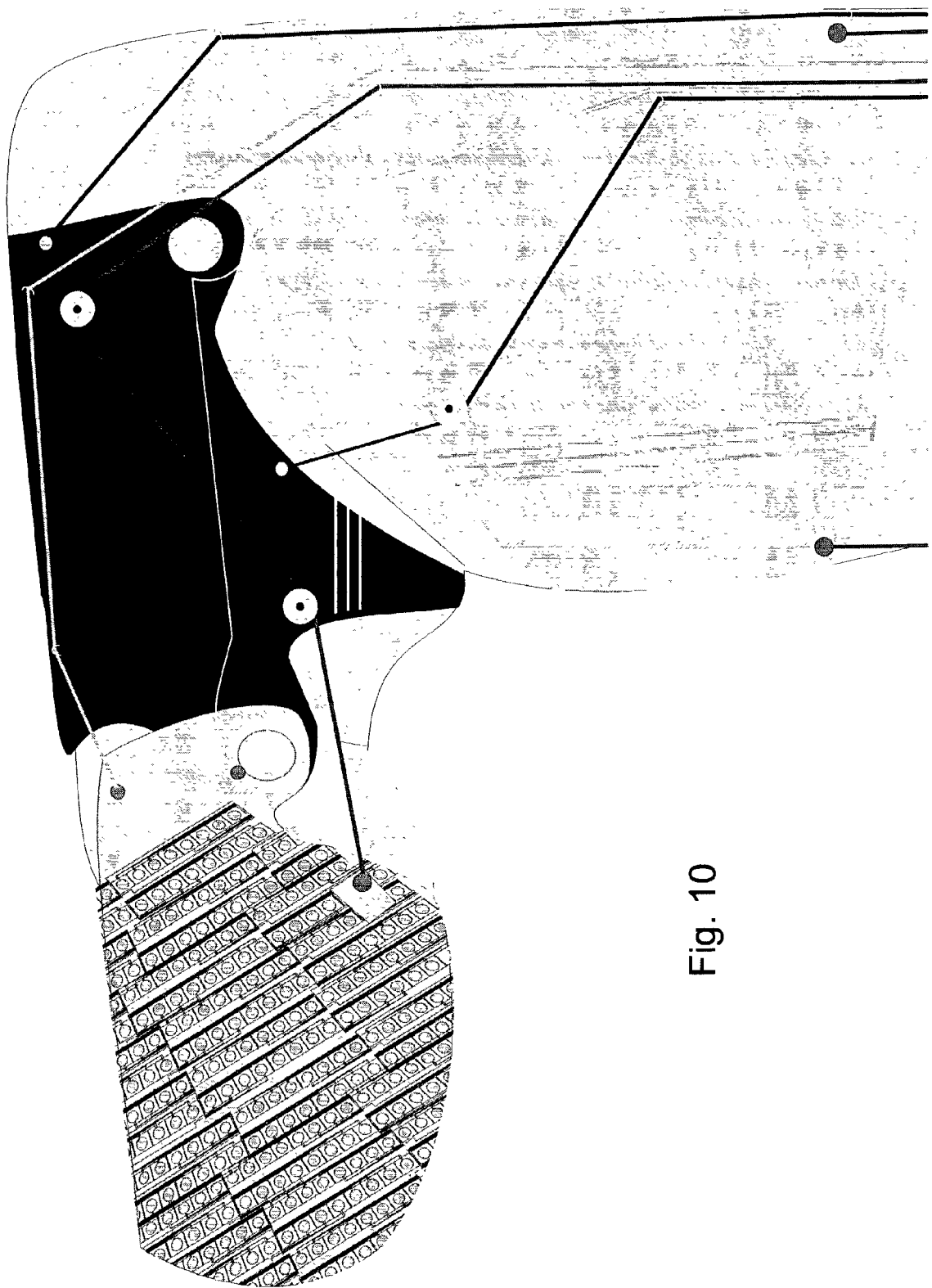

FIG. 10 is an enlarged image of part of FIG. 7A showing better detail of touch sensors and the white cable connecting them to processing means.

Figure 11:
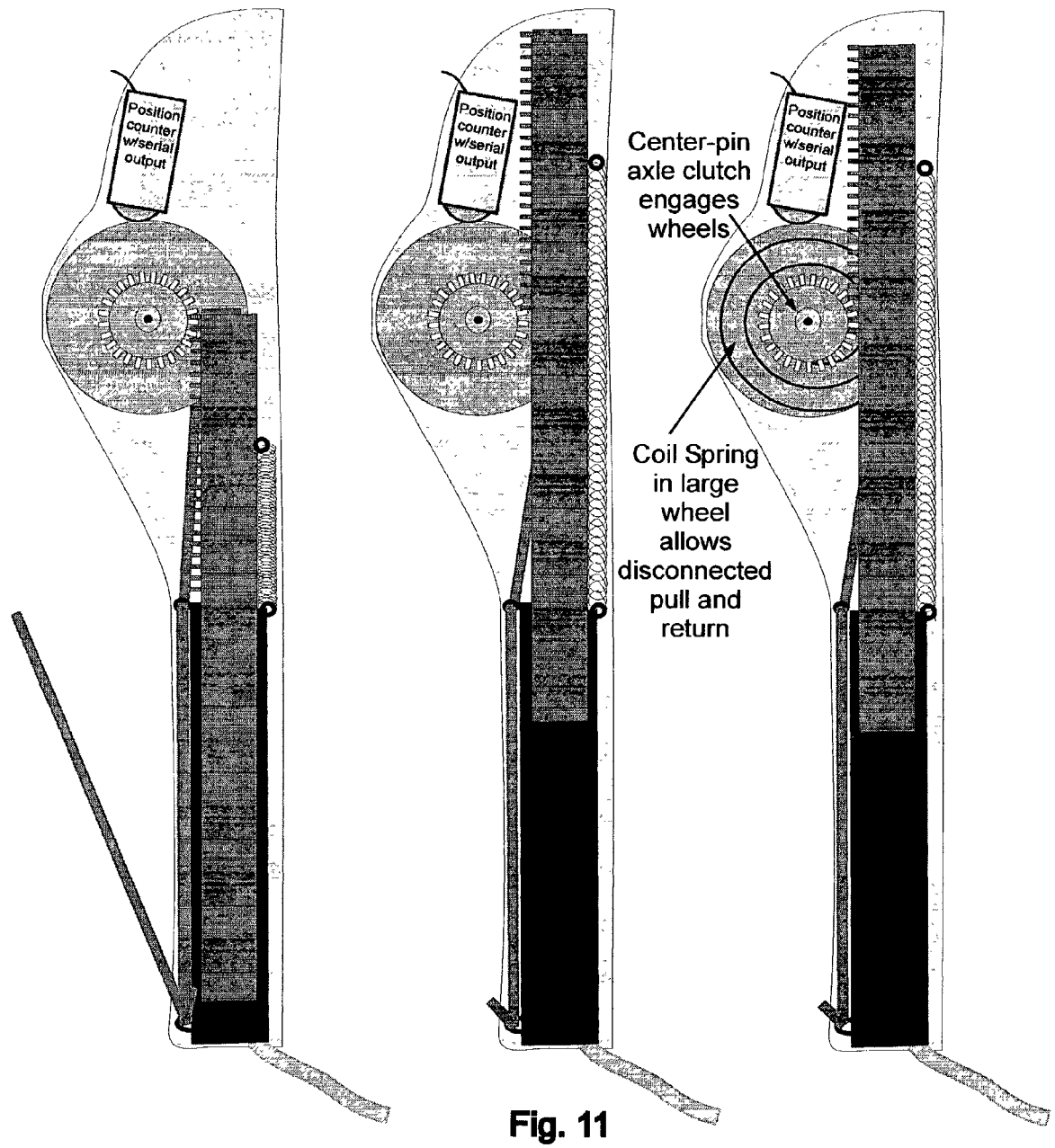

FIG. 11 is an example of a hydraulic actuator applied to pulling tendons with a piston to gear mechanical advantage providing a leveraged pull of the cables (amount of pull is a multiple of the motion of the piston). A spring at the right of the assembly is shown as the reverse return means although reverse hydraulics (either as a separate switched vacuum line or a reversal of the pressure in the existing line) is also supported. A contact roller based position counter with output to processing means is also shown. The rightmost figure also illustrates a hydraulic embodiment of the strong-side-biased actuation means (better explained in FIG. 6) which can substantially increase the usable power of the actuator as applied to a favored direction. This illustrated design, with the use of a clutch effectively separating the piston from the wheels as shown, also provides a means for the tendon to retract under its own power when the piston is disengaged such as when the equipment is being used for modeling a script.

FIG. 12 illustrates the invisible visual means which, allows the user to see the full panorama view needed by the user (unlike the current miniature monitors hung in front of user's with bulky prisms, etc.) while selectively, under user control and only when desired, projecting a visible reverse image appearing to exist in front of the user while still allowing the user the use of that portion of the user's field of view even while the optionally semi-transparent data or images are displayed.

FIG. 13A illustrates an LCD to collimator embodiment of the equipment inis an extension of the equipment in FIG. 12 while 13B shows a slight convergence by collimator distance adjustment providing a slightly convergent beam providing more advantageous distance perception and amount of data visible without moving the eye for some applications. FIG. 13C provides the top view of a beam-splitter apparatus providing a central view and FIG. 14 shows a peel-off series to illustrate an embodiment that hides the beam splitter out of the user's field of view when not in use.

Figure 13:
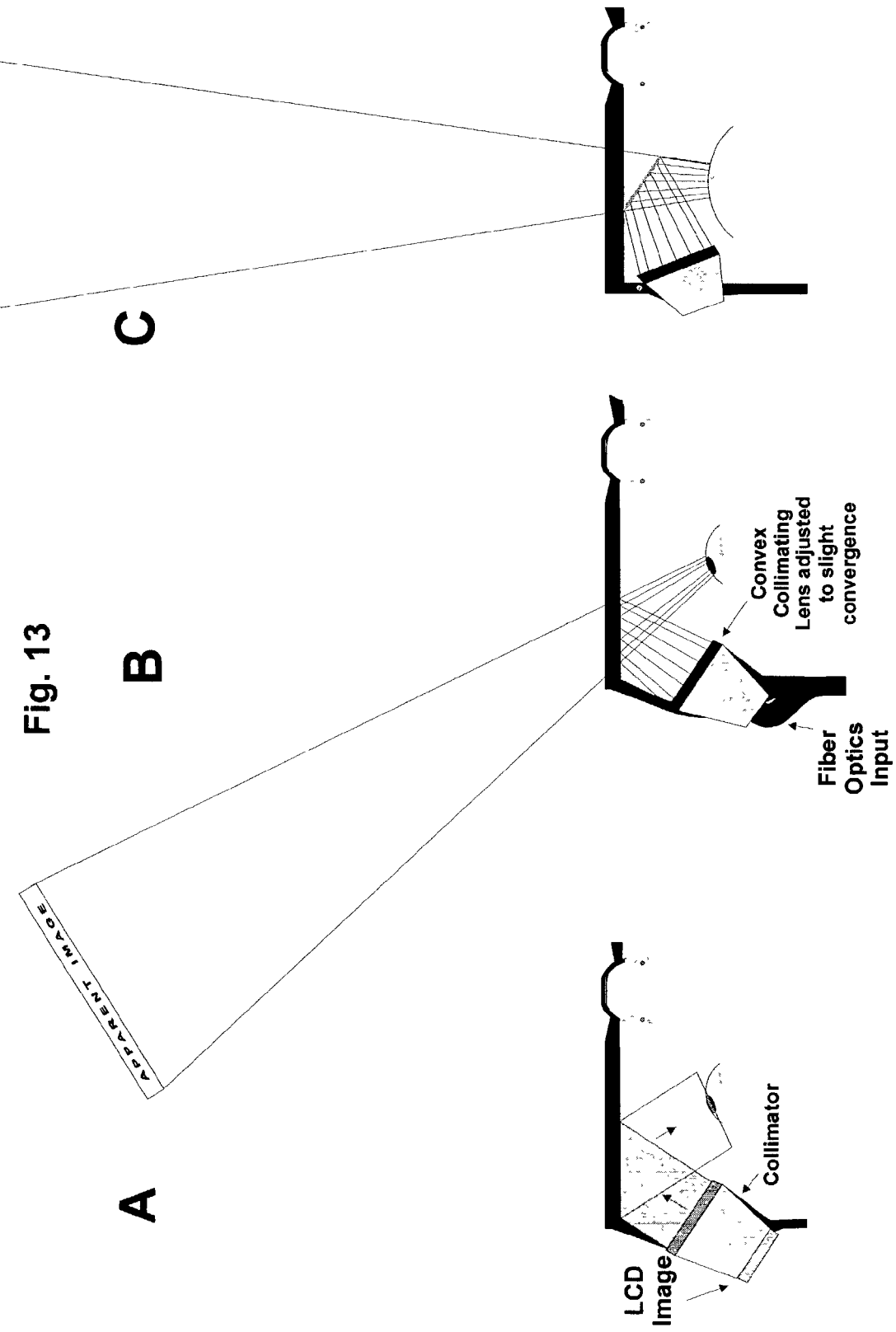
Figure 14:
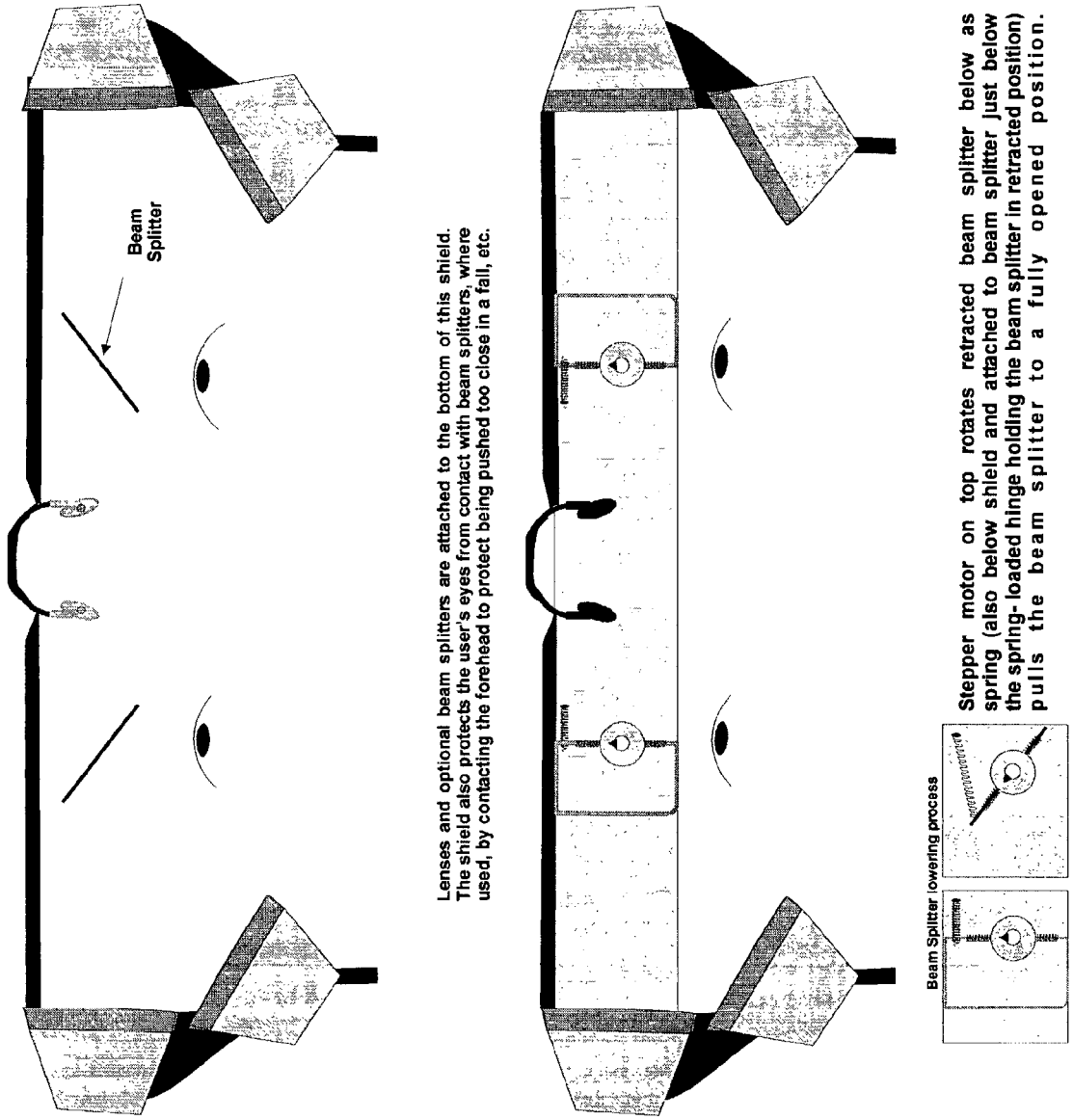

FIG. 15 illustrates embodiments of the devices of FIGS. 12-14 that combine the perspectives into a combined field of view.

FIG. 16A illustrates another viewer embodiment where the beam splitter which, like all the beam splitters in these illustrations, is optionally vacuum coated with aluminum or other partially reflective surface allowing higher signal-to-outside-view ratio. Here, the axis of rotation of the hideable beam splitter is perpendicular to the paper. The beam splitter can be parked either against the image source above or against the inside of the glasses lens when imaging is not active. FIG. 16B is a top view illustrating an embodiment providing substantially more panorama of view. On the left the two beam splitters (shown in retracted form) appear rectangular from the top. They may, in fact, be rectangular but a slightly concave to the user beam-splitter embodiment can provide field of view improvements particularly for some advanced imaging options illustrated in FIG. 17. On the right of FIG. 16B, the LCD or other image source above the beam splitter is shown taking up, potentially, all the area between the forward glasses rim and the forehead and thus greatly increasing the potential field of view, amount of data displayable and resolution. The angle of the image source and the beam splitter can be modified to further increase the image source area including angling the forward edge up on the axis perpendicular to the paper (along with the connected beam splitter making the imaging area potentially deeper without reaching forward of the glasses frame) or rotating the rear of the image source upwards resting higher against the forehead which also increases the potential size of the display. When that is done, the angle of the beam splitter is changed to correct the image to the eye and digital enhancement of the pre-transmitted image is used to pre-balance any warping or compressed images due to sharpness of angle.

FIG. 17A is a similar embodiment to FIG. 16 but using a collimator for focusing. FIG. 17B and FIG. 17C use flat projection through a collimating film preserving space in the cramped glasses area. FIG. 17C illustrates a concave to the user beam splitter or reflector that focuses the more truly collimated light into a form more easily focused upon and navigated by the user. FIG. 17D illustrates a space-saver flat focus means that uses a collimating film but warps the film in a concave to the user form thus focusing the true-collimated light in a form better viewed by the user.

FIG. 18 supports the description below of the user viewing means as applied to on-screen navigation aids. It illustrates an example of two bars, one reflecting the desired yaw of the user and the other the actual yaw of the user's main torso and how the user places the head yaw bar over the area in the user's field of view that is the destination and the visual image as the equipment responds as the user also continues to respond over time.

FIG. 19A illustrates an embodiment from the rear of the user with a shoulder actuation means that is an optional departure from the approach used in most other areas of the current invention. Each shoulder pitch actuator, so labeled, pulls narrow tendons which lead to a increasingly wide strip of laterally ripple-resistant, low-friction (satin covered here) bands which attach to the lower shoulder control point for that shoulder on the other side of the torso (said front view visible in FIG. 3B). A similar pitch actuator cable on the front widens into the darker colored satin covered band shown under the one just discussed and connecting to the lower posterior shoulder control point. When the rear pitch actuator retracts and the front pitch actuator extends, the shoulder pitch is increased (the arm is raised in front of the user) aided by the elastic lift supports 3 sets of which are shown in FIG. 3A. The lateral vector of this slightly off-axis pull is controlled by the upper and lower shoulder roll (abduction/adduction) actuators to provide truly natural shoulder action without external hardware or limited range typically caused by obtrusive and heavy equipment. Each lower roll activator shares a joint-control point on the semi-rigid shoulder sheath with the business end of a pitch control band. The two upper roll actuators (one on front and one here on the back) combine not only to provide the retention offset to the lower roll (actuators and effect roll but also provide (due to the use of symmetrically paired tendons on each side instead of one centered above the shoulder) along with the lower roll actuators, important shoulder-shrug control and true axis control. Combined they provide an unobstructed, fully dimensional control of the shoulder (including full shrug and full over-the-head pull down action) that is wearable under normal clothing. FIG. 19B illustrates an embodiment that can be seen as the upper, rear view of FIG. 3A and thus uses non-hydraulic actuators and uses tendons for shoulder flexion instead of the broad bands of FIG. 19A.

Figure 20:
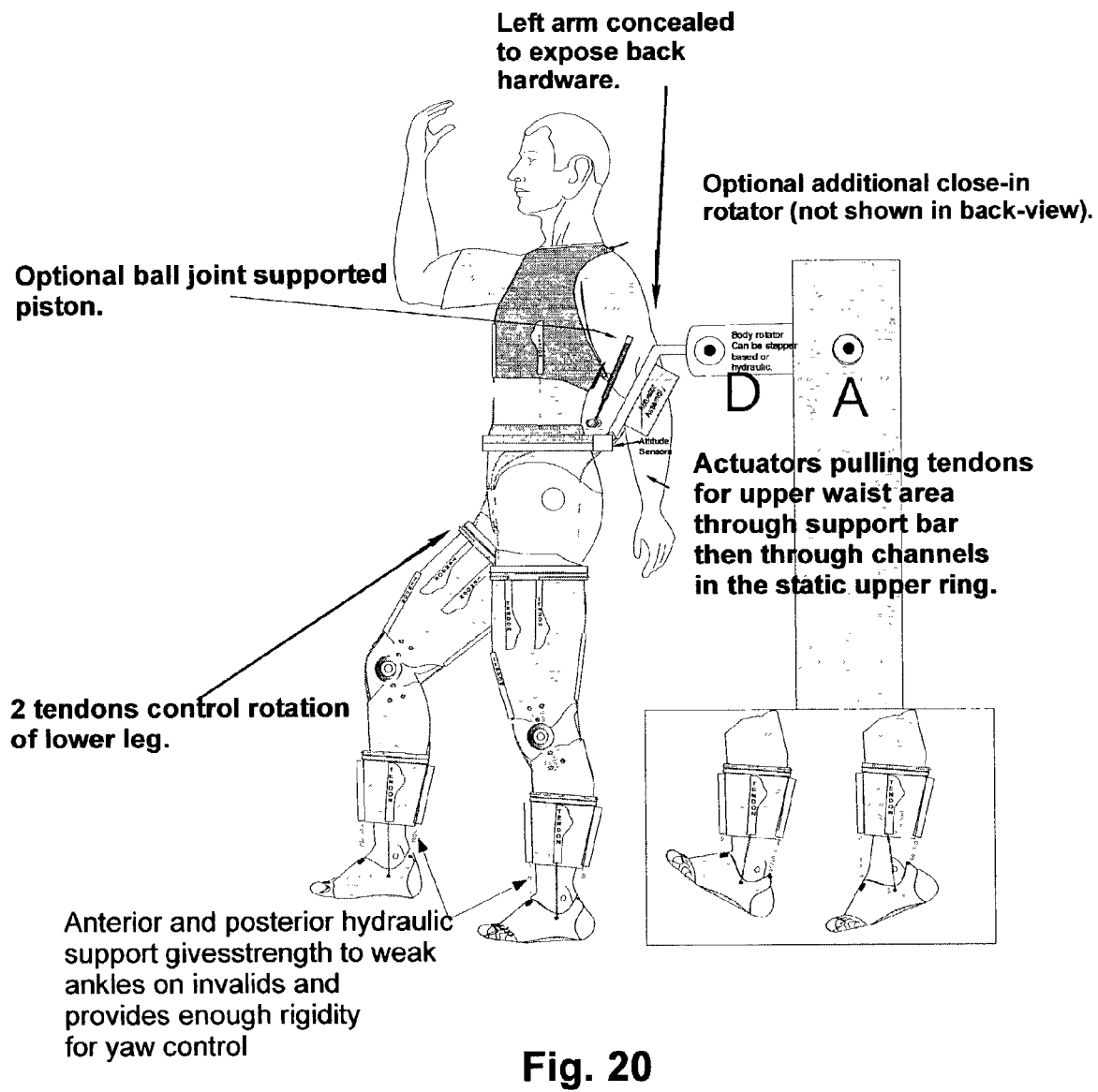

FIG. 19 also illustrates, in this example embodiment on the back of the user's neck, a touch reproduction array. This is an array of micro-solenoids and/or voice coils and/or electro or other skin stimulation means providing sensory stimulation to the area below them that the user learns to associate with touch from those limbs unable to respond to touch. These sensory stimulators are logically mapped to provide stimulation relatable to an array of sensors such as those illustrated in FIGS. 7 and 10. FIGS. 19-21 are supported by additional illustrations and extensive explanation in the foundational provisional patent application "Virtual Robot Control", 60/234,191.

FIG. 20 illustrates the suspension of the elements of FIG. 3 by a waist support attached to the waist rotator ring of FIG. 3. Because of the synchronized and simultaneously interactive nature of the connected joints, the user's weight is not felt on the waist support but on the user's feet in the example drawn and, if the user knelt, on the user's knees, etc.

FIG. 21 illustrates a mechanism that takes the user supported in every direction by the linked-joint cohesive support of the assistive clothing. Thus when the user is rotated or when the users turn themselves, the equipment can provide a 360 degree virtual response and control for an unlimited range of simulation/emulation and/or graduated-effort physical therapy from a fall-proof support and/or simulation supported physical therapy.

DESCRIPTION OF THE PREFERRED EMBODIMENTS

Using key elements of the above disclosed invention, even paraplegics can walk, climb stairs, hold a coffee cup, stand at eye level with peers, look and dress normally as well as care for themselves by feeding themselves, etc. Other advancements include a more comfortable prosthetics design that is also supportive of standard parts and that that are automatically adjustable as the user grows and can self-readjust while being worn. A visit to a hospital ward full of paraplegics in wheelchairs or the home of a child whose prosthesis is in a closet because of the pain, heat and discomfort of using it, is an effective gauge to see how impossible this has, up to now, seemed to the scientific and medical community.

The wheel-less and much more stable apparatus and process illustrated in FIGS. 3-6 allows the user to get up out of a chair (or bed), stand up, walk on uneven terrain, climb stairs and appear, with ordinary street clothes, normal. It is a spin-off from the pending patent "Natural Robot Control" Ser. No. 09/960,294, which is included herein in its entirety by reference, that also resulted in improvements to the design of:

1. assistive clothing which is lightweight, body worn equipment under normal clothing (but above a special friction controlling layer) that senses body part positions, remembers them and recognizes when the user is misperforming and/or controls and empowers the user's joints to behave as desired without bulky or external hydraulic levers, etc. (allowing the formerly disabled to look and move normally) and
2. unique software approaches (also a spin-off from "Natural Robot Control" Ser. No. 09/960,294) allowing precise and fluidly coordinated body control and
3. much improved user direction of the new equipment including several new devices and programs to allow even a quadriplegic to quickly and intuitively control his direction of travel and even delicately control his fingers and
4. enhanced delicacy from an improved prosthetic structural design paradigm and
5. enhanced precision and ease of use due to the provision of tactile feedback (touch sensation).
6. an integrated balance control, user guidance and scripted and/or programmatically controlled process that allows the user to perform complex tasks in strange surroundings and on any terrain and
7. a superior means of capturing, transmitting and processing positional data that not only makes possible the functionality of the physical joint control apparatus but also provides a "standard parts" paradigm for rapid simulator/modeling setup using complete capture and processing of complex body attitudes, incumbent forces on joints, vectors of motion, etc. in an easily communicated means easily made compatible with multiple simulators.
8. a training tool capable of quick script creation of extremely complex activities and the ability to instruct a student by warning of each divergence from a norm and/or fluidly enforcing a perfect action such as a perfect golf swing.
9. a way for someone rehabilitating from an injury that has left them with little or no control or strength to be able to walk and work while protecting them from falling when their strength gives out suddenly. Gradually, over time, the amount of support and guidance provided by the system is decreased as the patient's strength and coordination return. However, the patient is under no circumstances allowed to fall. In addition to getting the patient up and walking quickly (speeding recovery, preventing lung and circulation diseases, while reducing atrophy and in-hospital time), it does so more safely and without the constant attention of medical personnel protecting them from injury. Also, much of the tedious physical therapy process of joint travel advancement therapy and muscle stretching can be done any time the patient desires, without burdening scarce medical personnel resources and without burdening special care facilities.

Figure 1:
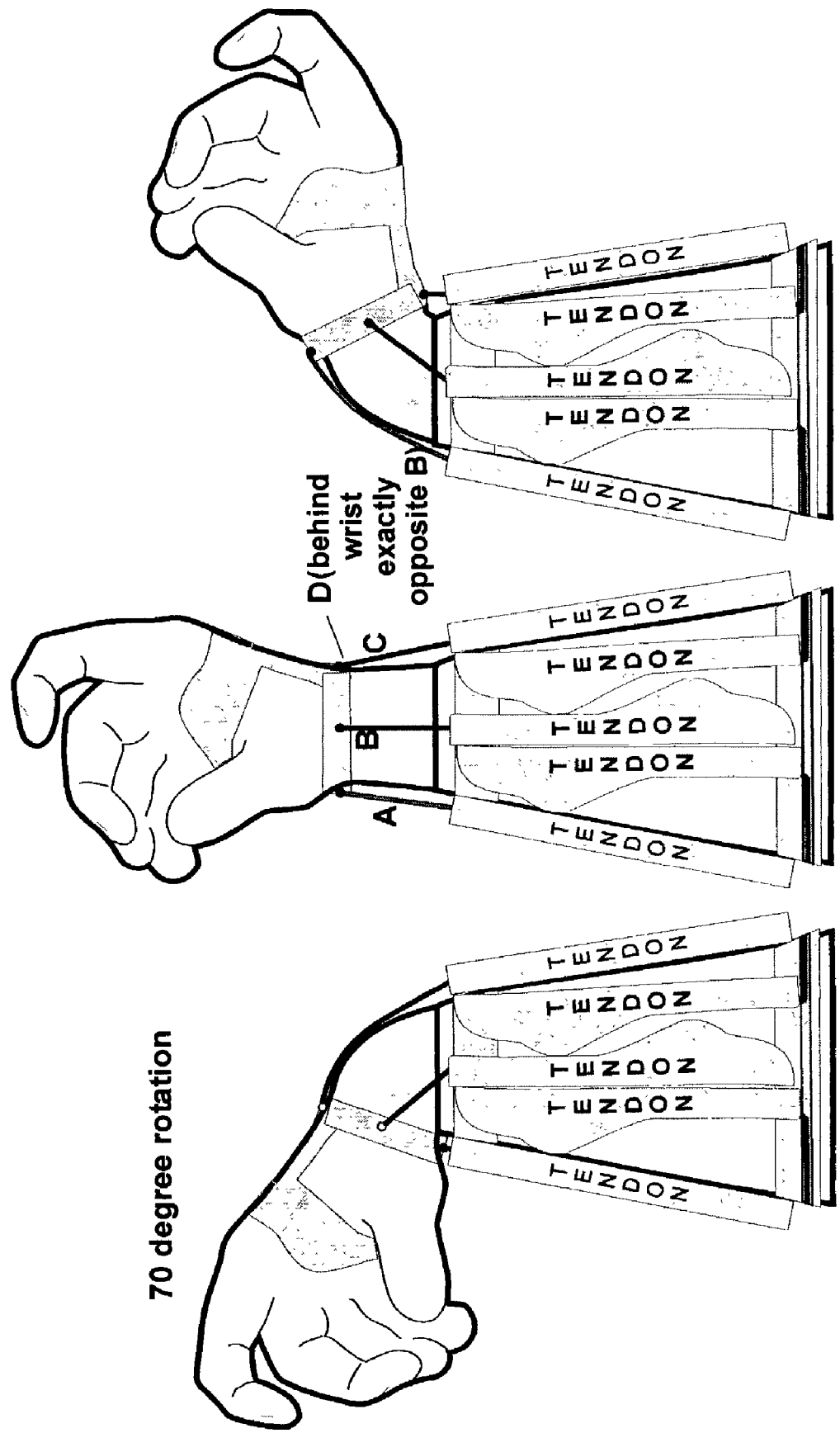
In FIG. 1 a sample embodiment of the joint control process is illustrated. Tendon retracting actuators retract, for example, tendon C while releasing pressure on Tendon A to move the hand in the leftmost portion to the position shown in the middle. Positions of pull on tendons B and D are also modified to a lesser degree in this particular motion as described below. At the same time the wrist rotation is controlled by the tendon actuators pulling against a fixed position on the lower of the two connected bearing-enabled wheels. Here there are two actuators retracted to different degrees, one pulling from the left and one to the right to provide tension and reversible wrist rotation. Other embodiments that more closely fit the wrist use the split-rotator approach used in FIGS. 4, 5 and 6.

FIG. 1 is an illustration of one embodiment of the current invention that provides complex joint control. It uses tendon (light cable) pulling actuators for retracting tendons to achieve joint angle changes and positional support in joints. (Optional tendon guides ranging from guiding eyelets to tendon "tunnels" are not displayed). The joint hardware shown is an open design minimizing weight and interference. However, for some applications, more or less full coverage external joints, also moved by these same actuator assembly options, can be used. The effective internal joint geometry is visually approximated by the imaginary ball-joint sphere superimposed over the wrist in FIG. 1 at the axis of the wrist just below the B solely to help visualize the process. Although actual wrist motion is more restrictive in some dimensions than a mechanical, full motion ball joint, within the range of motion used herein, this geometry illustrates some of the effects and demands of multi-axial rotation.

It should be observed that the illustration in FIG. 1 is not indicative of how much a joint moves in a single cycle. While the illustration shows a roughly 140 degree swing from fully bent in to fully reversed, a typical cycle might only move a tiny fraction of one degree because of the shortness of the motion cycle.

In this example, we will consider the action proceeding from the middle illustration in FIG. 1 to the leftmost illustration in FIG. 1 i.e. that of the wrist in flexion. Again, the two pictures do not represent the amount of motion in a single cycle but looking at an illustration of the change resulting from hundreds of such tiny motions in the same direction is useful in identifying the nature of the motion being considered (a one cycle change wouldn't be visible on the illustration). From the joint's point of view, the joint has been rotated (on the printed page) counter-clockwise which would mean that tendon A has retracted (due to the minimum pressure always kept on a tendon) and tendon C has extended to allow that movement.

The illustrations in FIG. 1-7 reflect one of many applicable embodiments that can be placed into service both to capture motion data and recreate the motion later. If the above action occurred during an action cataloging session where an action cataloger is wearing the above equipment connected to computing means capturing the positions over time, a new data record or memory variable or string, etc. has been created with greater or smaller values for these tendon-control points than in the just previously captured data reflective of the motion. Later, the apparatus and process of the current invention, as disclosed in great detail later, recapitulates those exact actions responsive to the captured positional data.

It is true that anything that can be "scripted", as above, can also be replicated or simulated programmatically by effecting the same actions that the script directs from programmatic instructions, algorithms and calculations with or without the aid of computer models and simulations. The skilled user in the field will observe the recorded body kinetics that are turned into fluid human action and effective user control by the assistive clothing and develop programmatic replacements for some or all of the scripts while remaining true to the concept, apparatus and methods of the current invention. Other sources of positional data, such as a live action modeler wearing sensors or real-time simulated body action (both discussed in great detail in the referenced provisional patent "Virtual Robot Control" 60/234,191) can also serve as source data to effect the benefits of the assistive clothing. Therefore, rather than multiplying the amount of documentation by redundantly disclosing it for each and every source of positional data individually, a scripted process when described here is understood to represent any source of positional information for the sake of brevity. Similarly, there are many forms of actuators capable of accomplishing the actuation needs of the current invention. Thus, where any other actuation means will accomplish the same work, those actuation means are included even when there is only one actuation means specifically listed.

To make above example using FIG. 1 simpler, we will ignore the changes in tendon B and tendon D (hidden behind hand in FIG. 1) for the moment even though they do change (but do not affect the result). Also, the angle in the Z dimension (perpendicular to the printed page) never changes in FIG.

1. thus confining the wrist's movement to the plane of the paper. Thus, the data storage means will store for this point in time a retracted (now smaller) value for control point A while control point C will have a new value for this point in time that is extended (now a larger) value.

Later, when the assistive clothing is following a script and/or program and is in a mode that requires the assistive clothing to emulate the script and attempts to emulate this just modeled action, control point A's actuation means will contract to the position recorded in data storage means for that point in the script while control point C's actuation means will extend it's position to match the recorded position. This is functional (the joint now matches the script) and the process could stop here as it does for some embodiments. However, there is great value in complicating the issue somewhat with additional kinds of actuating means and advanced support technologies.

FIG. 3 illustrates a standing body wearing a couple of the many applicable embodiments. In FIG. 3A the ankle uses the aforementioned split-rotator process in which the rotator shell loosens and tightens at splits that can be on 2 sides. It, like the waist version of FIG. 3B (which is enlarged at the bottom of 3B) is supportive of a closer, less bulky fit, automatic self-adjustment and ease of dressing. The waist assembly of 3B rotates on bearings with the vertical tendons firmly maintaining upper-torso position and, in coordination with the low-friction ribbons (with slight and controlled elasticity) (the diagonal band from top left to bottom right terminating on the rotating ring's semi-rigid grasping padding) and the waist rotation stepper motors on both sides, moves the upper-torso as directed by the processing means. (Because it is tedious to describe every applicable actuator technology in detail with every reference, all references herein to stepper motors, tendon actuators, etc. as examples are understood to refer to any actuator means providing accurate, position-controllable actuation applicable to the task.)

In FIG. 3A, however, an embodiment is illustrated in which the entire waist assembly is reduced to a semi-rigid, internally friction intensive, optionally waffle-vented (for circulation) broad-belt. This embodiment can also be rapidly removed as well as split and automatically expanded, contracted and repositioned using the same or other expansion and programmatic means used in the waist assembly of FIG. 3B. It does not need to be tight or uncomfortable because its position is not dependent on grasp but the pull from below offset by the pull from above. Upper-torso rotation, without benefit of the stepper powered, bearing-supported rotation of 3B, is performed by actuators, here located on the upper body, with tendons whose retraction on both sides of the body twists the upper torso. In the embodiment shown in FIG. 3A there are two tendons on each side with one pulling the torso in a clockwise and the other in a counter-clockwise fashion. Retension processes described below eliminate slack and maintain firm positional control. The resulting off-rotational (not in the horizontal plane) element of the resulting upper-torso vector is controlled by the vertical waist control tendons which offset the slightly off-axis pull as a natural consequence of the manner in which processing means controls the elements synchronously.

Automatically Cooperating Tendons: This crossed pair of leg-rotating and abduction tendons as well as the medially located corresponding leg-rotating and adduction tendons also provide lifting support to help the anterior thigh flexion tendons in the lifting process at the hardest point its the lift burden. Returning the favor, the anterior thigh flexion tendon reciprocates and aids the crossed pairs in parts of the process of both rotation and adduction. Numerous other mutually beneficial combinations of these and additional tendons or other actuation means are limited only by the desire of the implementer and the cost and the space taken up by any new required actuators. This is made possible by the combined contributions of the retention process and the synchronized parallel nature and design of the actuator system that automatically directs the cooperative aid of ancillary tendons which maximizes the combined power of the cooperating actuators while minimizing the size and weight of those actuators.

The waist assembly of FIG. 3A is, like the one in FIG. 3B, is hinged for quick release, here in the back of the user with quick-snap-off latch over the vertical tongue-and-groove joined opening on the user's right front. On the rear there is a corresponding vertical separation controlled with a reinforced Velcro hinge. Although strategically placed rigid hinges or other hinge arrays will also work, the application of reinforced Velcro on both sides of the vertical opening allows a new user to customize the fine fit of the equipment by simply placing the opposing polarity Velcro over the opening much as one would apply tape to join two surfaces. This provides not only an angle-of-rotation-tolerant, slightly flexible hinge but an easily adjustable apparatus for users of different sizes to attain a perfect fit as well. For badly deformed users it also provides an additional separation point to place the equipment into position without requiring much user mobility. A heavier user would have reinforced Velcro spanning a significant gap while a very thin user would have no gap at all under the reinforced Velcro.

Any number of additional tendons or other joint-control means can be added to the current invention without departing from its scope or confusing its mechanics. Because the process can begin with an action cataloger wearing an effectively identical configuration as will be worn by the user, any number of additional joint controls will be synchronously and copasetically reflective of the action cataloger's body attitudes but simply from more points of view.

In addition to the above means for the quick donning and removal of the equipment, the current invention also includes an expanding actuating means front and back to provide aeration, massage and powered, on-command loosening for automatic or manual adjustment optionally in the same manner illustrated for another joint area in FIG. 5. Where hydraulic actuators are used, hydraulic lines run from them to the backpack (not shown) or to the assembly container (located and shown near the small of the back). Both the snap-off, hinge-based fast-dressing design and the powered expansion for automatic adjustment, massaging and circulation support are applicable to all the body-control elements of the assistive clothing.

Where electric-powered actuators are used, such as the enhanced power stepper motor based tendon actuator of FIG. 6 (which can, of course, replace any of the tendon-based actuators shown in any of the figures), the thin power wire, not drawn, runs from the back of the actuator to the assembly container ideally through the assistive clothing into which it is embedded. Processing means, in the form of a battery powered controller card with serial output leads in one sample embodiment, is also located in that assembly container.

Parts of what may be taken for an exoskeleton can be, in fact, soft and somewhat flexible and waffle-cut vented as long as the material doesn't stretch significantly laterally. In the embodiment shown here, the upper-torso can be a non-stretchable but soft, fabric or chain-mail with proper fitting and while continually position-controlled by the strong and mutually-offsetting retention process described below (which keeps the assembly in position). However, it, like all the external body-form attachments can also be more rigid and hollow to contain rechargeable battery power and to embed actuation means so that they do not extend more than necessary above the surface to provide smooth "body" surfaces invisible through clothing, for example. The more rigid illustration shown in FIG. 3 provides those advantages. For long distance travel a small back-pack or connected attaché to carry more power will permit extensive power and/or enable more comfortable assistive clothing than the embodiment of the current invention illustrated in FIG. 3 where power is stored only in the assembly container and/or semi-rigid body-control covering.

FIG. 3 also exposes, on the right knee of FIG. 3A, the knee rotation guide's optional spring based anti-flexion support (there is one on each side) which contributes lifting power during the heaviest burden portion of most activities such as the straightening of the loaded knee in step climbing (which, unlike a striding load, places all the weight on a limb that has no economies of vertical joint locking support and which must provide, from a very disadvantageous initial degree of flexion, complete vertical acceleration of the full body weight). Here, any form of spring in opposition to flexion contributes enough power to take a load off the anti-flexion actuators. In this application, it permits the implementer to use a smaller lower-anterior thigh actuator array (just above the knee). Of course, this puts more load on the lower posterior thigh actuator but this actuator has much less maximum burden to bear in the first place. This prevents the lopsided and typically oversized, cosmetically robot-like actuation means common to some prostheses while increasing potential for loads with smaller, lighter actuators.

The black lines looking like tendons that are visible on the left shoulder of FIG. 3A and labeled in the rear view shown in FIG. 19A "Abduction (pitch) Enhancement Bands", are not tendons but elastic cords (optionally replaced by other elastic means like springs). Like the knee apparatus just above, these provide a fixed lift in one direction reducing the amount of work required to flex or abduct the joint.

To the casual reader this shoulder support and the knee elastic means just above it appear to be overlaps or redundant features congruent to the biased actuators of FIG. 6. However, they are completely separate and additive. They are separate in that FIG. 6's elements are biased within the device of the enclosed/isolated actuator itself providing more selected-polarity direction of power from the actuator assembly in a compact and adjustable means that results in a substantial increase in output of force applied to the tendon. On the other hand, the knee anti-flexion spring and the Abduction enhancement bands and similar lift enhancers applicable to other areas, do not increase the output power of the tendon pulling device or control its implementation and reversal but, instead, separate from the extra-strength actuation means, independently just bear a share of the load depending on the smart actuators associated with them to handle any problems that occurs when the bias works against the user such as when the user is not vertical. They are additive in that, in addition to biasing the inter-limb actuator assembly in favor of areas of maximum power required using the anti-flexion knee assembly and the Abduction enhancement bands, the illustrated embodiment additionally provides the added power of the strong-side-biased actuators of FIG. 6 to provide more applicable power in less space and from weaker and smaller actuators.

The optional "shoulder pads" used in FIG. 3A that cover the redirecting pulley for the anterior shoulder pitch actuator and the anterior shoulder roll actuator can be seen in enlarged form from the back in FIG. 19B and serves not only to protect the pulleys from creating visible lumps in clothing but also serves to protect the equipment from jamming on clothing. These shoulder pads, firmly anchored on a reinforced foundation and allowing rotation on the strong, hinged axis, also provide a stable, extended platform for a vertical tendon retraction to the front and backs of the upper arms for superior shoulder pitch control without cramping the user's range of motion since they rotate easily out of the way when, for example, the shoulders shrug or arms are raised above the head. The pulleys in FIG. 3A are embedded in the underside of the molded shoulder pads also providing simple cable guiding channels in the molded form. However, where the shoulders are required to project directly upwards as if hanging from a bar, these pulleys will need to be placed slightly on the opposing sides to permit the full range of pull. Because the action cataloger who creates the scripts, etc. that guide the user wears effectively the same equipment, the distorting effects of such a moving pulley platform are naturally accommodated by all the other joint-control devices that move for the cataloger and then naturally move synchronously in a parallel fashion for the user as those actions are recreated.

The human body is symmetric yet unbalanced to better achieve, for example, the uniquely efficient and terrain-independent off-balance walking process. Thus many reversible-force devices such as rotary stepper motors, when placed in an application such as the lower anterior thigh actuator of FIG. 3A, have a substantial imbalance in load. This particular actuator assembly is used to straighten the knee under a full load up stairs but normally needs little effort in the opposite direction to loosen the tendon (in fact, it doesn't need any effort at all since the opposing tendon provides that as a natural result of its job of knee flexion). The device with two of its embodiments illustrated in FIG. 6 takes some of the power that would otherwise be available, in this case, to support flexion of the knee in this example, and uses it instead to support the strong-side (with the heavier load) of the cycle i.e. extension. Consider the device of FIG. 6A used as the lower anterior thigh actuator of FIG. 3A which is required for stair climbing to deliver a force of Fn (force in Newtons) to increase extension (the strong side of the cycle) rapidly enough to satisfy the implementer's requirements. In this example we assume that 7% of Fn is required to support flexion to meet the implementer's objectives (thus Fw, the weak side force required, is 0.07*Fn). This is a little generous (zero is a possible value) but provides some room for error and circumstances. Instead of buying the more expensive, larger (harder to hide) and heavier actuator rated at Fn, the designer chooses the device of FIG. 6 with an actuator rating of:

$$An=(Fn+Fw)/2$$

Where An is the required potential actuator force in Newtons. Since Fw=0.07*Fn then, by substitution An=53.5% of Fn thus the size of the actuator required is, for this application, just over 50% of the otherwise needed motor rating (allowing a much smaller motor to be used).

This is accomplished programmatically in this example after initially selecting an elastic means that at full extension exerts a force of (Fn−Fw)/2 or 0.465 Fn. Then, as this knee extension actuator nears what would ordinarily be its lightest work (the initiation of knee flexion where no extension force is required and, in climbing steps, where no heavy load opposed the flexion on the now free-swinging leg), instead of resting, it must exert, at that worst case point, a force of 0.465 Fn in opposition to the elastic means which would oppose the desired flexion thus leaving only the 0.07 Fn extra capacity that the implementer chose to have left over. This is extra work for the actuator (borrowed for later payback).

When, however, the assistive clothing desires to effect extension, the actuator has its rated power of 0.535 Fn plus the previously actuator-resisted elastic force of 0.465 Fn delivering a combined force of a full 1.0 Fn Newtons as desired. These percentages are easily modified based on type of application and implementer preference. The above provides an inexpensive, small, light and efficient mechanism for using small actuators to do big jobs. It can be seen that in the above example, the same amount of work is done as would have been done by the larger actuators. However, the current invention is tunable to provide a range of service running from maximizing preferred-dimensional power in a multi-dimensional actuator as above to actually doing a lot less work and consuming less energy thus increasing operating time between recharging. It can even make these changes between operations such as serving as an exceptionally efficient knee extension actuator for walking and, when switching to a step climbing script, becoming a much stronger, more strong-side biased actuator for the more power-requiring act of climbing steps.

Although the original working specifications involved, in place of the 4 in-line motors shown, a single off-the-shelf, encoder controlled, servo-based graphite brush motor (delivering 6900 RPM's geared 33:1 via planetary gearhead for an effective 209 RPM's on a spindle radius of 0.65" thus pulling the tendon at a rate of 4.72" in ⅓ second with a vertical burden of 56 pounds to provide, with the strong-side biasing, a pull of about 109 pounds), which is a practical embodiment of the current invention, a combination of smaller motors in-line (as shown) provide an equivalent combined force with off-the-shelf parts, providing even flatter, more concealable equipment.

The twin spindle embodiment shown provides a simple means of gearing/leveraging the amount of stored potential released per inch of tendon retraction by choice of the diameter of the spindle-winding surface. The spindles in this illustration are placed at opposite ends of the long rotor (which can be advantageous particularly for certain solenoid-based clutch assemblies and where it is desirable that they be used on both spindles). For economy, the stepper motors shown have position locking means (ratchet, current controlled or otherwise based) in each motor to maintain an achieved position until receiving additional instructions without the power drain of continually requiring inductive force to maintain the position. However, where other motor designs are used, ratchet-based or other position maintaining means can be attached to the long primary rotor shared by all the motors.

The optional use of these clutch-based and/or other obvious means to selectively engage either or both spindles with or without brakes all responsive to computing means makes it possible to automatically adjust not only the position and tension of the tendon for automatic configuration and equipment positional adjustment but also provides means to adjust the amount of distending of the elastic means. This makes it possible for the current invention to programmatically adjust the length of tendons to a user's body for a custom prosthetics fit and also balance the ratio of actuator load to elastic support to desired control power and efficiency relative to the user's weight or even what the user is doing at the moment. The device is, in that embodiment, selectively adjustable even on-the-fly (in the midst of an operation or a transition to provide context-sensitive functionality) to switch anywhere from maximum power exerted on the strong side to degrees of added economy. These adjustment capabilities also open the door to a vast array of options, most programmatically controllable, such as the ability to disengage the elastic means for exceptional or accidental circumstances, make custom and even context sensitive adjustments to elastic means' strength, and even "jacking" up the distention (and thus the potential strength) of the elastic means well above the power of the actuation means to so distend it for special actions by choosing to effect that excess distention during points in a stroke where the weight of the limb being controlled contributes its weight to the process.

Example of tuned for economy. Consider the device of FIG. 6A as the actuator for the anterior shoulder pitch actuator of FIG. 3A. Because the normal weight of the arm provides pitch-reducing force, it is not necessary for the motors to expend as much energy to oppose the elastic means. However, some force should be reserved for this function because, in various points of the pitch reducing stroke, varying amounts of resistance to the elastic means are required (both because the tension of the elastic means varies in the stroke and because the geometry of the operation places different burdens on the tendons in various positions) and a firm control needs to be maintained. Suppose, for example, for a particular user's body meeting the goals of a particular implementer, an elastic maximum strength for efficiency in light-duty actions is determined to be 0.25 Fn (instead of the more powerful 0.465 Fn in the previous example). For a script or other actuator application requiring such light-duty work, then, this value, on the average, reduces the energy required to lift (due to the lifting aid of the elastic means) more than it increases the energy expended by opposing the elastic means (due to the help of the arm's weight doing that for it). In a well balanced system, very little controlled opposition will be required since the weight of the arm, in this example, extends itself in most vertical positions while substantial work is reduced by the aid of the actuator-integrated elastic-reduced burden.

Thus, the actuator assembly burns up much less energy than classic actuators while maintaining strict control when needed. However, when, for example, a script requiring more positive pitch strength is loaded, processing means responsively directs the actuator assembly to lock the tendon spindle (in this illustration with a brake), disengage it from the rotor (here with the clutch) and have the motors rotate (here in a counter-clockwise motion as seen from the bottom of the page) which can be seen to further distend the elastic means such that the elastic means is more distended to the point where, for example, it now provides, at its maximum, the more powerful 0.465 Fn associated with the earlier power-enhancing example settings. The tendon spindle brake is then disengaged and the spindle connection to the rotor re-engaged and the device is now "stronger".

Now the device can lift more. While there are now portions of negative pitch shoulder rotation (particularly at −90 degrees, arms straight down at sides, where it doesn't take much strength to increase pitch) where more significant resistance to the elastic means requires more energy expended by the actuator motors to achieve the point (but not to hold the achieved position) during what would normally be a "rest" cycle, a more powerful lift is now possible in the work cycle.

The ability for an actuator device to be able to switch from an exceptionally efficient, even work eliminating, mode to a much more powerful device is a particularly useful solution to the problem of leg-mounted devices that need to be efficient for long walking range but also must be much more powerful for step climbing, etc. The current invention allows both in a means easily controlled by processing means.

For many if not most applications, the processing means is actually keeping up with more numbers than it seems but it varies by actuation means. The objective for this additional portion of the process is, however, regardless of the actuation means used, the same. That objective is to secure the joint in a powerful, three-dimensional geometric grasp that somehow:

a. provides complete, precise, and numerically predictable control over a potentially loose joint with atrophied muscles and tendons and
b. eliminates the need for the tight, unyielding hardware generally associated with prostheses that clamp on to flesh covered body parts and
c. overcomes the sore-creating nature of many joint related prosthetics which cover up (particularly in areas where heat builds up) and rub precisely against the most sensitive areas (creating more heat) that the prosthesis should be trying hardest to protect and
d. supports an improved overall design paradigm supportive of:
  1. prostheses that don't lose their fit as the user's body changes (particularly applicable to prosthetics for children who have to readapt to each expensive refitting) and
  2. prostheses capable of continuous automatic re-alignment while in use for better operating precision capable of action-type-context-sensitive automatic position, fit and firmness customization and
  3. a standard parts approach to prostheses production that provides the economies of scale capable of minimizing production and customizing and maximizing the number of people who can afford to get out of their wheelchairs and
  4. prostheses that can "out of the box" be automatically self-configured by unskilled users and/or physician assisted either remotely over the Internet or other data connection, or physician assisted in person using simple, software supported procedures that adjust the equipment to the user's particular body and application-specific needs.

The means to this end in the embodiment illustrated in FIG. 1 are threefold.

First Means: By grasping and applying pressure and/or impact to the limb not at a sensitive end-point such as a point of amputation but rather from points above:

a. the pressure can be spread over a larger area and
b. the circulation and massaging features of other embodiments (one of which is illustrated in FIG. 5 and explained in more detail further below) can provide additional relief and comfort and
c. the limb receives substantial positional stability and strength from "tendon-based" support from above the prosthesis rather than on the edges of the point of amputation almost as if the partial limb were not there at all since the work is done by and the stress is upon the prosthesis above and below a point of great potential discomfort and possible damage when used for extended periods. The partial limb is allowed to almost follow along rather than bearing much of the load.

Consider the person in FIG. 3A as having had the left leg amputated mid-calf and the foot that is illustrated there to be an artificial foot. The anterior and posterior ankle tendons are also replaced by supportive hydraulic pistons or other actuators providing vertical support as illustrated in FIG. 4 (left) and in more detail in the prior provisional patent 60/234,191 (the left and right ankle tendons remain as they are in FIG. 3. There can be relatively soft cushioning or even air space below the point of amputation rather than potentially painful contact with the prosthesis in the impact plane. Also, the apparatus around the point of amputation would ordinarily have to clamp on tightly placing pressure directly on the point of amputation creating heat and restricting circulation resulting not just in damage but untreatable itching and hot spots as well. Also, tendons and hinges above the calf binder provide angular support to the lower prosthesis rather than placing pressure on the lateral edges of the point of amputation.

In the example embodiment illustrated in FIG. 4, the assembly is easily removed with the quick-release latches shown at left and more visible on FIG. 5. The rotation ring has a vertical cut allowing its separation after the latch is open as does the lower ankle control ring and the body shell between them. However, both the rotation ring and the lower ankle control ring also both expand and contract under their own power with stepper motors extending the screws to make them more open. It would actually come all the way apart at both front and back if processing means instructed it to. (In fact, in one embodiment, the snap off assembly described below is eliminated and the ankle assembly removes itself by simply expanding the rings and their control shells until they separate).

Thus, the assembly can be alternately, synchronously or in a serial pattern opened/expanded at both front and back in a graduated fashion by rotating bearing screws under the command of the processor to selectively loosen and tighten the grip to grab tight just prior to a load bearing portion of the stroke or, at idle times in addition to similar tensioning and loosening of tendons for the same purpose, to promote circulation and comfort by massage and aeration (as it expands the vacuum draws fresh air in and at compression it expels the now heated air).

However, the experienced prosthetist will observe that, without the amputation point absorbing the pounding of the pavement, the equipment around above it will eventually "ride up" out of position unless the equipment is put on so tightly as to become uncomfortable over long periods. However, other features applicable to the current invention overcome this obstacle while increasing overall comfort. Those features are a. positional sensing means, b. calculated-offset back-tension processes and c. automatic adjustments. Thus, when the positional sensing means (such as a the tendon position reporting devices of FIG. 6 or FIG. 11) reports to the controlling program that the position is more or less retracted than it (they) should be (compared to the script or other position source being used) with said retraction being potentially reflective of the positions of these joint-control points "riding up" due to the impact and calculated-offset back-tension process (which, in addition to it's primary purposes, eliminates slack), the assistive clothing software responds with automatic adjustment of the equipment. It does so by comfortably and quickly loosening and repositioning the prosthesis during the swing cycle in the gait (while the foot is in the air and, in this example, where the centrifugal force is in favor of the dimension of correction) and/or at times of rest whenever an out-of-position status is so sensed, using the automatic adjustment means (c). This also allows a very firm fit during impact without discomfort because of frequent adjustment releases in non-load portions of a script for that prosthetic (perhaps, in this lower leg example, every 5-10 steps, optionally on every step, based on tightness during the load stroke that was chosen by the user, the tolerance allowed before a correction is required and/or the user's preference). Another benefit is that the prosthesis is aerated while gently stimulating circulation with alternating compression and release. Equally importantly, the prosthesis is kept in perfect position without creating a hot, clamp-on prosthesis that applies the burden of impact on the impact plane of the point of amputation.

It should also be noted that the bending of the knee also minimizes the frequency of such automatic adjustments because, when the knee is bent, the single plane of rotation is enforced on the binders above and below the knee thus enforcing the proper yaw of the binders with respect to the leg while the singular axis of rotation helps enforce the same axis of rotation for the prosthesis thus also helping to enforce the vertical positioning of the inter-controlling assembly.

It is not possible or necessary to catalog all the possible procedures usable with the current invention to effect adjustment of the interdependent and interconnected elements of the assistive clothing. However, the operative elements that most such procedures will use to accomplish specific implementer goals are:

a. the ability to loosen the equipment just prior to the correction to allow repositioning and
b. the ability of one element to move another in that loosened, movable environment using the interconnections between the elements and
c. the ability to know precisely and sensitive to the context of the current action exactly where every joint-control point should be and thus
d. the ability to not only know when an element is out of position (a difference, in this example embodiment, of a joint-control point from a specific script and/or program and
e. the ability to place the equipment in the precise positions that are appropriate (in this example, the scripted positions).

One such example procedure, applicable to a full lower body position adjustment during a walking script, follows: As a user executes a repetitive walking script (as is covered in great detail elsewhere herein), there is a point when a given leg first ceases to be the active foot (the other foot is taking the load from the off-balance human stride and this foot has just lost contact with the ground as it prepares its "free swing" portion of the cycle). At this point the knee is partially bent (which, especially with the optional knee-brace guides shown in FIG. 3A, has a very favorable corrective effect on both the yaw of the limb and the vertical positioning of both the calf and thigh control shells). Also, at this point, centrifugal force is attempting to pull the body control elements apart (a handy thing). Thus, at this instant, by very rapidly expanding the control equipment shells thus releasing most of the shells' grasp on the thigh, lower leg and ankle, the natural correction of yaw and vertical position of the bending knee assembly takes maximum effect while the centrifugal force moves the affected elements as far apart as the tendon positions will permit (and they will permit the joint-control points to be moved only as far as the script allows while "reeling" back in any joint control points that are already too far in that dimension).

Thus, the shells have been snapped to a relaxed position, the above corrective forces and the assistive clothing's natural "make the joint-control positions match the scripted values" logic has returned all the joint-control points below the waist to where they should be via the tendons. With the shells loosened, this pulled the shells to the scripted positions. The shells are then quickly closed to obtain a good grip again (with the reversal of the actuator that expanded them), leaving the lower leg in an adjusted and secure state. This has been a stable process because the user's action, here a walking script, is undisturbed since the scripted positions are the ones attained by the adjustment process. Naturally, these automatic adjustments can even more easily be accomplished when the user is at rest or following an adjustment script specifically written for the purpose.

These same processes can, of course, be used to automatically configure the equipment to a new user. The elements of the current invention can support, for example, a process where the user receives equipment in the mail, connects a cable from processing means to a PC serial port and runs a CD configuration program that prompts for and calculates configuration values as it automatically adjusts the distance between elements (such as by drawing the tendons between them to a comfortable starting tension which moves the elements into a perfect fit and at a proper distance from each other. Also, the shells can be software directed to tighten or loosen (using the aforementioned expansion means) to a comfortable configuration starting position for each joint control element. Using the actuators of FIG. 6, the power of each actuator can be automatically balanced to the user responsive to software. In addition to the above, many of the parts have Velcro hinged or closed elements that allow further flexibility in body size etc. thus providing a means to use more standardized parts that are automatically configurable.

Second Means: By creating a means to avoid contact with rotation points such as those over the joint itself by managing it from three or more points (in 3-dimensional joints, 2 in 2-D) on a control plane representative of the joint's attitude but not from points on that control plane. Instead, that control plane is managed from significantly above and/or below the control plane and the joint it controls. This allows programmatically-driven, self-adjustable prosthesis embodiments that don't attach to the joint at all. In the wrist of FIG. 1 for example, although the tendon example used here does touch the wrist, when it is load-bearing and in close contact (such as tendon C as the wrist can be visualized as being pulled by C from the leftmost illustration to the center illustration) it does not rub in contra direction to the joint producing abrasions and heat but "rolls" with the limb much like a ball bearing rolls over surfaces eliminating friction. Using the joint-control processes described further below, this hardware approach can provide, for example, firmer knee support than a typical knee brace with computer-guided positional correction and while leaving the knee itself alone. Similarly, FIG. 3 illustrates a similar arrangement for the ankles.

To additionally maximize comfort, the portions of the tendon that make such contact can be expanded to be broader at contact (and with enough stiffness to spread any pressure over an area wider than the otherwise width of the tendon) and coated with friction-reducing surfaces. Some examples of such additional creature comforts include satin-covered wide-tendon adaptors at contact points and optional low-friction underwear over the contact joint when very heavy and continuous use of the joint makes that advantageous. Typically, a joint, like our example in FIG. 1, should require none of the above because of the lack of rub in the design. However, a satin covered, laterally-supportive expansion of width such as a twist-resistant ribbon near the contact points on each tendon (of as much as ¾ inch at the contact point rapidly tapering to standard tendon width at the first point that tendon retraction equipment requires a narrow tendon to gain entry into the housing) is advantageous.

Third Means: By creating programmatically and/or through special devices a significant, predictable, optionally action-context-sensitive, and relationship balanced set of forces that provide:

a. immediate pre-equipment-response resistance to destabilizing forces (such as a bump from a passerby that would otherwise permit more destabilization until the next adjustment cycle) and additionally
b. control joint slip and provide repeatable precision even in joints with some natural "give"

c. allow the use of flexible, more body-friendly parts (even some with imbedded elastics) such as tendons since, while in active use, the body parts have their elasticity already committed to this calculated pressure.

This third means is more complex than it seems. Some combination of all or some of the following can play an important role in making it practical and accurate:
a. auto-configuration logic and sessions
b. distribution curves
c. equations
d. special sensors
e. tabular data applicable to each joint Actually, applying the strong, balanced control pressures required for means 1 and 2 just above wouldn't be much of a production if a wrist really was a ball joint and if every human joint wasn't a little different from every other joint (or even if equivalent joints on the same person were the same) and if the wrist was always at a perfectly straight position (as in the center illustration in FIG. 1) such that 10 pounds of pull on tendon A would exactly offset 10 pounds of pull on tendon C. But none of those conditions are true and the oversimplification of assuming otherwise would result in a prosthesis that required much custom fitting and vibrated from unbalanced offsets and that would arrive at positions out of precision with those instructed by the processing means. Also, an approach assuming equal offsets to diametrically opposed quadrant-separated tendons wouldn't work on a 3 tendon based prosthesis which, in some applications can be the most efficient embodiment of the current invention.

Another calculation means, however, along with the concept of over-pressurized, geometrically-offsetting, grasping adjustments, delivers the desired results. This additional calculation means and optional devices are dedicated to arriving at the perfect amount of pressure to apply on each joint-control point which may never be the same numerical amount even where there are only two diametrically opposed, mutually offsetting tendons involved as in the example with tendons A and B above. If the wrist were a ball joint and if there was only one joint-type to develop an unique solution for (and each joint-type weren't different in different people), it is certainly true that you could easily develop simple vector triangulation based calculations and use these (or tables compiled from an array of these calculations over the range of use) to convert a standard back-pressure value desired for a joint into one that will typically be different for each tendon for the joint based on the attitude of the joint. Even though the wrist isn't a ball joint, etc., this is still a workable embodiment of the current invention but another approach considered here does a better job.

The auto-adjustable capabilities of the current invention provide a simpler and more precise approach that is even responsive to tiny changes in the body and slight mis-positioning of the prosthesis. For an example of one means to make the tuning calculation (there will be many other obvious calculations), assume a 4 tendon joint and a servo or stepper based actuator system, here driving tendons, and the relative positions of the center example of FIG. 1. The processing means, as part of an automatic configuration tuning process (this is one of several such automatic adjustments the rest of which are considered separately), using means 1 and 2 just above and the joint-control processed described further below, directs the positioning of the wrist to each possible position for the joint (or representative positions between which it can easily extrapolate results) when the equipment is actually on the user.

A table coordinate-based structure is used here as an example of one calculation and one data format for the storage of the resulting data applicable to the current invention. Again, though more efficient and rapidly accessed data formats exist and are applicable to the current invention, the Dbase format is used in this example for its well-known syntax for ease of communication of the process.

Resistance.dbf: Fields:

Tendon1—the numeric address of a particular tendon such as 1 for tendon A in this example T1Position—a numeric value reflective of a tendon (or other actuation means) position for the first tendon (denominated by degrees, radians, stepper positions, tendon actuator positions, etc.).

T1Ratio—a + or − numeric with decimal places both for precision and to accommodate reducing fractions reflective of the number which you would multiply against any desired general tension amount to arrive at the ideal tension amount for this particular tendon or actuator.

T2Position
T2Ratio
T3Position
T3Ratio
T4Position
T4Ratio

Note there are no fields named Tendon2, Tendon3 or Tendon4 to store their device numbers. First of all, it is a simple matter for the program to know which tendons oppose which tendons (which relatively small amount of data may be in the form of an obvious table, array, etc.) and it is, thus, good data normalization not to waste the space in a large record table recording the same known number hundreds of times. Also, it simplifies indexing and speeds up searches. Other embodiments will have a different number of fields. For example, in 3 tendon system the other 2 tendons share the opposition to any given Tendon and there is not a $4^{th}$ tendon to track.

Also, both in data capture and data processing where multiple tendons are being considered, T1 is always software selected to be the one (for the tendon set for a joint being considered) with the lowest device number, T2 the second lowest and T3, etc. where present, the next and so on. This reduces the amount of data storage by providing a form with no required redundancy, eliminates confusion in testing as well as eliminates the need for multiple index searches to consider any and all combinations of tendon data.

An index is created in the order (ignoring string conversions for numerics):

Tendon1+T1Position+T2Position+T3Position+ T4Position

Thus, to find a record that has been saved that provides all that is needed to know how much to apply to each tendon, all that is required is to do a single seek on a single string made up of the device number of the lowest numbered joint-control position for the joint being considered plus the current position for that tendon plus the current position of the second lowest numbered joint-control point and so on for the third and fourth)

For the moment we are considering and calculating a single coordinate in that system of all possible positions for a joint that processing means has just selected for testing and advanced us to. In this example these retraction values can be integers whose scalar value is reflective of the breadth of one of the stepper or servo motor's micro-steps. Now, at this particular coordinate point in the universe of all possible angles and directions of the joint, we would like to know how to apply a perfectly offsetting force that would not move the joint from it's soon-to-be achieved position but would simply anchor it with calculated tension. Since the geometry of the position will almost always require that no two tendons have the same additive retraction (which is further complicated by the vagaries of the unique joint), this optional form of calculation by testing is a practical means in an effective embodiment to see what that complex set of relationships would actually be.

To accomplish this, a fixed test amount of retraction is applied against each tendon. While this can be the same amount on each and gradually adjusted in a servo-like process towards the best numbers, for more speed, a geometrically calculated or an experiential number (from previous uses) value can be applied initially. The latter is reflected in the above data structure. To test a set of coordinates from that data structure reflecting previous experience, the appropriate record would be located (with an instant seek described with the index above), the fixed test amount for the joint under consideration simultaneously, the equivalent products of those multiplications are applied to each actuator. In other words, we apply a group of back-pressures relative to the current wrist position that worked last time. Now, the position is checked again. If the assembly moved towards tendon A (still using FIG. 1), for example, then the value for its ratio (T1Ratio) was too large relative to it's opposition (here T3Ratio for tendon C) which was too small. Thus, an adjustment is due and it is obviously directly proportional to the amount of movement during the timeslice of the test. A decreasing adjustment is made to T1Ratio and an increasing adjustment is made to T3Ratio. Servo logic for how to rapidly approach the ideal ratio values is not a patentable feature with that kind of algorithm being so common and diverse but, for the sake of a simplified example, one such algorithm for this case would be:

$$NT1Ratio = T1Ratio - (MA*(M/MTP))/2 \text{ and}$$

$$NT3Ratio = T3Ratio + (MA*(M/MTP))/2$$

Where NTxRatio is the new ratio value for joint-control point x. MA=a maximum adjustment amount to be made at one time. This value decreases by 10% if a second pass is required and continues to decrease at that rate for any additional passes required to get a test that produces solid control with no motion caused by the control means and where M is equal to the amount of movement in the timeslice of the test and MTP is the maximum travel of the particular prosthetic device within the breadth of the timeslice used in the test. Similarly, other offsetting joint-control points for the joint are adjusted where necessary and the test is repeated with the adjusted numbers. This process can be completed until the desired degree of stability is accomplished. There are few geometric problems that can't be solved more than one way and there will be many other means of calculating relative forces for the joint-control points useful in applying a strong joint-binding force without affecting the precision of joint placement applicable to the current invention. It will become obvious to implementers that many actuators have a capacity for such minute movement that it is not necessary to test every point in the possible coordinate system. Thus, some embodiments will certainly minimize the number of points and extrapolate on-the-fly (during use). Others will replace test tables completely with alternative calculations to apply the correct tension. A final means of lowering the number of tests is based on selecting a minimum level of precision. Here, rather than setting up a complex system of extrapolation between tested points, the calculation means can, in this example database embodiment, simply "set near on" (a common database term for finding the closest match in an index search) and the record found will be the right record (closest to the position the joint currently holds or is being instructed to achieve) based on the level of precision during tuning which determines how many points you skip between tests in the scan of all possible positions. Also, the tuning process is accelerated not only because historical data started us out near the answer but because, most of the time there will be no change. Of course, if nothing has changed, the old numbers will still work on the first pass and, in the cases of changes, they will be quickly adapted.

Later, when processing means needs to move a joint from one point to another, it
1. finds the conversion data record for the new destination position with a quick seek as illustrated above or otherwise independently calculates the ratio of retention or other means for the calculation of amount of retention for each joint-control point and
2. integrates the new retention values into the scripted values before making its moves. Thus, before any motion is begun, the assistive clothing already knows the exact end position of actuation means desired which already includes automatic balanced retention. Thus, without wobbling, the multiple control points on a joint all move smoothly to a firmly secure position with balanced offset forces already in place.

For example, if
the current joint-control point actuator position is 1100 steps (which includes 7 micro-steps of current control tension i.e. the scripted position is 1107) (the current control tension is not needed for solving the example equation below) and
the new joint-control point desired is at 1110 steps (more retracted than 1100 in this example embodiment) and
the Resistance.dbf record retrieved via the indexed table or other calculation means said that, at that joint attitude, that joint-control point's Ratio was 0.85 and
The current desired resistance for the joint under consideration is 10 (micro-steps in this example) (CurrDesiredResistance is a stored, calculated and/or table based value that can be unique to each joint and even unique to the current application since different operations require different levels of control on different joints) then
The new current desired relative resistance for that joint is 10*0.85 rounded to 9 micro-steps thus
rather than advancing to the desired point and then tacking on a time consuming and potentially direction reversing additive control retention action, actuation means will simply advance the actuator 13 micro-steps to the position 1113 if the following always-positive-retention example formula is used:

$$\text{Advance} = NewPosition - CurrPosition +$$
$$Round(CurrDesiredResistance * Ratio)$$
$$\text{thus:}$$
$$= 1110 - 1100 + Round(10*.85)$$
$$= 13$$

Then, optionally, between cycles, the processing means can check for movement after the advance is made to the desired position. If any of the joint-control points for the joint are not where they should be, then, using the same logic as at the time of initial tuning above, a recalculation of an improved set of ratios is completed and saved in the table (or other means) by processing means for that joint. While an immediate position correction could be made at this point, the next cycle will correct it anyway. However, the fact that we have a means to automatically refine the data we use while the process is being used provides a useful tool in maintaining precision in prosthesis control even as it is being used (which is when they typically get out of alignment).

Hydraulic and other pressure-based actuators have commonly known means to achieve a given position and sustain it until the next instruction. In a hydraulically based system, as in the above stepper or servo-based example, once the position is achieved in the tuning process, the estimated retention pressure for each joint-control point can be applied and the position sensing means queried for any change in position hoping for none and adjusting for any that exists and saving the results in Resistance.dbf Later, when following a script and desiring to go to a position, that information (the grasping pressure indicated by the TxRatio field in the retrieved Resistance.dbf table against the separately stored general resistance desired for that joint in the current activity) is used by hydraulic or other pressure-based means to rapidly acquire the desired position and maintain a pressure in excess of the pressure required to maintain position in the amount of that multiple-control-point balanced grasping pressure.

Though the above illustrations, which are only a few of the many calculations and procedures to provide balanced grasping pressure applicable to the current invention, are extensive and extremely tedious to document, they execute quickly and provide a foundation that supports a wide range of precision enforcing and automatic adjusting features in a comfortable prosthetic.

The joint-geometry "scanned positions" calculation approach above also allows the equipment to self-adapt to abnormal or injury-caused changes in joint geometry.

The process for data capture is congruent to and accomplished in combination with the foundational patent "Natural Robot Control" Ser. No. 09/960,294 by John Simmons and the provisional application that preceded it, 60/234,191. To relate the data capture process of the current invention to the foundational patent, it is useful to think of the referenced patent's "local" data capture of it's user modeled actions as the action modeling session that is recorded in the current invention since essentially the same process occurs in the current invention except that, instead of the local processing means transmitting KCM's (the Key Control Measures described in the referenced patent) to the remote, these KCM'S stop short of transmission and are stored in local memory as steps, tiny timeslices of full body, simultaneous movements. Similarly, references in the referenced patent to information received by the remote and what was done with it relate directly to the user of the current invention who "receives" data from a previously modeled session and recognizes and responds to deviations between the current and recorded positions.

As in, say a 10 pound vertical equivalent force, is multiplied by the ratio value for each tendon on the joint and then, the foundational patent, each relevant control point of each relevant joint can provide positional data to processing means. This can be done by using commercial actuators that automatically return data that can be stored as or converted into positional data using commonly used techniques. Positional data can alternatively or additively be captured by separate position sensors connected to the joint, the actuator, or, in embodiments using tendons, to tendons. There are, in fact, embodiments of the current invention where simple bend sticks (usually a thin flexible plastic strip that returns bend angle data) is all that is needed and can be placed over the appropriate points of a joint. In the example embodiment that is best reflected in the figures, where tendons (similar to those in FIG. 11) are used, the tendon actuators themselves are shown with position counters with serial output to the processing means.

Similarly, and optionally, joint pressure information may be captured by the actuator, pressure sensors at contact points, up-line hydraulic points (such as the "high-side" or provided pressure of the pressure control means common in hydraulically-based actuator systems), etc. This is useful for several applications of the current invention. Since many of the actuators illustrated with figures in this sample embodiment are hydraulic, that pressure is described here as sensed at the pressure controller as the pressure required to achieve or maintain the position currently maintained. However, any commercial pressure sensing means applicable to capturing joint control-point pressure is applicable.

Also, the attitudes of the user's body and limbs are monitored using attitude, accelerometer, positional and/or motion sensors. The general attitude sensing equipment could be placed almost anywhere on the body measuring it's vertical or tilted position. The other joints, because they are all in sync with the area of the body whose attitudes and position is thus measured, will thus be in a directly related position calculable by combining the effects of the angles of the connected joints. However, by wisely placing sensors, such down-the-limb position calculations can be kept to a minimum or eliminated altogether. The primary attitude and acceleration sensors in this particular sample embodiment of the current invention are on the lower back near the waist. Optional head and leg sensors are also very useful as will be seen below.

Figure 2:
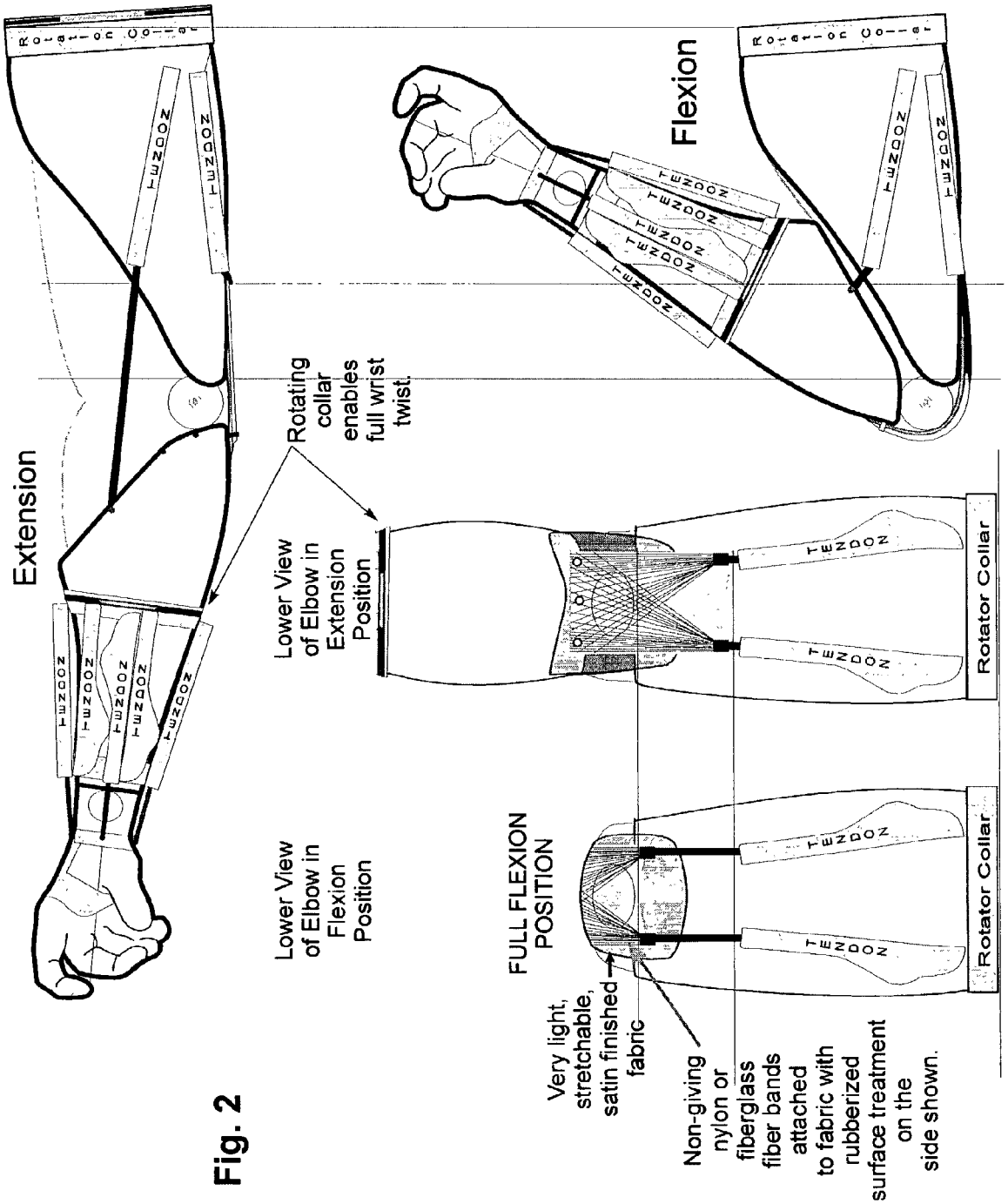
FIG. 2 illustrates actuator-driven external body equipment for the arm.

The angle scalar number reflecting the angle of joint flexion or extension is not necessarily a geometric angle. For example, when complex, multi-axial joints (considered further below) are controlled by multiple actuators as shown in FIGS. 1-3, it is fast, convenient and extremely efficient in terms of data volume and processing time to simply pass the actuator positions rather than the complex joint angles thus created. Thus the system can be configured to simply respond by making the local or remote actuator reflect the appropriately corresponding actuator position at the other end rather than being concerned with the complex angle attained. In this sample embodiment with its predominant illustrations of pulling actuators, we will illustrate the transmission of the amount of actuator retraction for each local cable as read in the actuator of FIG. 12. Additionally, although not illustrated in the examples, commercial joint angle sensors may be placed at the joints themselves relaying the current angle information to the processing means to provide additive or alternative position sensing relative to joint control points.

Distance sensors also make a substantial contribution to walking control by sensing obstructions, irregular terrain, steps, etc. and supporting the automatic responses to easily walk around or over them. While they can be mounted anywhere, they can be particularly useful on the feet including those facing ahead and behind the foot. Where the speed of the foot and/or the slowness of the particular sensor used by implementers requires it, these can be placed in angularly separated arrays to share the load of picking up distance points. Foot mounted accelerometers are also useful as a fallback where an impediment is not sensed in advance by distance sensors but is encountered by a foot in that they provide a stub indication before an imbalance has yet occurred enabling a slightly faster automatic response.

In addition to sampling and recording position, attitude, motion and pressure for any joints and thus any limbs and the body as a whole, the technology of the current invention, like the local and remote units of the foundational patent, can physically control any or all body joints and limbs with or without the cooperation of existing muscles or other joint control devices.

Position Achievement Techniques: As shown in "Parallel Processing Embodiment" (in the provisional patent 60/234, 191), in each cycle of phases (each frame as applied to this application) and over multiple cycles the current invention can continually approach the desired position. The local user of the original provisional patent is comparable to the user in this application. The recorded "correct" positions here are comparable to the original invention's remote data. In each application, the user equipment attempts to emulate the positions of the other dataset within controlled parameters. While it is not a necessary function for the current invention, the back pressure resistance or some fraction of it can be applied to the user equipment as in the original provisional patent to allow the user to bear at least a portion of the burden for computer aided therapeutic exercise, virtual reality training or entertainment. Those recorded values along with the adjustment variables adjust the way the user equipment follows the script by including these adjustment amounts in the calculation of the targeted positions for each joint. This process may be viewed such that in each frame the equipment achieves the desired positions before moving to the next frame. In fact, with adequately responsive equipment, this is a reality. This is especially realistic when considering that this application is favorable to the actuators being high-speed stepper motor-based actuators (since emulation of position, not pressure is the key element). Still, to accommodate less responsive equipment or especially short frames (a frame is usually associated with a specific period of time referred to as a time slice) an approach not unlike that used for parallel processing in the original patent is optional. There, multiple intra-frame adjustments and, where necessary (when catching up in the next frame is necessary due to equipment slowness) inter-frame adjustments can be made as the equipment continually approaches the target. In the discussion of adjustments that follow, we will use the fully achieved angle within the frame period assumption.

Examples are given here of sample joints and limbs to disclose the underlying process for effecting this. The user wears equipment (some example embodiments are shown in FIGS. 1-7) designed to sense and record the position of, programmatically reposition each of a user's joints, and, optionally, apply response pressure to, as directed by processing means based on positions and actions that come from data reflective of local conditions, a current person's actions, previous recordings of a person's actions, purely programmatic strings of instructions or a hybrid composed of previously modeled action scripts programmatically blended/morphed into a fluid set of joint instructions responsive to scripted actions.

To provide the power behind the joint movement, there are numerous commercial actuators from stepper motors to artificial hydraulic muscles that contract when inflated to effect changes and provide support to these joint angles. These and any other effective actuator means can be programmatically controlled to work in the context of the current invention. For example some or all of the tendons shown in FIG. 3 could be replaced by a commercially available hydraulically controlled contracting/expanding muscle acting as a tendon in place of the tendon actuators and tendon cables shown. In these examples, however, for the sake of example, a hydraulic tendon-based, offsetting pull only system using gas or fluid pressure has been described as well as an alternative stepper motor-based actuator. For a better description of the particular illustration of a tendon actuator used in this example embodiment, see FIG. 11 for hydraulic and FIG. 6 for one embodiment of a stepper actuator (of course, the more typical, basic stepper motor is also applicable). In the hydraulic example, the tendon, or cable, is "pulled" as the hydraulic piston causes the gear to rotate. For an example of their use providing offsetting tension to achieve human-like joint control, see FIGS. 1-4. Different actuator mechanisms have different strengths and may, for example, suggest for many applications stepper motor based, artificial muscle technologies or magnetic-induction-based, etc. actuators to perform the same functions. In other embodiments of the current invention, these or any alternative means of actuation can be applied to push or pull a tendon or to push and/or pull directly on an external joint control mechanism. FIGS. 4 and 5 (best seen in FIG. 5) even illustrate the applicability of screw-based actuators.

Another actuator innovation applied towards getting more work done with lighter and smaller actuators is the enhanced strong-side-biased actuator described above. Robotics designers will normally install, for example, an actuator rated in excess of the maximum load for the task to be done. One embodiment of the enhanced strong-side bias actuator shown in FIG. 6 is used in the example illustrated in FIG. 3A's anterior lower thigh actuator (enlarged at left with a front view of the knee cover and actuator array including 4 strong-side-biased actuators). It replaces the bulky, heavy and hard to hide high-capacity actuator that would otherwise be required with a thin array of 4 flatter tubes (each containing, in this example, 4 motors) that are embedded in the thigh shell for stability and to help conceal them under clothing. Using the ultra-light design of FIG. 6, each individual motor only has to be rated such that it provides 3 or 4 percent of the total force required to be applied to the joint thus allowing the use of smaller, lighter and more efficient actuators.

There are numerous well-known programmatic and equipment means by which the actuator can be controlled to quickly move the joint to the desired angle and monitor/assume a maintenance position. It is not important which available or new technology is used to assure that the actuator arrives at the desired position at the desired time. The foundational patent "Natural Robot Control" goes into great detail regarding optional aggressiveness options which can also be used in the current invention. However, since many of the pre-modeled scripts should be followed fairly strictly for many applications, it is completely acceptable for those applications to use a 100% aggressiveness option where the actuator is simply instructed to move to the joint-control point to a given point immediately (which can be particularly gentle remembering that the number of timeslices/data records used to move a joint from point A to point B ultimately determines the speed and smoothness) as long as safety measures are in place for exceptions. For example, options for maximum pressure to be applied to a joint-control point can be set low enough to prevent injury and can be context sensitive to the script or even the point in the script being used (special device parameter controlling records in the regular script are discussed with the sample data formats below and, by referencing a pressure sensor with a device number in that structure, one effective means to control safe amounts of force in a completely context sensitive way is illustrated). Where pressure applied options are discussed, it should be noted that non-pressure-based actuation means (such as stepper motors) perform advance-until-reached actuation where the point being "reached" can reflect both pressure and position where pressure is desired as in the discussion of grasping retention pressures above. Thus, in one embodiment, it would seek a position until the "safe" limit pressure had been reached according to pressure sensing means.

Another safety factor comes in the form of an alternative procedure particularly applicable to some rehabilitation support and physical therapy applications. Here the processing means instructs the actuator to simply apply a given or norm-limited pressure to the joint-control points that the script indicates need to move thus merely massaging towards a desired, scripted position without actually forcing the user's initially stiff joints into the position ultimately desired. This software directed alternative process allows the first moments of an assistive clothing driven physical therapy session to limit and meter over time the amount of force applied in attempting to move joints to accommodate the gradual loosening of the joints early in the session. By monitoring the angles so achieved, the software can easily ascertain if the joint(s) being worked have reached the script's desired angle with the "honeymoon" pressures and, if not, gently, over time increase the pressure applied until the script's desired positions are achieved with tolerable pressures. Again, the imbedded device parameters provided in the sample data structure are a useful means for identifying joint specific acceptable pressure ranges and even providing acceptable joint pressure ranges within a given point in a special loosening up workout.

Of course, a user could start with a warm-up script and then user-select a tougher one but, the current invention also accommodates the ability to use only one script for such a workout that gradually achieves full aggressiveness based on the patient's actual joint mobility and even his real-time personal preference so that multiple scripts and frequent user intervention are not required. This is more than adequate for most applications and eliminates the need for special warm-up scripts. Here, the processing software following a normal script recognizes a notable difference in actuator or joint-control point pressure as compared to the pressure recalled from the modeling session. Alternatively, the software simply compares current pressures encountered with established norms which can also be joint-control-point specific. By multiplying these norms and/or script-provided device pressure values by a conversion factor that can be changed by the user during the session, we allow the user to gradually "turn the heat up or down" through the user control means described later so that the normal script is both sensitive to the user's joint stiffness/mobility and the user's direction. Because the user can start, stop and guide each such session, many users will be able to initiate and monitor their own physical therapy sessions when guided by and protected from injury by assistive clothing.

Pressure administration by an actuator, at first glance, seems to imply the need to use hydraulic actuators that function with pressure. This does work nicely since the pressure in the hydraulic actuator is directly proportional in an easily calculable means to the pressure on the joint-control point. However, pressure against a resistive or burdened joint can also be easily achieved and applied with any number of other actuator technologies. Even a hard-positioned stepper motor can be advanced in tiny increments against a resisting joint until the pressure sensing means monitored by the processing means registers the desired pressure whose range is not absolute or square-wave responsive because of the slight flexibility of the human body and, optionally, of elements in the line of force such as springs or minutely tensionable tendons. Those additional elements would probably never be needed for mitigation of a square wave force where a lesser force denominated by pressure is desired when a human limb is the object of the control because of the slight flexibility of the human body and the tiny potential advances of stepper motors. However, for example, a steel knee joint in a full-leg prosthesis, will benefit from it and will not suffer from "slack" in control tendons, for example, because of continuous grasping back-pressure described above.

One example of a database structure applicable to the current invention is outlined below.

The first table is named Actions.dbf and, contains the following fields.

Actions.dbf:
ActionName Character field of 40 character length for the ease of documentation.
Example: "StandingErectFromErectSeatedPosition"
ActionType 1 character alpha.
Examples:
A (for action). This type of record will have many related records in the Positions.dbf table described below. Each of those related records will be used to create multiple, sequential motions in tiny timeslices to achieve smooth motion as choreographed by the action cataloger.
P (for position). This type of record will typically only have one related record in the Positions.dbf table described below for each joint. That related record will store the precise joint-control point position and other optional information for each joint when the user is in the position described in the ActionName above. An example would be an ActionName of "PositionSeatedErect", an action type of P and a record in the Positions.dbf table below for the singular position and joint condition of each joint when the wearer of the local equipment is in that specific PositionSeatedErect position. There can be any number of such standard positions since their full attributes have been reduced to a simple database table.
ActionCode A numeric field of 4 integer positions with a maximum of 9999 possible numbers
Example: 0001
TimeSlice A numeric field of 7 positions including 3 decimals (ex: 1234567 interpreted as 1234.567). 3 point decimal is assumed so the decimal point doesn't take up a database space. However, it is displayed in examples below with the decimal place for clarity. This is, essentially, the MDI. This determines the length of the timeslice in which we measure the movement of each joint. Naturally, the more rapid or intense the movement of the action being captured, the smaller the timeslice to provide fluidity in motion.
Example: 10.00000 (here in milliseconds this makes a timeslice $1/100^{th}$ of a second). It is possible to change this value during the execution of the action by adding a field to the positions.dbf table below and responding to it but that is not fleshed out in this sample embodiment. Of course, groups of actions could also be grouped together into a single by-reference Action allowing very long combinations of actions with a single "handle" or command.

There is a "1 to many" relationship between this table and the one below. That is, for each record in the table above, there can be many in the table below.

The second table is named Positions.dbf and contains the following fields:
Positions.dbf:
ActionCode As above. This is the key field that relates the two databases. Each of the records in this table is related to a record in the above table based on this key field.
JointNum A numeric field of 4 integer positions. For joints with x dimensions there will be x records for each affected timeslice. For example, for a joint controlled from 4 points (like 4 stepper motors or 4 tendons), that joint would have 4

JointNums, one for each tendon or other actuator contact point (joint-control point), that are referenced independently.

SeqNum A numeric field of 5 positions, all integer.
Example: 00001

NewPosition A numeric field of 6 positions including 3 decimals (ex: 123456 which is interpreted as 123.456).
Example: 179.801 or just under 180 degrees. Geometric degrees are used here for simplicity. In practice, applications engineers may instead use the equipment's minimum graduated position measure.

Pressure (Optional.) A numeric field of 8 positions. In situations where carry payloads are substantial or sudden, athletic movement is required that would require a sudden change in pressure in excess of what the equipment would normally exert to achieve the position required in the timeslice allowed or in cases where the action is so delicate that less than the normal position acquisition pressure is required and to fine tune equipment for the special body characteristics of the end user, this field may be populated so that the equipment will immediately exert the appropriate additive force on this joint within each tiny timeslice. This value may be automatically calculated in a variety of ways. Values may be created programmatically based on joint specific experience based algorithms helpful to providing response. They may also be programmatically responsive to body worn sensors on the action cataloger, body weight and the rate of positional change between this and the preceding motion. Or, more simply and most powerfully (and as discussed in this sample embodiment) these values may be left blank when the action cataloger first creates the action sequence. Then, when the equipment is being worn by the ultimate user (in this example a paraplegic), the software will note when a joint does not achieve the desired position in the desired time or when it exceeds it or when the position is simply not achieved due to resistance and insert a programmatically calculated higher or lower pressure figure based on degree of shortfall/overkill to be used the next time. This experience based number will make it work better the next time. The next time the action is executed, it will tune itself even more finely to the limitations and special needs of the user. Thus the system will fine-tune itself automatically to learn each action on each specific user and even adjust as they lose or gain weight or their mobility increases or decreases.

Misc Used by various programs such as those who monitor attitude, pressure, etc. and determine the responses to conditions in or outside a range to, for example, recognize an out-of-balance condition or a muscle spasm (excessive pressure on a joint).

It should be noted that the Positions table is also used to store other key data besides the above described applications. Examples below show that additional storage as additional records. It is, of course, also a practical embodiment to add fields to the positions table for the expanded data allowing that data to "ride" on records already created to contain joint positional data.

Examples:
1. Joint Angle Sensors. While joint angle can be measured by gear position or other actuator specific positional measure, it is advantageous in some applications to also have joint mounted angle position sensors to report back to the processor. For these applications, fields may have alternative values:
   a. Action Code: (same) Links this as something to be done along with other steps in this action.
   b. Joint Number: Here it is a unique device number separate from the also numbered joint. The device, of course, is the sensor.
   c. Sequence Number: (same) this keeps all forms of measurement in sync.
   d. New Position: Similar. This is the joint angle but as measured by the additional sensor.
   e. Pressure: (not used)
2. Pressure and Impact Sensors. For some applications numbered joint or limb pressure sensors are added. While pressure is known by the pressure controller as back pressure, increased speed and accuracy can both be accomplished by the addition of joint mounted pressure sensors.
   Alternative values are:
   a. Action Code: (same)
   b. Joint Number: Here it's a unique pressure sensing device number separate from the also numbered joint. The device, of course, is the pressure sensor.
   c. Sequence Number: (same) this keeps all forms of measurement in sync.
   f. New Position: (not used)
   g. Pressure: Same but as measured by the additional device.
   Some pressure sensors aren't mounted on joints and some aren't as interested in pressure as in contact or the lack thereof. One example is the front and rear ball mounted pressure sensors on the sole of the foot. These record for each sequence number (timeslice) the pressure on that point on the sole of the foot. Another form of pressure related sensor is the "tickle"/minor impact sensors made optionally for any part of the body but particularly for the fingertips. All can store their data in each timeslice where they have activity in this format as and additional Position record.
3. Attitude Sensors: Pitch, roll, vector of motion and vector speed are important measures for balancing physically assisted users, remote robots (particularly when transmissions are slow and balance needs to be maintained between communications) and full motion support mechanisms, etc.) These are also useful for every change of their value that occurs in a timeslice of the action being processed.
   a. Action Code: (same)
   b. Joint Number: Here its a unique device number for the attitude sensor like 9991.
   c. Sequence Number: (same) this keeps all forms of measurement in sync.
   d. New Position: The first 3 characters are pitch degrees. The second 3 are Roll degrees. Example: 090359 for 90 degrees of pitch and 359 degres of roll
   e. Pressure: The first 3 characters are for vector of motion and the other 5 are speed along that vector eg: 01000170 for 0010 degrees vector (yaw) which may always be measured as degrees of change in yaw since the last timeslice making mixing and matching of stored actions simpler. The 0017.0 (the decimal is implied) is the speed along the vector.
4. Distance Sensors: Body mounted distance sensors are also optionally worn to measure the anticipated distance to an object. When the distance sensor is foot mounted (and an array of them can be ideal to gain more data in less time), this is extremely useful in anticipating a rock or hole in the road before contact is made by switching to a "high stepping" procedure from a normal walking procedure in progress or simply raising the foot until the distance meets or exceeds the recorded value. The sensors are also extremely useful, for example, in recording how far the glass that the action cataloger is picking up is from the hand at each timeslice. Then, if the user was a little too close when initiating the pickup, the software can stop just a fraction of an inch prior to contact and allow the user to adjust with touches on the oral keyboard. More sophisticated software can actually use 3 triangulation aligned or 2 strategically aligned distance sensors to actually home in on the target once it is very close. Thus the distance sensors can actually make quickly grasping objects a smooth process and help navigate rough terrain.
   a. Action Code: (same)
   b. Joint Number: Here it's a unique device number for the distance sensor like 8880.
   c. Sequence Number: (same) this keeps all forms of measurement in sync.
   e. New Position: Distance to the object in this timeslice (driven by sequence number).
   e. Pressure: Used for advanced sensitivity measures. The first 4 characters are for relative velocity of the target and the last 4 is the acceptable range of error. The acceptable range of error can be programmatically defaulted or selected for an action as a whole by the action cataloger. Also, after the capture of the action data, the cataloger can fine-tune the process by overriding the defaults where appropriate by manually entering tolerances. Also, tuning software can be developed simply to tune certain kinds of actions (like walking, stooping, sitting, etc.) by modifying these and other values after the action is initially captured.
5. Milemarker positions. Manually or programmatically entered milemarker positions are optionally added to record the exact position in the "stroke" of a repetitive recorded cyclical script as described further below. It allows the program to know, particularly when switching from one script to another mid-action, where to pick up in the new script. Regardless of how many joints and other devices are being monitored, there is typically only one milemarker record per sequence number in an action sequence (script).
   a. Action Code: (same)
   b. Joint Number: (1000 to identify this as a milemarker record)
   c. Sequence Number: (same) this keeps all forms of measurement in sync.
   f. New Position: (unused)
   e. Pressure: Used here to identify the percentage of progress towards the end of the stroke. Example 07701 interpreted with assumed 2 point decimal as 77.01 percent. The other 3 characters are available for other use.
6. Landing Zone Attitude. During action cataloging, the cataloging software calculates the attitude of the landing zone as described in "Landing Zone Pre-calculation" further below
   a. Action Code: (same)
   b. Joint Number: (1001 to identify this as a landing zone attitude record)
   c. Sequence Number: (same) this keeps all forms of measurement in sync. While there are only 2 of these per cycle in repetitive walking sequences, they must have a sequence number to be found and it can be the next available sequence number for the action at the point when the landing zone has been scanned by the foot sensors as described later.
   New Position: Used here to identify: Pitch.
      Example −020.01 for a negative pitch of 20.01 degrees
   e. Pressure: Used here to identify: Roll and Distance (from a central point in the scanned area).
      Example −1412073 for a negative roll of 141.2 degrees and 7.3 cm distance to the landing zone.

The Action Cataloging Process:

To create a script, an action cataloger, like the local user of the referenced provisional patent "Virtual Robot Control", 60/234,191, wears equipment capable of sensing every joint position in all needed dimensions operating in relatively short slices of time (timeslices) while operatively connected to processing means which captures these positions over time. The database structure above is an example of one format for storing that information. In an example of an action cataloging session, the action cataloger may first create a standard body position by sitting in a common, frequently used standard position whose ActionName field in Actions.dbf might be titled "PositionSittingErect" and it's numeric equivalent could be chosen as 71 as shown in the table further below. This is reduced to a single record in Actions.dbf and there is one record for each joint-control point in Positions.dbf to define the position of every joint-control position for that seated position. The action cataloger or an assistant can create such a standard position by, first, filling in the fields of a record for the Actions.dbf table. This can be done by any data entry means. A sample code segment below illustrates a simplified data capture program that captures the user entered setup information stored in Actions.dbf and then captures device positions in the data structure above as the action cataloger models the actions to be captured. For slow computers or short TimeSlices, machine language subroutines are optional code replacements for the sake of speed. However, this familiar Dbase/Foxpro sample snippet is easy to read and understand and much of the speed comes from the independent peripherals that feed a program like the one below. For example, an independent processor (or multiple independent processors) polling every joint sensor feeds a quickly read buffer that populates the array FilledArray with joint position data when the FillArray procedure is called. For even greater speed, the array can be continuously fed by a faster low-level code program (assembler, C++, etc.) so that the data is already in array form when it is needed to allow shorter TimeSlices on slower machines.

---

Example Script Capture Snippet

```
Set typeahead to 1           && used in a later example of "bumping" adjustments
@1, 1 say "Enter the name of the script" Get AN
@2, 1 say "Enter Type                 " Get AT
@3, 1 say "Enter number of script     " Get AC
@4, 1 say "Enter Timeslice            " Get TS    && In milliseconds
@5, 1 say "Enter Special Code         " Get S
@7, 1 say "Touch enter to begin data cataloging session" Get Ans
Read
Use Actions
Append Blank
Replace ActionName with AN, ActionType with AT
Replace ActionCode with AC,Timeslice with TS, Special with S
Select 0
Use Positions
```

-continued

```
Processing = .t.
NextTime = GetTime( ) + TimeSlice && GetTime( ) gets current time in milliseconds
Seq = 1
On Key Label F12 Processing = .F. && When F12 is pressed, script finishes&exits loop
Do while Processing
    Do while GetTime( ) < NextTime
        Do FillArray    && Gathers current joint positions from controller buffer into array
    EndDo
    I=1: Z=Alen(FilledArray)    && Z = number of joint-control points polled
    Do while I <= Z             && For each joint polled (all polled in this example)
                                && Save data records----v
        If inkey( ) = 134       && if user is holding F12 key to flag this as "bumpable"
            Misc=allt(Misc)+"B" && used in joint "bumping" procedures explained in
        Endif                   && a later example. "B" indicates a bump record.
        Insert into Positions(ActionCode,JointNum, SeqNum,NewPosition,
            Pressure, Misc);
        Values (AC,Seq,FilledArray(I,1),FilledArray(I,2), FilledArray(I,3),FilledArray(I,4))
        I = I + 1
    EndDo
    Seq = Seq + 1
    NextTime = NextTime + TimeSlice
EndDo
```

It is true that anything that can be scripted can also be accomplished programmatically by effecting the same actions that the script directs from programmatic instructions, algorithms and calculations with or without the aid of computer models and simulations. The skilled user in the field will observe the recorded body kinetics that are turned into fluid human action and effective user control by the current invention and develop programmatic replacements for some or all of the scripts while remaining true to the full concept, apparatus and methods of the current invention.

To continue the example, with this foundational data keyed in, the action cataloger assumes a standard, erect, seated position. The following table is created as the processing means polls the position of the following joints. For the sake of simplicity we will consider only 4 joint-control positions on a single joint performing this singular position assumption operation which results in 4 records in the Positions.dbf database table (the 5$^{th}$ and 6$^{th}$ have additional functionality as explained below).
Positions.dbf:

| ActionCode | JointNum | SeqNum | NewPosition | Pressure |
|---|---|---|---|---|
| 71 | 551 | 1 | 179.000000 | |
| 71 | 552 | 1 | 201.000000 | |
| 71 | 553 | 1 | 184.000000 | |
| 71 | 554 | 1 | 201.000000 | |
| 71 | 959 | 1 | 088000 | |
| 71 | 960 | 1 | 089000 | |
| 71 | 971 | 100 | 1 | |

Chart notes: There are, of course, not 554+ joint control positions. This is just a convenient nomenclature protocol where the first two characters identify the joint number (55) and the next character identifies the joint-control point on that joint (1-4) in this example.

Also, the 5$^{th}$ and 6$^{th}$ records have a logical joint number (959 and 960) which are actually devices rather than joint-control points. In this example, they are body attitude sensors indicating, at this particular point in the script (SeqNum), the body attitudes of different parts of the body (here the head, device #959 and the torso, device #960). The action cataloger had pretty good posture since his roll was 000 for both the head and torso located sensors and his pitch was close to 90 degrees. Higher levels of precision may be applicable for some applications in which case the field width for NewPosition will be increased.

Also, the last record has a logical joint number (971) which is actually a flag to the software that the real purpose of this last record is to switch scripts to the Action.dbf record identified by the ActionCode that has been placed in the SeqNumber field (here, 100). When this record is reached, the process will pick up at the first record (since there was a 1 in NewPosition) in Positions.dbf with ActionCode=100 (and SeqNum=1) following criteria set up in the Actions.dbf table record with a 100 in the ActionCode field as will be seen further down in the example. This provides an effective option for linking scripts in sequence.

In this single position example, they all have SeqNum 1 since they all simultaneously move to their assigned positions and since there is only one step (even though the morphing process described in more detail further below actually divides this into many steps).

The above provides means, along with the assistive clothing hardware, to cause a user to assume a position. A next logical step and/or script is to stand up. This will, of course, involve considerably more sequence numbers than the one used here for position assumption. Still, it will be common for many operations, within any given single slice of time, for many joints not to change position and thus require no additional record for that timeslice for those joint-control positions. Thus, as the database is being read and acted upon by the processing means, joints with no records for the sequence number being executed are not moved but their positions are maintained as they were. If, however, special pressure considerations are appropriate even when the joint angle is unchanged, a record will still be created for the sake of storing the appropriate pressure if it is different from the previous SeqNumber.

We now have created our first standard position named PositionSittingErect which, using the current invention's sensing, processing and recording means, has reduced that full body position down to one record in the Actions.dbf table and one record for each joint-control point in the Positions.dbf table.

This process is exceptionally tolerant of differences in chairs used in terms of gaining a still-precise set of body positions to start from. After morphing to a standard sitting position as above, the user's body will be precisely in the pre-modeled attitudes defined by the now phantom chair used by the action modeler whether the chair the user is in now matches it or not. If the modeler's chair was straight backed, (the modeling norm) and the user is currently in a chair with a more reclined position, the earlier position gaining script will now have him sitting more erect having bent his waist with his back which is now touching nothing. In extreme cases, such as a bean-bag chair, the body may have rocked back so far that the attitude sensors will report, for example, pitch readings significantly greater than those in the script. In that case, the processing means software may, for example, be configured to choose and execute a morphed position change script resulting in a more advanced body position and then continuing with a stand-up script that begins from that position. Obviously there are also programmatic processes that can provide similar source instructions to the assistive clothing.

Now, for example, we can create a catalogued procedure to move from such a standard seated position to a standing position. This, of course, can involve hundreds to thousands of steps for each active joint. To show one means for one script to call another, we added a 7th record to the sample just above which identifies the script identified by ActionCode=100 which brings us to the sample script below. Thus the user chose a script that both corrected seating posture to a standardized position and then called the following standing script.

Actions.dbf

| ActionName | ActionType | ActionCode | TimeSlice |
|---|---|---|---|
| StandingFromSittingErect | A | 100 | 20.000 |

Records: 1

The console operator has decided that the minimum timeslice is 20 milliseconds or $\frac{1}{50}^{th}$ of a second. This is because, having gently put the user in the standard seating position, we are ready to move forward with a rapidly responsive script (we won't be waiting 3 seconds to move only ½ millimeter). With the actions.dbf record created for the StandingFromSittingErect action, the action cataloguer now, wearing the equipment, sits while the console operator selects the PositionSeatedErect position from a browse screen of Actions.dbf records and touches a keyboard key to signal execution of the procedure. Reading the Actions.dbf record and the Positions.dbf record just created earlier, the processing means using the means of the current invention as described above to assume the Positions.NewPosition positions recorded for each joint in the Positions.dbf table. The action cataloguer is thus, over a period of 3 seconds, gently moved into the exact position he was in when he created the standardized position even if the chair is somewhat different (since the joints are synchronized to form the body into the precise overall combination of joint positions with or without the exact same contours of the chair).

The console operator now selects from a menu "Capture Actions" and is prompted to select a record from the Actions.dbf table. The operator chooses the StandingFromSittingErect record just created and touches the Capture menu option.

From that point on until the operator selects "End Capture", 50 records per second (based on the TimeSlice selected of 20 milliseconds) are added to the Positions.dbf table for each joint that is active as the action cataloguer stands up (see notes on chart below to see why there aren't four times as many records (i.e. 4 per joint-control point/cycle) for some embodiments such as those using joint-mounted angle sensors.

A sample is shown below but only considers 1 joint for a few of the many cycles. Since it takes about a second to stand up you would expect to have roughly 50 cycles and, thus, about 50 Positions.dbf records per active joint.

In the sample Positions.dbf records below, there are also 3 odd entries with G for JointNum and numerical data in NewPosition and Pressure. As might be suspected, these are not joint angles or pressure information but attitude based balancing data. The NewPosition and Pressure numbers are actually attitude measures. In this example embodiment it is the information from a single main torso based sensor recording the erectness of the torso throughout the operation. As will be seen later, when differences from the recorded balance information are sensed by the user, this difference in numbers alerts the system to engage balance controls.

Notes for chart below: It should also be noted that, because of the unique design of the current invention, only one attitude measure is absolutely necessary for the whole body since every joint can be controlled synchronously and in related alignment with every other joint simultaneously such that if one joint's attitude is off, all others are off proportionately after adjustment for inter-script adjustments. However, multiple attitude sensors are useful to simplify calculations and refine precision.

Also, the sample below is an example of a different data storage paradigm for the table Positions.dbf than the sample above which is conducive to embodiments whose means for guiding the joints to a position are not based on incremental actuation means (which easily provide step-based or gear-position-based information) but, instead, measure and control its progress to a joint position by angle sensor's or other angle or attitude sensed related means and thus use actual degrees for NewPosition data. In other embodiments, the measurements could be in radians, percentage of rotation, stepper motor micro-steps (as the example above), etc. Some examples of actuation means particularly benefiting from such an approach are certain pressure-based control means which servo to a given point based on a monitored angle sensor and also human-motor embodiments where all or some of the actuation means comes from stimulation of nerves and/or muscles whose progress must be measured or at least confirmed externally.

In addition to the potential application-based control advantages of the alternative actuation means and sensors, one economy that can be seen in this compatible data storage approach is that, for a 4 control-point joint, only two records per timeslice need to be recorded—one for each primary plane of motion. For example, on the wrist of FIG. 1 tendon A and C control motion along the plane of the paper whose positions can be expressed as angles in the x and y axes within that plane while tendons B and D control the plane perpendicular to the paper and dividing the joint evenly whose positions can be expressed as angles in the y and z axes. Thus, a twist-insensitive external bend-strip angle sensor, for example, on the back of the wrist (to measure the angle of advancement caused by A and C) and another on one side of the wrist (to measure the angle of advancement caused by B and D) will report data that can be interpreted as or into angles taking only 2 records per timeslice for a 3 dimensional joint and 1 record per timeslice for a 2 dimensional joint. More importantly, though, this is illustrative of the support for many alternative actuation and sensing means. The two data storage and actuation means can be mixed and matched on the same user-worn equipment such that some joints could use one approach while others use another for maximum effectiveness. In those cases, processing means makes the obvious conversions (from angles to joint-control positions, etc.).

Also, for the sake of this example, a standing pitch is used such that a perfectly vertical user has a pitch of 90 degrees and a roll of 0. Similarly, a joint at full theoretical flexion (which is different from actual flexion because muscles get in the way of a 0 degree position as flexion approaches) is 0 degrees and full extension is 180 degrees. The theoretical degrees are used here for ease of visual analysis and because it requires no calculated conversion of data when using many at-joint angle sensors.

Finally, in the sample below, a knee joint is considered as two dimensional and thus, as stored in the angle-based data-storage paradigm, has only 1 record per cycle per joint and requires only one angle sensor, which can be a simple "bend-strip" on the posterior of the joint.
Positions.dbf:

| ActionCode | JointNum | SeqNumber | NewPosition | Pressure |
|---|---|---|---|---|
| 100 | 959 | 1 | 091001 | 00000170 |
| 100 | 011 | 1 | 85.000 | |
| 100 | 011 | 2 | 85.595 | |
| 100 | 959 | 2 | 091001 | 00100181 |
| 100 | 011 | 3 | 86.783 | |
| 100 | 959 | 3 | 090002 | |
| ... | | | | |
| ... | | | | |
| ... | | | | |
| 100 | 959 | 50 | 091002 | 00000170 |
| 100 | 011 | 50 | 172.205 | |

Assume device number 959, an attitude sensor shown in this data is upper torso vertically mounted. While there was no significant change in roll recorded (stayed between 001 and 002) during the session (the action cataloger didn't lean to the left or right significantly as he stood up) the pitch went in just two timeslices from a slightly leaning back 091 to a vertical 90 degrees (which is a lot for just two timeslices but only a few records are in this example). During the gap in the data where the dotted lines are, the user attained a pitch of 45 degrees (not shown since it occurred in the dotted line area) as the user leaned forward but by the time the user was standing fully erect again (third line from the bottom) the pitch was back to an almost perfectly vertical 91 degrees.

As can be seen, joint 011, like a joint on a knee joint going from sitting to standing erect went from 85 degrees to 172.205 degrees over the duration of 50 twenty millisecond timeslices. One might think that, because there are about 50 timeslices and the joint gains roughly 87 degrees that about 1.7 degrees per cycle would be achieved but, in standing up from a seated position, the final snapping of the knees into fully vertical position is the fastest degree gain/second while the initial acceleration from stasis is the slowest and the current invention has the capacity to capture the full detail of both positions and speeds throughout the action for a true replication of action that allows synchronous replication of multiple joints simultaneously without tearing limbs apart with dimensional disparities mid-stroke.

The pressure field is, when the attitude sensors used include yaw and velocity, used for a different (non-pressure) purpose and can be understood by reviewing the database description above. Here, the first 3 characters are for vector of motion and the other 5 are speed along that vector e.g.: the first 3 characters of 00000170 for 00.0 degrees vector (yaw). It should not be surprising that the starting yaw was the origin (00.0) since we are coming off a fixed position that establishes the origin as that script's default yaw. Also, it will be common for procedures to reset the value of the origin to the current yaw at their beginning (making the starting yaw for that script 00.0 by definition) to allow easy transitioning to subsequent scripts without renumbering them. Exceptions, however, are recovery scripts which, before resetting the current yaw, want to know previous anchor yaws (the present origin), current yaws desired by the script and current attitude sensor readings for the yaws which provides information supportive of a smooth recovery from a condition that preceded the calling of the recovery script. The yaw vector in the example above varies only slightly (up to 001) throughout the script.

The 0017.0 (the decimal is implied) is the speed along the vector defined by the pitch and yaw values in units chosen by implementers.

The console operator selects "End Capture" and the record creation ceases. Using the processes above, the user could then create a standard position called StandingErect to capture the action cataloguer's now erect posture. From that point a new action sequence named StepWithRightFromStandingErect can be created to capture the action cataloguer's first step forward with his right foot in a walk to the point where the right foot is firmly planted and the left is beginning to come forward. Another can be created called OneFullStepSequenceFromRight that continues this motion, as acted out by the action cataloguer, back to the same point where he's on his firmly planted right foot with the left just beginning its forward swing again.

StepWithRightFromStandingErect establishes the familiar off-balance beginning of a walk cycle and OneFullStepSequenceFromRight begins a truly repeatable walk cycle that picks up on the first record where the last one left off. Now a user wearing the assistive clothing that follows that script can, regardless of physical abilities, be caused to assume a standard seated position, stand up and then take any number of steps forward.

Of course, a single sequence inclusive of gaining (or regaining) a predefined sitting position, standing up and walking across the room, etc. could have been captured as a single sequence (script) and, for many embodiments, this may be the best way. However, there are other new devices and processes that allow the user to choose his own actions interactively which favors a process based on a carefully broken down series of frequently used modular motions that can be strung together and summoned by the user and/or automatic means.

Much more detail on dealing with uneven terrain, steps, forks in the road, etc. follows a disclosure of the user-interface means by which the user can make choices that deal with such unpredictables.

Prior to going into more detail on scripts and procedures to enact motion, consideration is given here to optional new user interface devices that facilitate user guidance of the process. One such new means is an orally controlled data capture device with a radio transmitter or any other data transmission means (FIG. 8) operatively connected to receiving means which is connected to the processing means such that the user can indicate the next modular operation to do or even key in a queue stored series of modular operations to be executed in a fluid sequence with the ability to change or reverse those instructions at any point. One embodiment of the oral keyboard is a series of tiny, sealed, push click switches attached to the back of each of several lower teeth (much like orthodontal brace anchors are glued on) just above the gum line where it can easily be clicked by touching it firmly with the tongue. The buttons are rounded at the edges and/or encased by a soft plastic shield which can be glued directly to the teeth which softens any remaining edges and protects the contents. Alternatively, as shown in FIG. 9, 105, temperature or other contact or electro-sensitive including galvanic skin response (GSR) buttons recognizing the change in temperature, vibration, electrical condition, etc. when the tongue contacts them can capture the "keystrokes" with less effort and sometimes faster allowing more work to be done with less effort and friction on the tongue. The temperature or otherwise touch sensitive surface can also be much thinner than a button needing to be depressed thus making the device unobtrusive to the user. Each such tiny switch module can include transmission and power means and thus work independently of the others. However, in the embodiment illustrated in FIG. 8, each switch is connected to the other switches and directly or indirectly with the power, 100, and transmission means, 102, using mini ribbon connectors or wires similarly anchored to or strung between teeth or by other short-range communications means. Then, upon each close of any switch's circuit (when pressed or contacted by the tongue) it transmits via a miniature transmitter a tiny signal unique to the switch depressed (each switch causes a different frequency, amplitude or other recognizable code) which is picked up by the sensitive receiver worn on the body just inches away from the transmitter (or at least the receiver's thin antennae wire is so close). One wire in the ribbon can serve as the transmission means' antennae. Because radio transmissions lose power by the square of the distance from the source, the very close proximity of transmitter to receiver allows the current process to use very low-level radio waves protecting the user from radiation as it provides a strong signal that overpowers interfering radio noise that might interfere with the operation of the assistive clothing. The less than continuous nature of the transmission also greatly minimizes any radiation concerns and extends battery life.

The receiver, normally worn on the body, is operatively connected to the processing means also normally worn on the body such that the user can summon preplanned modules of motion as easily as the console operator did. Each transmitter switch's unique frequency and/or uniquely identifying codes, characteristics or protocols, when received by the receiving means, is treated much like the depressing of a different keyboard key by the console operator by the processing means. Thus the user can "type" and make user selections with the tongue quickly, especially when aided as described below.

An optional tongue-touchpad or mouse can be added as in FIG. 9, 104, located, for example, in place of the two frontmost buttons shown in FIG. 8, against the teeth using a touch, friction, heat, electro-sensitive or otherwise sensitive surface and assembly capable of returning data interpretable as position of and/or amount of contact on the medium similar to and including the familiar touchpad mouse replacements. The contact surface, typically rectangular and confined to the height of the protecting teeth but which can extend below the lower edge of the teeth over the lower palate to provide more space, can be, by user or implementer preference, curved to fit closely against the teeth or built up just enough to be a bit flatter to allow better tongue contact. Contact with receiving means can be independent and the tongue-touchpad/mouse can contain battery means even in the built up area behind the sensitive surface, but, in the embodiment of the current invention discussed here and shown in FIG. 9, it is connected to the shared communications and shared power means by wire or other data transmission means. This, through the assistive clothing interface, can be interpreted like a mouse action responsive to the peculiar jobs assigned to each point of the user's visual display or other user interface at that point in time.

An alternative embodiment of the above adds an attaching means which is an easily applied device much like a retainer used by orthodontists and often similar to the embodiment shown in FIG. 9. Fitting in the mouth, for example over the teeth, the "radio retainer" keyboard and tongue-touchpad transmitter, like an orthodontist's retainer fits comfortably in the mouth and permits eating, talking, etc. The operative elements of the oral keyboard above and/or tongue-touchpad are attached or molded into the support structure of that comfortable attaching means. In fact, for patients requiring orthodontics, the oral keyboard can simply be attached by oral prosthetics glue or otherwise connected or molded into the dentist's retainer itself. The battery, transmitter, keys and/or tongue-touchpad elements can be arrayed like the pattern of FIG. 9 or in any convenient array. Advantages of the removable assembly include ease of application, hygienic benefits of easy removal for cleaning as well as the practical benefits of easy battery recharging and repairs without time in a dental chair. Also, the wire-frame supports of the attaching means, ex. FIG. 9, 103, make an excellent, long antenna for transmission means further increasing the signal and lowering the necessary concentration of radiation. The wire may be coated, for example, with a thin electro-insulative polymer common to painted-on small-parts wiring insulation.

Also, a user who is totally dependent on the assistive clothing (no otherwise use of hands) can have more than one pop-in-and-out radio-retainer keyboard and/or tongue-touchpad and can independently execute a script directing his assisted hands to slowly remove the current keyboard and insert the cleaned and fully recharged one to make the user's periods of full independence essentially endless.

The receiving means also has an optional operative connection to a desktop, laptop or other computer means via a keyboard, USB, serial or parallel port, etc. and/or an insertable expansion card of any kind, infrared connection, etc. using existing and well known means thus allowing this user-interface to emulate a normal keyboard and mouse and thus enable the user to do anything that can be done on a computer. This typically, however, won't be an unprocessed-data connection of course since conversion means attached to receiving processing means will typically first convert the tongue effected button contacts and/or tongue-touchpad actions into characters, shift-keys, mouse motions, mouse clicks, etc. from it's own user interface (which may include alternative body-worn visual means and processing means which through the visual means communicates to the user a specific and temporary meaning for each such response which might turn a single click into a long series of keystrokes or programmatic actions driven by the user interface's current purpose). The user can also choose to have the visual response switched from, for example the glasses-delivered visual response described below to some other including the user's computer screen through the operative connection to the PC and/or special software running on the PC.

Also, an upper radio-retainer can house a full upper palate tongue-touchpad pad where the touch-sensitive area responsive to tongue contact is much larger and, potentially, covers a large area of the palate with a thin sensitive layer that contours to the roof of the mouth much like the typically plastic structural support portion of an upper retainer that fits comfortably against the roof of the mouth. This not only frees up the space on the other retainer for more optional keys but the additional area also provides an exponentially increased precision potential that can be activated without completely disengaging the tip of the tongue from other switches (the back of the tongue can be taught to engage the roof-of-the-mouth tongue-touchpad while the tip of the tongue is positioning itself somewhat for the next keystroke and reducing tiring of the user so long sessions are comfortable. The additional precision, particularly when the readings from the tongue-touchpad are software linearized (so that the curvature of the roof is mathematically flattened allowing the emulation of a flat touchpad), makes it practical for the user to compete with a non-handicapped user in terms of artistic detail in graphics programs as well as to perform rapidly and precisely as a design architect, etc. in every area from drawing, editing, typing, printing, phone auto-dialing, and emailing their results.

Upper-attitude guidance device. An additional user interface means is a head attitude sensor operatively connected to processing means such that a tilt of the head can be calculated, optionally in coordination with visual interface means, by additional calculation means into device specific data and commands to allow the user to direct those devices with the attitude of the head. This user interface means combines head mounted or head position sensitive attitude sensing means (such as accelerometers, attitude sensors-including gyro-driven, bend sensors on the neck, GPS, compass means, etc.) to, in coordination with calculation means, convert the retrieved data to a simple set of factors for head attitude such as pitch, roll and yaw and then, based on those parameters instruct other devices and processes according to parameters set up in additional calculation means.

For example, if (using a standing pitch of 90 degree vertical) the default vertical attitude of the head is 90,0,0 (pitch of 90, roll of 0 and yaw of 0) and the user's head nods forward resulting in 80,0,0 then the calculation means, if, for example, the current sensor application is directing a program to guide a mouse on a screen, will calculate a position on the screen relative to that change (and direct the cursor to move either by direct control or by the creation of compatible instructions for existing mouse drivers. One such calculation based on the sample above is: (where maximum considered pitch range is −30 degrees to 30 degrees based on 768 vertical pixels and maximum considered yaw range is −40 to 40 degrees based on a screen with 1024 horizontal pixels using X and Y coordinates from the true geometric x and y origin (bottom left of the screen):

If Pitch<60 then Pitch=60: Keeps cursor in bounds of the screen
If Pitch>120 then Pitch=120
If Yaw<−40 then Yaw=−40
If Yaw>40 then Yaw=40
Y=((CurrentPitch−60)/60)*768: Calculation of cursor/arrow coordinates
X=((40+CurrentYaw)/80)*1024

Since the sample embodiment above uses pitch and yaw to guide, for example, a mouse cursor on a visual display (which can optionally be clicked using the oral tongue-touchpad or keyboard), the roll value is free for other use such as signaling a script change with a quick tilt or guiding the roll of an airplane, virtual or otherwise. Existing eye position sensors can, with the same calculation and interface means of the current invention, be applied to the same purposes particularly when times of use of a current position is selected by the oral or other mouse or keyboard means allowing the eye to move freely at other times.

This upper-attitude guidance device can be used to guide any computer application including where a mouse or joystick is currently used through the assistive clothing interfacing means which uses established position parsing and instruction translation logic to create general directional commands common to most such pointing devices or device specific commands to directly replace a particular pointing or user data entry device.

The upper-attitude guidance device also, of course, has direct application to guiding the assistive clothing itself to control the direction and, where desirable, effect balance. Many paraplegics have the ability to control the head and neck. This can be used to allow them to direct their path, maintain balance "manually" (the automatic balancing logic can still take over when a imbalance tolerance is surpassed), adjust positions, etc. interactively when eating and drinking and even adjust speed of any operation. As will be shown, this allows a person paralyzed from the neck down to guide his path around and over obstacles and up even a spiral staircase simply by leaning the head in an intuitive, already natural-to-the-process manner.

Invisible Visual Display (optional): Allows the user to see the world around him while still monitoring his data. See FIG. 12 thru 17. This provides a user with a clear, even optometrist's corrected, view of the world while seeing, whenever desired and indicated by user entry means, data, menus, picklists, etc. that make guiding the assistive clothing as the user walks or typing a letter while on a plane practical.

While an experienced user will not require a visual response just to walk (in practice, frequent motion controls can be memorized and executed fluidly for smooth, quick response action), a visual response option is a useful new development for the following reasons:

1. To allow any user, disabled or not, a means of viewing data, programs or graphics, etc. without need of a conventional computer display.
2. To provide the user with helpful navigational and support information and support a fully interactive process even while the user is out walking.
3. To allow the user to see what he's keyed in before executing it when a computer screen is not convenient. The user can see a scrolling list of the active commands and those coming up below it as a means of checking and, if necessary, aborting an accidentally entered action. This speeds learning and adds safety.
4. To give visual aid to recall options and use fewer keystrokes because of context sensitive key codes displayed.
5. To allow the user who has no manual capacities to do extended functions from creating macro motion groups to writing letters, surfing the net or programming a computer.

One embodiment of this new development illustrated in FIG. 12 and FIG. 13A consists of ordinary looking glasses with a reverse image projected on the back (inside) of each eyepiece of the glasses with a focal plane calculated to be beyond the glasses and within the user's focal range so that the user can see (and see through the non-opaque projected image to see the world around him), for example, the data that would ordinarily be on a computer screen. This calculated focal control can simply be in the form of ordinary collimation as illustrated in FIG. 13A. Except in embodiments where collimation means is a collimating film such as at the projection means' exit point, the collimation means can be adjusted to be slightly reducing or slightly magnifying to achieve application specific effects. This embodiment is especially effective for display while walking because, even though the user can see the full width of his field of view, having the display superimposed off to one side, leaves the center of the user's field of view uncomplicated. In all reflective surfaces of all embodiments, a slight reflective coating such as a vapor coating (as is used on mirrored sunglasses but considerably less dense) on the inside surface of the glasses lens is used when there is a need to favorably leverage the projection means' reflected brightness against the light transmitted from outside.

Programmatic image enhancement provides vacant backgrounds for text to be displayed which results, in that example, in only the text itself being displayed over the user's view to provide an un-obstructing message. Other optional programmatic image enhancements include warping of the pre-projected image, by patterned point-remapping or other means, to effect an un-warped image even when distortion occurs because of non-planar reflecting means or a non-collimated projection from a source not perpendicular to the target. Although not tested for this patent, image pre-enhancement to accommodate a user's vision problem (such as retinal deformation) is an obvious natural use of the current invention. FIG. 13B is also an example of an LCD image source. However, any focusable or essentially collimated imaging source is applicable to the current invention.

Fiber optics, as in FIG. 13B provide an embodiment with high potential resolution from an image source separate from the glasses. At the other end of the cable (image source) a potentially larger display is reduced to a smaller array of fibers (but potentially larger number of fibers than pixels on the larger source screen) preferably in already collimated form. Typically, this pre-collimation is accomplished by the reduction and then collimation by a second lens of the image prior to its entry into the fibers. The fibers then carry the image to the projection means. At the exit of projection means, light can be lens focused or the fiber endpoints can be arrayed at Fresnel-like angles (resulting in an already convex or concave focusing image) as the light leaves the tip of each fiber. The embodiment illustrated in FIG. 13B uses a lens to focus the exiting fiber-carried light. However, because the light is essentially collimated as it exits the fibers, a collimating filter may be applied at this point as a low-cost, space-saving means of collimation. FIG. 13B is also an example of slightly convergent projection output.

FIG. 13C is an example of an additional or

In the sample embodiment shown below, the display is wide but short to minimize interference with the user's field of view even though the user can "see through" the reflected display.

This see-through visual display means also works with any user input device to move cursors across the screen or scroll visual pointer(s) indicative of current attitude for rapid and smooth user control of body direction. For example, using "action until release" (such as holding down a key on an oral keyboard or continuing a head attitude) can cause a cursor to scroll on the visual display.

This integration of these and other peripherals can be used for any number of user interfaces to allow quick operation with a minimum of clicks or other user actions. The user can select letters from the screen or key in letters from key combinations. 6 switches are shown in the example embodiment in FIG. 8. If 5 are used for alpha data entry, only 2 clicks would be required per typical character as displayed on the screen. See sample below. Of course there are any number of other programmatic interface aids.

Sample Screens:

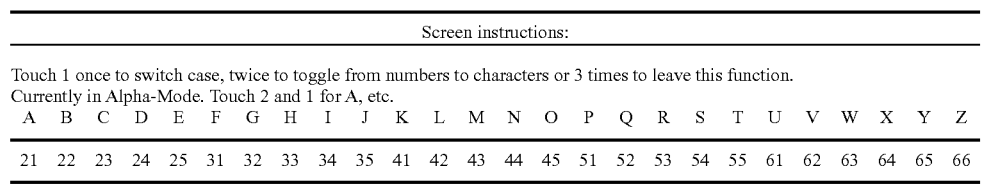

When the user touches 6 twice to switch to numerics the following screen toggles:

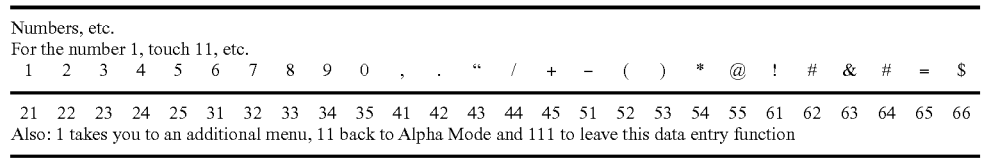

The user can optionally view on the visual response means a vertical bar or other indicator of his current yaw as illustrated in FIG. 18. Initially, of course, this would typically appear in the center of the display as shown in FIG. 18A which is superimposed over a distant clock as a fixed background. For illustration, consider the vertical bar to be blue (as the user would see it). Then, as the user's head turns in the current frame 2 degrees, for example, to the left to indicate another desired yaw, another vertical bar (gray in the illustration, yellow on the display), which was formerly in line with (and hidden behind) the blue bar, moves on the display two degrees to the right of the blue bar reflecting to the user the current yaw of the body's current motion as shown in FIG. 18B. The blue bar indicates the desired relative yaw while the yellow reflects the current actual body yaw as measured by lower attitude sensors. The processing means doesn't need to calculate the blue bar since it never moves. To place the yellow bar on the display, it places the yellow bar with respect to the blue desired yaw bar according to the equation:

$$BYI = (BA - HA) * C$$

where BYI is the body yaw indicator (yellow bar) screen X location, BA is the body attitude sensor's yaw reading in degrees and HA is the head attitude sensor's yaw reading and C is a constant conversion factor relating degrees of difference to number of pixels on the display from a perceived point of view.

As the head turned, the blue (desired direction) bar stayed in the same location on the screen (in the middle) but the head (and attached visual display) rotated.

Then, using the means disclosed further below that are automatically responsive to user interface directional input, the body, with the user's head and head attitude sensors on it, turns. Thus the yellow (actual body yaw) bar in FIG. 18C has responded to a 1 degree change in body yaw which is precisely offset by a 1 degree change in head yaw since the head rides on the turning body. Thus the yellow bar's movement was zero. (We assume here for example that only 1 of the 2 desired degrees of change was accomplished, even though numerous separate adjustments all of larger angles can be individually made in a single stroke, to illustrate on a small page how the system responds to "catch-up" conditions). Thus, the head, unless the user adjusted it (and we will for example say he has not yet responded), has moved with the body another degree of negative yaw (to a relative yaw of −3 compared to the original yaw but only −2 compared to the body's current yaw—thus the two bars are only 2 degrees apart).

Still, the user will, since his job is to guide with the blue bar, continue to "fix" the blue bar on his target and will thus correct the yaw of the head with a change in yaw of 1 degree in FIG. 18D leaving the blue bar at a relative yaw of −1 degree compared to the current yaw of the body (Just as a driver turning left naturally corrects the wheel to the right after the desired turn has been accomplished rather than leaving the wheel turned to the left). One degree of the two degrees has been corrected. The other will be done in the next SeqNum which may be in the same stroke as the weight-bearing foot's ankle and/or thigh and/or hip, as configured, continues to turn as described in detail below.

In FIG. 18E the assistive clothing has again rotated the body and head one degree and in FIG. 18F the user, continuing to chase the target moves to the right. Of course, many degrees can be corrected in a single step but this illustrates the process with simple numbers and that, though most corrections will be adjusted in a single step, it is possible to take more than one step to correct to a head demanded yaw correction.

The process, though cumbersome to discuss, is as natural as turning a steering wheel and adjusting back except that visual means provide additional support. It should be mentioned that, for many applications, this kind of precision is not required and the two bars would not be displayed. The user could use, for example, the head mounted interface to guide yaw progress and observe that progress with his natural view. However, where great precision is required or skills are low, this provides a means to precisely target a target and achieve it. It is also particularly useful in precisely locating a point in space, such as the vertical plane of the first step in a staircase for the automatic distance and direction calculation and response means that allow the user smooth and effortless approaches to spiral staircases, etc. as discussed further below with automatic controls.

b Pitch and Roll Indicators.

The system optionally provides an additional visible bar in the display which is similar to the vertical yaw bar above except that it is horizontal, moves up and down as the head moves up and down and it thus manages pitch. This is particularly handy when using head pitch to determine terrain selection as it is below in the code sample "PROCEDURE ExecuteScripts". Having a visible display showing the pitch lines (horizontal) for each terrain level and the pitch bar accurately positioned on it give the user enough accuracy to stay in the center of a range so that a bump or small balance adjustment doesn't affect the selection of terrain by moving the head (which moves with the body) beyond a range. Similarly, like on an airplane display, roll indicators can be added this reverse projection image display.

The visual pitch and yaw indicators, as mentioned, are particularly useful as crosshairs to identify a point in space supportive of such functions as automatic distance and direction calculation and response.

Typically, when the main program is running, the Actions.dbf and Positions.dbf tables are open at all times. Actions.dbf is already indexed by ActionCode and Postions.dbf is already indexed by ActionCode+SeqNum+JointNum. The ActionName field of Actions.dbf is displayed in a pull-down menu. When the user selects one, the data from the record in Actions.dbf referenced in that pull-down selection provides the summary data for the processing means such as length of TimeSlice, etc. Its ActionCode field value also provides the primary key for using Positions.dbf.

For brevity, the user programmatic interface is described in terms of scripts and, in particular, those with table structures described above. However, when the user selects what looks like a script above, for example, it may actually be a program written in such a manner as to perform the same key end functions the scripts discussed here do with potentially different table structures and memory means. Thus, discussions of scripted processes are used throughout this disclosure to describe any calculation and direction providing means to calculate and/or recall positional data and direct the assistive clothing's physical actions regarding those joint actions.

A seek is performed on Positions.dbf for the ActionCode just selected which places the file pointer on the first record of the desired script. Starting from that first record and proceeding down the table, the record is read. If the record is a typical joint-control position record, it executes the positions the record reflects as described above. If the record is a sensor value, criteria, etc., those values are stored in memory variables for the use of the program as described herein where those functions are discussed.

That process is effective with very fast equipment and ideal conditions. It will be normative, however, for the application software to continue down that table reading into memory all the sensor and joint-control position records having that same SeqNum (i.e. those actions to be accomplished in the same timeslice), consider current sensor and criteria data and then execute the commands to all the joint-control points simultaneously so that there is no cross-tension within joints and so that all joints move fluidly just as they were modeled. If this is accomplished prior to the end of the period identified in TimeSlice (unless the ActionType is a function that supercedes or uses the Actions.TimeSlice value differently such as a morphing script), the next set of Positions.dbf records (with the next SeqNum) are read (continuing down the same table), calculations are made, etc. but the execution is delayed until the expiration of the timeslice. Thus the processing means can typically stay ahead of the process and keep the desired meter even as volume of data varies.

This continues until the process terminates, another condition switches scripts (such as auto-script switching responsive to a condition as discussed below), a record itself points to another script (ActionCode) forcing a transition to that script (which may include a morphing process as described below) or, in the case of scripts whose Actions.dbf record has an action type indicating that the script is repetitive. A repetitive script will continue to repeat until other functions, including user commands and automatic functions, intervenes. To do this, the software, upon reaching the end of the Positions.dbf table or a record with a different ActionCode, simply performs the same seek command as above to start over at the first record.

With those elements explained, the process of following a script or set of programmatic controls will now be described further. If the capture logic described in the program code segment "Example Script Capture Snippet" above was used to create an action script that is actually just a fixed starting position, the cataloger wearing the position-sensitive equipment will:

a. assume the desired position to be modeled.
b. execute the capture program for a single timeslice thus
c. an Actions.dbf record will be created to identify this action and
d. one Positions.dbf record will be created for every joint monitored.

The resulting records might look like the examples below.
Actions.dbf

| ActionName | ActionType | ActionCode | TimeSlice |
|---|---|---|---|
| PositionSittingErect | P | 71 | 3000.000 |

Records: 1

When the ActionType is P, a morphing process to a starting position is indicated so the timeslice in milliseconds shown above effects a time for the operation of getting the user in this standard position (3 seconds). This value is so large for this action record because, rather than moving a fraction of a millimeter in a very short timeslice as a part of a long script of micro-short actions as would be common for an action sequence where, for example, ActionType was "A", the user here is allowed a comfortable time for the equipment to morph his current positions to those identified by the related records in Positions.dbf Thus, in this usage, TimeSlice does identify the time to achieve a single step in the action similar to the MDI of the referenced provisional patent. Instead, for morphing applications, the "step" that is accomplished may require many small steps in the morphing process with the sum of them all taking the time indicated by TimeSlice.

Note: the term "morph" describes a variety of procedures for transitioning a first set of points in either images or physical positions (such as the joint-control points here) to a second set of points or positions the latter of which are particularly applicable to the current invention. However, rather than document the wide variety of position-morphing techniques all of which are applicable to the current invention, the reader can visualize, for the sake of basic concept, for each joint-control point the procedural formula below denominated in terms of micro-steps appropriate for a stepper motor actuation means example:

For each joint-control point, the time allowed for the morphing process and distance to be accomplished are considered to decide how much motion must be accomplished in each cycle.

Micro-steps per cycle=MicroStepsToBeAchieved/
(CyclesPerSecond*(TimeSlice/1000))

Where TimeSlice is in terms of milliseconds, CyclesPerSecond is the number of movement cycles the actuator (based on the slowest actuator in the mix) and processing means can accomplish in a second and MicroStepsToBeAchieved is the difference between the current joint-control-point position (in micro-steps) and the position to be achieved. Thus, in calculating and effecting these changes for each joint-control position over a period of TimeSlice moving at synchronous but potentially different rates (each calculated as MicroStepsToBeAchieved for each joint-control point), each joint control point is morphed smoothly to arrive at the correct end position at the same time (in this example, TimeSlice milliseconds later).

Equipment responsiveness, the intensity of motion for the ActionName being catalogued and the fragility of the user will determine the appropriate TimeSlice and, for long sequences of tiny motion transactions, the TimeSlice will typically be much, much smaller. However, for the assumption of a standard position from who knows what kind of a position, a longer time is appropriate to prevent too much change occurring in too short of a time and thus potentially breaking the user's neck.

Examples of Alternative Uses for Positions.dbf File Structure.

Special routines can also be called by responses to records in Positions.dbf While there are any number of acceptable file structures, this is given as an example of one set of structures that meet the objectives of the process. Special records with specialized functions are recognized by special numbers such as in the JointNum as shown in the 2 examples below. These records can thus be used to call, morph to or switch to a different script or program. For example, for recovery-of-stability based scripts identified by script number range (ActionCodes), the default action is to morph (rather than to just pick up at the first set of positions in the called script) to the referenced script through commonly known procedures that, for each affected joint (in this process) calculate the distance and speed of adjustment as detailed.

As the currently executing program is routinely processing a set of Positions.dbf records for the current ActionCode in SeqNumber order, it encounters such a special record. It then remembers these parameters and checks them periodically as a normal part of its cycle using well-known and obvious programming procedures. When one of the conditions is met, the program executes the referenced script which can, incidentally, in turn, additionally or alternatively launch another program (not a script) by referencing its program number (as if it was a script number to be called) in the first (or any subsequent) record in the called script. Here is an example. Positions.dbf:

| ActionCode | JointNum | SeqNumber | NewPosition | Pressure | Misc |
|---|---|---|---|---|---|
| 171 | 9994 | 71 | 257000 | 00000200 | #(>1 |

Here JointNum=9994 doesn't refer to a specific joint but to a special functionality of this record. When JointNum=9994, for example, the program can be set to interpret SeqNum normally (since this must be inserted at the right point in the script) but the first 3 characters in Newposition now refers (in this example) to recovery script #257 which relates to an Action.dbf record (by ActionCode) which identifies a recovery script based on records in Positions.dbf matching that ActionCode. The next 10 characters (the last 3 of NewPosition and the first 7 of pressure) define two 5-digit numeric fields (Amount2 and Amount1 respectively). The last position of Pressure isn't used here. The first 2 characters of Misc (which is a character field) define the duration of the action defined in this record. The value #((shown as the first 2 characters of Misc) is, in ASCII, equivalent to the number 1400 used here as the duration which is the number of ticks or timeslices before the procedure being called terminates which means that, even if the steps have all finished, it will wait for the duration to expire before returning. If this number is zero it continues until it completes or is superceded by another called procedure. If it is 65,500, duration timing is ignored and it simply morphs back to the beginning of the script from which it came when it completes its last step. The > sign, the third character in Misc in this example, means "greater than". Other values for this column are <, =, < > and B (for "between" such that when B is used both Amount1 and Amount2 are considered to see if the value of the device is between those 2 numbers). The 4$^{th}$ and 5$^{th}$ positions of Misc is used here as the number of the device referenced in this record. In this sample it is a space and a numeric 1 which yields a decimal ASCII equivalent of 1568 (the device number).

So, in the example above, if device #1400 has a reading>00200 (which is Amount1, 2.00 if you assume 2 point decimal), the positions of each joint-control point are morphed to the first position of the newly called recovery script 257. At the end of the duration period of 1400 ticks, which normally would allow just enough time to morph to the new script and stay just long enough to stabilize balancing before morphing back to the beginning of the previous script(s) or process. When called from a walking script, it will not normally be configured to return to the point of exit since this could be an off-balance position requiring velocity not yet gained in such a morph to action).

Instead, either by a called process or simply a final record in the recovery script's Positions.dbf transferring control to a "first step" script, the user will be taken to a common stable, pre-walking position and put in motion before re-entering a walking cycle.

Thus, if the sensor device whose condition resulted in the response example above was an attitude sensor and the condition of the value that was exceeded had been its pitch (a value outside a safe "tip" angle), the above example is an example of this process as applied to call a recovery sequence.

This is useful for providing any number of continuously modifiable parameters in any number of sensors or devices that can call any number of responsive scripts or procedures. The duration value can also be used by the program to determine the number of morphing steps and the amount of travel to be achieved in each by obvious means of subtracting a small stabilization period and dividing, for example, the distance to be achieved by the remaining amount of duration (number of ticks) to calculate the amount of motion to be achieved per tick in the morphing process. This provides an easily adjusted, application specific means to have custom morphing sensitive to precise locations in an already executing script or process. By simply indicating the number of an attitude sensor in the device number for such a Positions.dbf record, this also provides a means to override for a period (duration) the default values for acceptable departures from the recorded norm attitudes used by balancing software for any point in the pre-modeled script. An obvious example is a stand-up from sitting position script where the pitch values will drastically differ from a walking script and will change continuously throughout the sequence.

Through this process that enhances typical morphing, any number of context sensitive recovery or special function scripts are easily identified and, more importantly, they are identified to perfectly match the body attitudes, velocities and limb positions of the particular point in a particular timeslice of a gait/action. For example, although morphing can be done from any set of positions to any set of positions to smoothly morph a user from a walking position to a safely crouched position to recover balance before being morphed again to the walking script, a script-position-sensitive recovery script provides the scripters with a powerful tool for adding efficiency and context-appropriate action. They can do this by selecting a script whose, for example, left foot raising and advancing action is much faster that the average of all the other joint adjustments required to move to the safely balanced crouched position. Thus, where a particular limb needs to get to its appointed place before or after the others (even though they would catch up to each other at the end of the script), this process is responsive to the full balance and inertia conditions that either the action cataloger experienced at the time the response script or that was intended by the writer of the response program. This process accommodates a great deal of specificity. For example, implementers can, if they obsess, have a different response process for every single point in the sequence that is precisely responsive to, for example, an actuator-sensed imbalance simply by placing a record for each in the script.

At the risk of detail overload, it is very important to note that implementers can also have any number of responses for a single point in the stride reflective of any number of conditions determined for the same device (such as a sensor). Case-like logic is supported allowing range responses. If, for example, for the same SeqNum and same device there were 2 records in Positions.dbf providing the following 2 conditions.
  if device #1400 has a reading>00200→process 257 (as in the example above) and the next record says:
if device #1400 has a reading>00300→process 258
  the process would consider them in the sequence provides in case form such as
  case device 1400>200
  do 257
  case device 1400>300
  do 258
such that, when 2 or more simultaneous conditional cases are simultaneously true, only the one intended by the implementers is effected to assure that a perfectly context-sensitive response is achieved from a limitless number of implementer-identified conditions. These functions are applicable to automatic balance controls, spasm control, etc. as detailed further below.

Numerous interactions of optional configurations of the applicable embodiments and unbalanced positions of opposing elements will require adjustments to calculations but these adjustments are easily effected in processing means by anyone skilled in the art of robotics programming.

User Self-Guiding Yaw: The user can select at the keyboard (used here for convenience to refer to any pointing, selecting or data entry means including the oral keyboard) to manually guide the yaw of the path he takes or manual can be set as the default condition as it is in this example embodiment. When thus active, the rotation of the head (or in other sample embodiments the movements of the eye or other controlling means that can be reliably sensed) can be used to modify the direction of travel. As described above, when using head attitude as a guidance means, visible bars displayed on display means or other indicators on the display can be used to help the user to visualize and more accurately fix upon the desired targets. However, the user can also simply treat head attitude like a steering wheel and guide the body without the additional visual support for many operations where great precision is not needed.

Ordinary magnetic or gyro based or other attitude sensors, worn as part of the glasses or other head based mounting, report a change in head yaw since the last frame was executed. For those that do not, the current invention's calculation means calculates the difference between the current yaw and the previous yaw saved in memory to gain the change by subtraction. For example, it may have increased in yaw 1 degree relative to the yaw from the previous timeslice. The system is thus being instructed to move towards this new yaw position starting with the next change in active foot or other convenient transition point. An alternative desired-yaw calculation that is used in this example embodiment is described above with the visual control interface. Here, a second attitude sensor mounted on the trunk of the body provides a comparative yaw providing an easily calculable (subtraction) differential between the head-desired and currently active body yaw. However the net desired change in yaw is calculated, it can then be effected by programmatic and/or script driven adjustments:

a. Programmatic and potentially intra-script/procedure: These user-guidance responses can be handled within the current walking script by programmatic or recalled adaptations to the current repetitive script and/or program. For example, as the right leg approaches mid-stride, the scripted or programmatically controlled stride is adjusted to increase the yaw of the right leg by advancing the thigh-mounted rotation ring in a programmatically controlled amount relative to the change in yaw. An example programmatic solution is to simply match the yaw being responded to. Thus, in this example desiring an increase in yaw of 1 degree, the programmatic control will simply rotate the thigh rotator ring 1 degree beyond the existing script or procedure's ring position increasing it's yaw 1 degree. Soon after the right foot is planted and prior to it's loss of contact with the ground, the same thigh rotator ring is rotated 1 degree of negative yaw beyond the previously planned yaw (ring actuator position). With the foot now planted, this rotates the body to achieve 1 degree of positive yaw which precisely accomplishes the desired change without having to change scripts or procedures. More involved and polished programmatic reactions to desired changes in direction, path slope and roughness of terrain follow logically as natural implementations of the current invention. For example, the same 1 degree change could be shared by the ankle rotator ring (½ degree) and the thigh rotator ring (½ degree) with both reversing after foot planting to effect a change in yaw of 1 degree. Even more extensive sophistication, for example, allows, in addition to the above, the hip to rotate positively and move laterally to the right and the stride to be shortened slightly to effect a very sharp right turn that recovers right back to the calling script or program's originally planned point in the repetitive process.

An even more responsive embodiment of the current invention allows moderate changes to be made with little or no waiting for special points in the stride to come around. Here, some or all of the desired change in yaw is achieved immediately using whatever foot is currently and independently bearing the body's weight which eliminates any delay at all for the majority of the walk cycle. There are points in a stride where both feet are touching the ground or one is just about to touch the ground and, during these brief points, changes are still avoided. Otherwise, if, in a single timeslice processing means subtracts the two sensor's yaw and there is a difference, it effects it immediately (or as soon as only one foot is touching the ground by the aforementioned means. If, for example, the desired yaw is 1.2 degrees positive, whichever foot is planted can be rotated (at the ankle in this example) 1.2 degrees negative turning the body 1.2 degrees positive.

Even more immediacy and significantly more turn per step is possible by additively allowing a foot that is just about to be planted to rotate just prior to planting and then, when in the next position in the stroke associated with firm ground contact (as detailed more below) for that foot, rotates in the opposite direction. For example, by turning the foot (thigh, hip, etc. as desired) to the right prior to planting and then reversing it after planting, twice as much potential rotation is possible in a single 1 foot half-cycle.

Processing means may keep up with these points in the cycle as to where each kind of rotation is appropriate. Or it may be simply contained as data in a script record being executed. In either case, 1 character is enough to, using simple programming techniques, determine whether, at that point/SeqNum, that joint-control point (in this particular example, the ankle rotator cuff) should be moved for this purpose. In this example embodiment a hybrid of the two is used where variables are stored in memory the first time the repetitive script goes by and, until told otherwise, these variables determine if this point in the cycle is an acceptable move point. Also, in this example, the character is imbedded as the last byte in the Positions.dbf Misc field is a:

"1" to identify that this joint-control point at this SeqNum is a good place for 1 way rotation or a "2" to identify that this joint-control point at this SeqNum is a good place for 2 way rotation (rotating prior to and after foot planting) or a "0" to identify that this joint-control point at this SeqNum is a bad place for any such rotation—wait for the next SeqNum.

It is also a practical embodiment of the current invention to adjust the lateral positioning of the foot being planted. For example, when making a sharp left turn it is not unusual to plant the right foot more to the left than normal (in addition to rotating the foot being planted). To accomplish this, processing means increases the retraction of the two inside thigh tendons on the right leg and oppositionally extends the opposing tendons on the outside of the same leg to effect that adjustment while creating a brief leftward lean at the waist as elsewhere detailed for perfect balance. This example embodiment, however, since more than adequate turning is practical without doing so and since those moves are so well accommodated by turning scripts (below) where desirable, illustrates intra-script turning only by rotation.

Optional proactive balance control. Turning the body, even in small increments, affects the overall body balance. In almost all circumstances the ordinary automatic balancing processes discussed further below easily handle the adjustment; typically with just a simple change in waist pitch and/or roll. However, for extreme changes or when the user prefers not to use auto-balancing or for high-speed activity, processing means also provides additive optionally configurable proactive balancing control. In these cases, processing means can make balancing adjustments at the same time or just prior to the yaw adjustments thus negating the out-of-balance condition before it exists. For example, a right-foot-planted rotation with the left foot in flexion, to achieve a large positive yaw change in a single stride produces a small southwest inertial vector on a northbound user. Using common table selected or calculated means, processing means can calculate or table select the needed adjustments. In this simple example, adjustment variables are created for the waist joint control points. These variables are honored for a number of timeslices associated with the same table or calculation. Thus, for this period, these amounts reflect the amount that the assistive clothing will change the planned positions of these joint-control points by simple addition of the variables to the planned position as normal positions are achieved. In this example, that could result in the additional retraction (in the amount of the variable) of the user's north and east tendons while extending in opposing amounts the south and west tendons thus leaning the user just as any normal walker would lean into such a turn and do so in advance of or simultaneously with the turn itself. Of course, any number of joints can be involved in balancing and any number of applicable procedures exist for the calculation of adjustment values that are then effected through the assistive clothing's joint control means.

These intra-process/intra-script approaches can handle virtually any turning situation. However, for special circumstances, very tight or sudden changes of direction or significant changes (more than just adjusting yaw a few degrees for a spiral staircase, etc.) required in special travel routines such as climbing steps, deep sand, very uneven ground or very steep slopes, etc., automatic script switching is a natural solution that can be process case-selected based on configuration criteria setting the norms for when they are required.

b. By script switching. As an alternative to or in coordination with the intra-script adjustments above, script switching accommodates even drastic changes in direction and simultaneously responds to changes in terrain. Scripts (action sequences from action.dbf and positions.dbf) can be switched "on-the-fly" (as the user is walking and at any point in the walking stride). Mid stride switches are made simpler by using a repetitive or "until further notice to the program" type action script. This script will continue to repeat itself in cycles until the user or the software (due to an exception) intervenes. The user can select, for example, a simple "four step" walking cycle (1. left foot down, 2. swing right, 3. right down, 4. swing left just up to full planted position). Of course, there are actually hundreds of time slices (sequence numbers) in this process involving numerous joints throughout the entire body. Each of these timeslices relates to a frame (a group of positions recorded with the same action and sequence number in the positions table) which includes all the attitudes, velocities, sonar distances and joint angle positions associated with that particular "snapshot" of time. There can be, for example, numerous scripts just for walking varying by speed, stride and slope arranged in a naturally transitioning order for easy "gearing up" for changing conditions. For example, the user may select a relaxed walking script for 0 slope (flat surface) with moderate speed and stride (the distance achieved with each step). This works fine until the slope of the terrain increases. The user then touches the up button to shift "up" to the next script which was recorded at a slightly greater slope. The program then picks up in the parallel frame for the new script.

There are several means for the program to identify the parallel frame in the new script so that a smooth transition between closely similar scripts is made. As is typical in emulations of real life, the methods, in practice, often work best in hybrids. Percentage of progress in the cycle is one means. If the cycles are catalogued in a smooth, fluid movement, the point 85 percent into the frames of the cycle of one walking script would be equivalent to the same position in the newly selected script. Another means is comparative joint angle or limb attitude. For example, the new script can pick up at the point where the angle of the front ankle tendon is the same as it was in the previous script. Or the new script could pick up at the point where the front active foot attitude is the same as the previous script. (The "active" foot is the one that is touching the ground or, if neither is touching (a running script), the one that will touch down next. However, when both feet are touching at the same time in a walking script, the last one to make contact is considered the active foot). Another means is the "mile marker" approach. Here, for frequently used cyclical scripts, action catalogers can even more finely tune shifts between scripts by entering a single mile marker record for each timeslice in the script to indicate the position in the full cycle stroke the time slice is in. Using the sample database structure as shown above, there would be, in addition to the other records in the Positions table, a single additional record for each timeslice identified as a timeslice record by its unique joint number (here used as a type identifier). Alternatively, an existing record in the existing script can be flagged as a mile marker point simply by placement of an "M" in the Misc field. The milemarker facility may seem useless when considering a smooth stroll of a walk. Everything is fluid and evenly spaced over time. However, the fine tuning of the milemarker can best be appreciated in scripts where sudden motions occur such that a more significant portions of the stroke are accomplished suddenly. For example, in a steep walking script on a decline (negative pitch), the action cataloger's smoothness is actually affected by gravity with changes in speed occurring at foot impact (a momentary slowdown) and muscle acceleration affects the smoothness of the stroke. Further, for very frequently used cyclical scripts like the walking series, it allows a very high degree of fine tuning as it allows adjustments to be made at a keyboard or programmatically based on how smoothly the transitions are made in practice runs.

Now consider an example using a hybrid approach. The user selects an action walk script from prepared action scripts arranged from steep decline to perfectly flat terrain to very steep incline. When the user senses an incline or his natural balancing senses tell him to "lean into" the incline, he can touch the up key once or a few times to skip up to a progressively steeper script (cataloged/recorded at a steeper incline). With practice, he can learn to do this as naturally as an able bodied person leans into an incline when his natural balancing senses tell him to do so. Alternatively or additively, using the upper-attitude guidance means as described above, it is even more intuitive allowing the user to simply lower the head (decrease its pitch) and allow the program (such as Pickscript below) to respond by switching automatically to the most applicable script. By providing a smooth spectrum of scripts, changes can be made to be smooth. However, by including in the script sequence being selected a morphing step (with a "P" in ActionType for example), or other means of identifying a morphing record, any gaps in the scripts that were overlooked or left out can be smoothly accommodated This adjustment to changing terrains can also be done completely automatically by sensing a need to adjust with distance sensors and/or scanned landing zone calculations, etc. shown in more detail under "Intra-script terrain, incline and other automatic controls" and "Inter-script terrain, incline and other automatic controls" (both further below).

A turning script as described below (a script that was cataloged with the user walking along a path that would, if repeated enough times, eventually become a circle), even though intra-script adjustments can accomplish most of the same things, has the additional advantage of broad, synchronized, general body adjustments that naturally accompany the lower joint rotation which is especially effective when the magnitude of the adjustment is large or special terrain considerations make that necessary. So, with, for example, a simple turn of the head in the direction the user wants to turn, the user can automatically select the correct turning script of a certain turning magnitude and switch back to a straight script when a turn is no longer needed. One example means for making such a decision in table form with programmatic support illustrates one kind of table that script-switching means can use to make script-changing decisions. This example is illustrated with a Guidance Support Table and Assisted Session Code Sample AttitudeGuidance.dbf

| | Direction YawChange (0 = left 1 = right) | | | |
|---|---|---|---|---|
| (in degrees) | (3 = straight) | Terrain | StrideLength | ActionCode |
| ... | | | | |
| 1 | 1 | 3 | 1 | 271 |
| 1 | 1 | 3 | 2 | 272 |
| 1 | 1 | 3 | 4 | 273 |
| 1 | 1 | 3 | 8 | 274 |
| 1 | 1 | 3 | 10 | 275 |
| 2 | 0 | 0 | 1 | 276 |
| 2 | 0 | 0 | 2 | 277 |
| 2 | 0 | 0 | 4 | 278 |
| 2 | 0 | 0 | 8 | 279 |
| 2 | 0 | 0 | 10 | 280 |
| 2 | 0 | 1 | 1 | 281 |
| 2 | 0 | 1 | 2 | 282 |
| 2 | 0 | 1 | 4 | 283 |
| 2 | 0 | 1 | 8 | 294 |
| 2 | 0 | 1 | 10 | 285 |
| 2 | 0 | 2 | 1 | 286 |
| 2 | 0 | 2 | 2 | 287 |
| 2 | 0 | 2 | 4 | 288 |
| 2 | 0 | 2 | 8 | 289 |
| 2 | 0 | 2 | 10 | 290 |
| 2 | 0 | 3 | 1 | 300 |
| ... | | | | |

After a modeled script is normalized (where the script is programmatically and/or user edited to better fit perfect norms such as exact stride length, foot lift relative to the terrain) a few scripts can be "grown" into an array of scripts by obvious extrapolation means. For example, in a well normalized sample script, the direction 0 script will be visually analogous to a direction 1 script to the extent that one can be programmatically generated into the other allowing the option of modeling only direction 0 scripts (leftward turning) and programmatically creating the records above for direction 1. Also particularly useful are the obvious applicable processes for extrapolating between, for example, a well modeled script with a turning yaw of 1 and one with a turning yaw of 10 to create intermediate scripts for turning yaws of 2-9 between them. Software support and modeling/simulations provide script editing and even from-scratch script creation using such tools to speed the creation of the above tables or other applicable script embodiments. When well done, this can improve normalization (since humans do things a little differently each time) and thus provide scripts that transition with improved precision and smoothness.

Also, in embodiments where different levels of Stride Length and/or Terrain are handled through programmatic position adjustments rather than such specific scripts for each variation (one example of the many applicable embodiments is simply an on-the-fly version of the extrapolation techniques above allowing use of, for example, a 5 degree yaw script and a 2 degree yaw script for a 7 degree execution), the Terrain and/or StrideLength columns would not be used in the table above which also reduces the number of scripts and the number of rows above.

Other optional parameters not included in this example include speed and load. Load, included for significant loads being carried that affect balance, can be effectively managed by balancing means which, for a load in the right hand, can simply bend the waist to the left programmatically additive to the bend reflected in the script in the amount programmatically calculated or, more typically, until the lower body attitude at the current point in the script is reached or other optional balancing criteria are satisfied which is why it is not considered in this example. However, there can be special "loaded" scripts for carrying burdens and additional fields can be used here for weight, leverage factors (lateral and vertical distance from the user's center of gravity) and yaw of load vector (to identify the operative vector working against that center of gravity with the weight given).

The following code snippet is an example of code supportive of one embodiment responsive both to an upper-attitude guidance device (in this example located in the glasses frame) or other pointing device which has been moved to reflect a negative change in yaw (negative is to the left) and a second attitude sensor on the back above the waist measuring the yaw of the body itself. It adds the optional element of continuous comparison with this second body yaw measurement to calculate a difference and use that difference to select and call an appropriate script.

The index labeled AttitudeChange below is sorted (indexed) by:

Terrain+Direction+StrideLen+YawChange

Where YawChange is the change in yaw desired to be accomplished in the script (in this example in a single stride). Direction is positive or negative to indicate right or left respectively, Terrain identifies the roughness of the terrain accommodated by the script and StrideLen identifies the length of the stride used in the script. YawChange and StrideLen are typically stored as integers. This allows another means to choose walking instructions that are sensitive to direction, terrain (smooth-floor scripts, bumpy-high-stepping scripts, step climbing scripts can all be identified and called up specific to not only direction but function), and current length of stride desired. Thus, with hands freee, the user can control multiple elements smoothly such as naturally navigating a spiral staircase even when the initial approach was imperfect. This effects one effective means of choosing transitional scripts that are effectively congruent at transition points reducing or eliminating entirely the need for morphing to the new script.

As can be seen below, this example embodiment allows the user to initiate a change in direction and hold that head position until the new attitude is achieved or continue to modify it in real time. The next time a stride can be switched (in this example there is only one transition point but there can be any number of within each stride sequence and here we have made that transition point mid-stride), the most recent desired changes in attitude based on the current head position is considered thus eliminating complications caused by tracking and having to back off of changes considered while a stride is reaching the next transition point in favor of simply reacting to the most recent differential between desired and actual. Like driving a car where the wheel is turned left to go left and then back to the right (which doesn't take you to the right at all but simply eliminates your leftward change over time in yaw) to straighten out, some practice is required to turn to the right point and hold it or adjust as necessary and then, like a steering wheel, turn the head back in the direction you don't want to go just enough to straighten up. While this can be done without visual aid, one is optionally provided and illustrated for yaw applications in FIG. 18. It provides a visible display means, such as on the front-projection glasses described, to target a position by locating a line or crosshair, etc. over the destination and keep it there as the body responds which is quantitatively shown by the two lines approaching each other in the illustration. In embodiments using visual support for pitch, a corresponding pair of horizontal lines are added to the lines shown in FIG. 18 creating a pair of crosshairs. Also, in embodiments where roll is used to control stride length, a separate bar can be added to the display to indicate a relative length or the existing bars or crosshairs can have their lengths increased or reduced relative to a superimposed norm bar or circle around the crosshairs to indicate stride length both current and desired.

The initial script in our example has a flat terrain (terrain=0). The transition point has been selected by the action cataloger as the midpoint in the stride defined by a SeqNumber. The code example below uses the user's:

1. Head yaw relative to body yaw to direct his leftward or rightward progress.
2. Head pitch to adjust to terrain. This is naturally set to be more climbing oriented as he looks further down as he would anyway on a steeper incline. Also, if the user jerks his head backwards to indicate a need for a secure position or simply as part of a spasm, this pitch response means automatically calls a fall recovery position to achieve stability before continuing. The pitch controls also includes a shortcut means to switch to a step climbing script by simply looking down a little more towards the feet as is natural on steps anyway and back to an appropriate walking terrain just by looking back up after finishing the stairs. Again, a standing pitch is used here.
3. head roll to naturally adjust the stride length to assure proper foot positioning for an upcoming action such as stair climbing just as we do unconsciously. This allows for example, hands-free (no data entry) means for the user to navigate across a room around furniture and up to a staircase properly positioned for climbing the stairs and select a stair climbing session that is also sufficiently yaw guided to allow easy navigation of a spiral staircase.

Other user interfaces, pointing devices, etc., including voice response, can optionally control similar applicable logic to the below to effect the selection of an appropriate script or programmatic means to follow a coordinated series of joint adjustments responsive to the user's direction.

```
PROCEDURE ExecuteScripts
Public Seq
Dim BALAdj(1000,700), TERRAdj(1000,700), StrideAdj(1000,1000)
    && Joint Control Point adj. arrays for Inter-Script balancing,
    && terrain adjustments & StrideAdjustments.On key label 5 do
GetTerrain && user terrain override
Do PickScript with 0, Terrain, StrideLen
    && Passing 0 parameter causes PickScript to use the user interface to pick the starting
    && script leaving that file open having executed the positions of 1st SeqNum(includes
    && morphing&transition to action script where ActionType=P).
    && Returns to this prog all data from the current records of current script.
DO WHILE .T.         && Main loop to run and change scripts
Intrafix = .f.       && Variable used to indicate if intra-script fix is desired
K=inkey( )           && Retrieve any keystrokes from oral kbd
NActCode = 0         && Clear New Action Code variable Stor 0 to BALAdj,TerrAdj && Clear change variable arrays
    && v—get attitude values from smart sensors
Do GetAttitude with HPitch,Bpitch,HRoll,Broll,HYaw,BYaw,BPChange,BRChange,
    Ychange,WaistAttitudeNAccelr( )
    && Automatic Balance Controls—Intra and Inter-script
Do PreBalance with IntraFix,HPitch,Bpitch,HRoll,Broll,HYaw,BYaw,PChange,Y,RChange,
    Ychange,WaistAttitudeNAccelr(  ),NActCode,Terrain,StrideLen,
    BALAdj( ) && BALAdj. is array of adj's needed for listed JCP's
If between(NActCode,850,899) && If fall-control stance is demanded, do it now.
    Do PickScript with NActCode,0,0 && If sudden extreme balance condition req'd
    && PreBalance to AUTOchoose recovery stance,run it now&user picks next step.
    Do PickScript with 0, Terrain, StrideLen && Now-stable user picks next step.
    NActCode=0
Loop && If surviving NActCode< >0 below, script will switch to it providing
    && PreBalance the option to override table based script changes below.
Endif && If NActCode=0,BALAdj( ) will be populated w/intra-script balance
    && adjustment values. Prebalance is currently configured
    && to also consider live user balance input & give it priority over auto.
    && Automatic Terrain Controls—Intra and Inter-script
Do TerrainAutoCk with Intrafix,HPitch,Bpitch,HRoll,Broll,HYaw,BYaw,PChange,Y,
    RChange,Ychange,WaistAttitudeNAccelr(  ),NActCode,Terrain,StrideLen,
    TERRAdj( ),NewTerr
    && Foot height responses, etc. may be intra-script.
    && TERRAdj( ) & NActCode managed like PreBalance just above.
    && Automatic Stride Controls—Intra and Inter-script
Do PreStride with  IntraFix,HPitch,Bpitch,HRoll,Broll,HYaw,BYaw,PChange,Y,
    RChange,Ychange,WaistAttitudeNAccelr(  ),NActCode,Terrain, StrideLen,
    NewStrideLen,StrideAdj( )
    && StrideAdj( )&NActCode managed like PreBalance above
    && Prestride also responds to sensor stub and step warnings.
    && User Yaw Controls Y = INT (ROUND(HYaw-BYaw))&& Round and integerize Yaw change desired
If Y < 0
    Direction ="0"          && Direction is left
Else
    Direction = "1"         && Direction is right
Endif                       && v---standing pitch of 90 degrees vertical used.
Do case                     && USER TERRAIN CONTROLS Between 0 and −30 *
    case HPitch < 60        && One user shortcut for selecting a stair climbing
```

-continued

```
        NewTerr = 3              && script w/stair depth managed by StrideLen below.
    case HPitch <= 70
        NewTerr = 2              && High Stepping terrain
    case HPitch < 80
        NewTerr = 1              && Moderate or uneven terrain
    case between(HPitch, 80, 100)
        NewTerr = 0              && Smooth surface terrain. Looking straight ahead
    case HPitch > 120 or K=6     && Jerk of head back or tongue depressing of key 6
                                 && initiates user-implemented fall control
        Do PickScript with 911,0,0
                && process implemented here through morph-to-fall-control script or proc.
                && to stop at safe, lower stance. PickScript actually selects the procedure or
                && script based on calling script (walking, climbing steps, etc.)
        Do PickScript with 0, Terrain, StrideLen && Now-stable user picks next step
        Loop
    EndCase
    If not empty(TC)             && If user touched oral key 5 & used tongue-touchpad to
        NewTerr=TC               && select a terrain, it creates a global response variable
        TC=0                     && retrieved here overriding pitch based control if active.
    Endif
Do case                          && USER STRIDE INPUT 1, Head attitude...
    case HRoll < -30 or K=1      && USER CALLED STOP.Call stop'n'stand proc or script
        Do PickScript with 101,0,0
                && process implemented here through USER CALLED morph-to stable
                && standing script or procedure. PickScript actually selects the procedure or
                && script based on calling script (walking, climbing steps, etc.).
        Do PickScript with 0, Terrain, StrideLen && Now-stopped user picks next step
        Loop
    case HRoll <= -15            && VERY short stride selected for detail positioning
        NewStrideLen = 1
    case HRoll <= -10            && Short stride selected for detail positioning
        NewStrideLen = 2
    case HRoll <= -5             && Moderate stride selected for initial approaches
        NewStrideLen = 4
    case between(HRoll,-5,5)     && Cruising stride
        NewStrideLen = 8
    case HRoll > 5               && Stretch stride selected for initial approaches
        New StrideLen = 10
EndCase                          && USER STRIDE INPUT 2, Tongue Touchpad drag-bar...
If K=4                           && User touches key 4 which starts GetStride in background.
    Do Get Stride with StrideLen,NewStrideLen
Endif                            && Runs until tongue-touchpad slidebar is released by user.
A=GettingStride( )               && Returns 0 if user has released tongue contact or the new
    A <> 0                       && stridelen from the global var created by GetStride which
    NewStrideLen=A               && runs till user releases tongue contact.
Endif                            && Overrides roll based control if active.
                                 && USER STRIDE INPUT 3, CROSSHAIR FIXING...
If K=3                           && Crosshair identified destination&automatic stridelen
    Do CrossHair with IntraFix,HPitch,Bpitch,HRoll,Broll,HYaw,BYaw,PChange,Y,
        RChange,Ychange,WaistAttitudeNAccelr( ),NActCode,Terrain, StrideLen,
        NewStrideLen
Endif                            && Overrides other controls if simultaneously active.
                                 && Decide here: Respond to user intra or inter-script.
If NewTerr <> Terrain OR Y <> 0 OR NewStrideLen <> StrideLength
                     OR NActCode <> ActionCode
    If abs(Terrain-NewTerr)<EasyTerr and abs(NewStrideLen-StrideLength)<=EzStride
                     and abs(Y)<EzYaw
        IntraFix = .t.           && Causes MoveBody to include intrafix in move
                                 && If change is moderate, just fix intra-script
    Else                         && Need to SWITCH SCRIPTS
        select AttitudeGuidance  && select the table illustrated above
        set order to AttitudeChange && select index for finding degree values
        CY=str(Y,10,2)           && put yaw in index stackable form
        seek NewTerr+Direction+NewStrideLen+CY
                                 && pick rec for new attitude(s)
        NActCode = ActionCode    && remember the new script to be switched to
        select &CurrentScript    && switches back to old script tbl till transition pt.
    Endif
Endif
```

&& Switch Scripts and/or Adjust Here . . .
   TranPoint=Transition(SeqNumber+1) && returns .T. if at acceptable transition point
     && v—Make normal timeslice moves including intra-adjustments
   Do MoveBody with TranPoint,BALAdj( ),TERRAdj( ),StrideAdj( ),Seq,1,IntraFix, Terrain, NewTerr,Y,Pitch, Roll, YawH,YawB,PChange,RChange,Ychange,    StrideLength, NewStrideLen,NActCode
     && Runs every pass but, if it's a transitional point in script & NActCode<>0 does
     && only override portions like balancing&stub prevention since new script follows.
   If TranPoint and NactCode<>ActionCode
     && If at transition point in old script & need new script.
   Do PickScript with NActCode,3 && SWITCH. Opens script&moves to 1$^{st}$ positn.

*** There may be a "placeholder" record for a given SeqNumber which causes no action if the action cataloger managed to have no motion at all on any of the joint-control points for a given timeslice and that is the way it's used in this example embodiment. However, these placeholder records can be eliminated to save space by simply skipping a SeqNumber in the script for any timeslice that is totally inactive in the action cataloging session and modifying the processing code to recognize a "missing" reflection of a timeslice in the table and returning from Move1Slice having done nothing for such a missing SeqNum.

Obviously, for intra-script corrections only, when timeslices are set to be very short, the equipment will sometimes be unable to make the desired changes in the same timeslice. MoveBody, the program in the example embodiment called by ExecuteScripts for making the pre-calculated intra-script joint changes, is normally configured to limit the

| Endif | && ADJUST. If not transition( ) or IntraFix=.t., cont.normal script |
|---|---|
| Seq = Seq + 1 | If GetInterrupt( ) or K=2 && Key choice or function checked for user or other && interrupts & exits the program if it finds one. Function |
| Exit do | && returns .T. if user or a process has requested an exit. |
| Endif | |
| Do KeepLastKey | && leaves only most recent keystroke in kbd buffer. |
| EndDo | && Continue cycle. |
| Return | |

*Here, in this sample embodiment the implementer chose to treat a pitch of 80 (looking slightly down, 10 degrees, from the 90 degree vertical standing pitch used in these examples) to identify a slightly irregular terrain given as level 1. A zero is the flattest surface, a floor, a 1 requires more lift in the stride, a 2 (pitch of 70) is a high stepping stride associated with a slightly crouched not-quite-climbing position and 3 (pitch of 60) is a shortcut means to selecting a step climbing response whose depth of step (some steps are very deep while others are very shallow) is responsive to the current roll value. These can be managed through selected stride scripts sensitive to terrain, as shown here, or by other programmatic steps. There can be many more levels of course beyond this sample. Thus, as the user naturally looks down more closely towards the feet in rugged terrain, the software selects scripts for more rugged terrains, etc.

**When Pickscript is passed, as here, a non-zero value (indicating a script transition), it compares current joint-control point positions against those of this first record (by subtraction) (the first SeqNum of a script typically includes a record for every joint-control point) and compares the absolute value of the resulting difference against a maximum tolerance norm for position differences in script changes (so we don't jerk the user) and, if any of the absolute values of the results of the above subtraction exceeds that norm (or set of norms based on joint-control position and/or script) value, morphs to that first set of positions (reflected in a starting record for each joint-control point with a SeqNumber of 1) over a period of timeslices rather than moving to the slightly different positions at maximum speed for smoothness and to move all the joint-control points on the same joint synchronously rather than pulling against each other by moving to the new point at different speeds based on actuator differences or simply due to positional advantages of one actuator position over the other causing an unwanted variance. When control is naturally returned to the calling program (above), we naturally set TimeSlices=2 because the script switch and, where necessary, morphing logic already took us through the first SeqNumber.

amount of change to any set of norms including those that are joint-specific (some joints can move faster than others) and those that are embedded in the script itself for point-by-point specificity and extended cataloger control. While it is true that as long as the ankle rotator ring, for example, can move as fast under a load as the head can turn it's attitude sensors (example is head-attitude yaw direction) in terms of degrees of change, this is not an issue. However with slow equipment or fast users, it is accommodated in the following manner.

When a desired intra-script change is in excess of the maximum for a joint-control point to be moved, one acceptable solution is:

1. For user initiated yaw corrections, all one-way yaw corrections (where the limb isn't first rotated in the direction opposite the desired direction prior to planting to double the maximum inter-script turning power per stride), user-indicated intra-script terrain adjustments, and balance adjustments: Less change than was requested by ExecuteScripts will be accomplished by MoveBody in that timeslice subject to norms but the next timeslice is just a fraction of a second behind whose motion will be the recalculated response that includes the precise progress accomplished in the previous timeslice. For example, on a yaw correction being accomplished with the currently planted foot, the actuator (in this example the ankle rotator ring actuator) moves no more than the norm-limited amount in the current timeslice, the next pass resamples the current user head position and, if the same and the yaw is still not fully accomplished, will continue towards it. However, if the user has changed the direction, it will immediately respond to the user's change using this process.

2. For, two-way yaw corrections, sensor-initiated intra-script terrain adjustments, sensor-initiated intra-script stride adjustments, and any sensor-initiated intra-script change occurring at a non-adjustable point (rare point where both feet are planted in a walk sequence, etc.), a multi-timeslice enduring-goal process is used. Arrays of changes to be made to future scripted positions, typically containing SeqNum, joint-control point number (JointNumber) and values for each of those future affected records in the repetitive script, are created. If they can't begin until a certain point in the stride (such as the first point where only one foot is touching), that point will be the first SeqNum used. These values are added to the appropriate joint-control point's scripted value in the appropriate timeslice (SeqNum) when they come around. However, if the need for the change goes away or reverses (such as when a user indicates a left turn in one timeslice creating the array and then adjusts the desired yaw back to the right), the array is cleared and recreated based on new conditions.

For example, when a user, potentially over many timeslices since the process allows it, has a desired yaw that is substantially ahead of the current yaw, it is desirable to accomplish it in one step to allow maximum intra-script turning in a tight space. If the change, however, exceeds the maximum smooth change by simple one way rotation in a stride, the current invention will normally be configured to use two way (where the airborne foot soon to be planted rotates in the undesired yaw direction and then, upon firm planting (normally recognized by a given SeqNum in the repetitive script or other recognizable point) reverses itself to perform, potentially, twice the auto-balance-stabilized turn in a single step. Using case-based logic in MoveBody, a combination of currently planted foot rotation followed by subsequent free foot pre-rotation is used when at those points in the repetitive stride that favor it to produce smoothly executed, large angle adjustments with the change spread smoothly throughout the affected portion of the sequence.

This important facility also accommodates the still slow distance sensor rates required for high-accuracy. Unlike the examples in 1 above where a continuously resampled approach will always have a fresh new reading awaiting it, a foot mounted distance sensor, for example, may not have another good reading for many timeslices or even until the next half stride.

Thus this provides an effective means of managing the maximum amount of motion accomplished per timeslice while maintaining a continuously adjustable environment that accommodates slow actuation equipment and sensor responses.

A few other controls applicable to the current invention for directing these actions include the oral entry methods above, hand-held or body mounted controls, voice response (where special commands not anticipated by current script can be easily called to action without paging through screens of data and also for the safety and convenience of being able to quickly completely change functions and to direct extensive processes when other direction means are not present). For example, for a paraplegics first thing in the morning, this allows them to verbally call a procedure or procedures to put in their oral entry device, etc. By easily switching to a script or programmatic procedures responsive to the degree of change in yaw in the middle of a walking script, for example, a simple, intuitive gesture can call a script to take over as soon as the current leading foot (the one not planted) reaches a certain point standard to walking scripts (such as mid-stride or stride initiation, when a foot becomes the leading foot) or any point or points amenable to smooth transition from the current stride to the turning stride of the example. Adjustments such as yaw changes can be immediately effected on the current foot by simple rotation of the planted foot as illustrated in the example code embodiment above. Thus, a user in a straight, repetitive stride script could, for example, move his head a bit to the left (the direction he wants to go) and, his direction is immediately modified to reflect that change in head attitude intra-script. If the changes are drastic (if they exceed the norms set for intra-script changes), the script-switching means software, when at an easy transition point (for this example we'll use mid-stride, where the current leading foot has completed exactly one half of it's path prior to planting and stride attributes are particular compatible for switching between scripts) will be switched to a script with a very similar gait to the current script especially in terms of height of lift above the ground to minimize or eliminate morphing at or prior to the transition point). It should be noted, in the code snippet above, the favorable nature of an embodiment that adjusts towards the desired transition point even while waiting for that transition point to arrive effecting a de-facto morphing process in the natural process of following the soon to be switched-from script. Although implementer preference will guide this, turning scripts will typically not be repetitive but single cycle because a sharp turn in excess of 90 degrees can be accomplished with a single cycle and because of the ease of programs, like the snippet above, to use them repetitively in a manner that is easily adjusted over time to new attitude conditions.

Transition points can also be dynamically selected based on factors in the present and about-to-be-called script or programmatic procedure to select the smoothest transition with the least adjustment. For example, when switching from a smooth surface procedure to a high-stepping procedure, the beginning and ending points in the stride of the current procedure are more congruous to the new procedure since the foot solidly contacting the ground at that point has the same altitude in both procedures.

By using compatible walking scripts or programmatic procedures (i.e. scripts or procedures with the same basic body position in any congruent position in the stroke, particularly at the transition point(s)), using any number of programmatic, case logic or table based means (the code snippet above being one example), the switching means simply begins to follow the new script or programmatic procedures at the transition point in the script with no morphing required (because of preceding intra-script adjustments and choice of smooth transition points) and the user feels no jerks or out-of-balance condition. The new script, if it is a turning script, will assume a slightly different balance but it will do so from the transition point forward. However, for a script of extreme direction change such as one responsive to a reduction in yaw of 40 degrees may reference a transitioning script or programmatic procedure for such an abrupt change (either a positional morphing script as described elsewhere herein or a procedure to effect that change over multiple script records, typically the former) which may, in turn, call another and so on. However, since a sharp change in yaw can be accomplished in a single stride, the example code embodiment above simply accomplishes the desired attitude changes in a single stride.

The above directions from the user can, of course, also come from the "oral keyboard" or other user-interface devices. Two or more such user-interface devices can also work together. For example, the choice of terrain and length of stride can easily be controlled by the oral keyboard. Here the user can, for example, by tapping the rightmost key for a higher terrain value and the one next to it for less as needed and tapping the leftmost key for a lesser stride length and the one next to it for more control both the stride length and the terrain. Or, the tongue can be slid left or right on the oral touchpad to decrease or increase the values respectively. The head yaw that continually guided the user's direction would then be used still for controlling direction. This frees up pitch and roll for other purposes.

Thus, the user's desired changes in direction can be effected by either intra-script programmatic adjustments, inter-script adjustments (switching scripts) or a combination of the two. For example, if, when a new script does begin, a small adjustment is required, processing means would naturally respond to both the user's direction desires and automatically sensed needs, as in the above code sample "PROCEDURE ExecuteScripts", to correct it with a simple intra-script adjustment. In fact, when a user indicates a direction change, unless the program is configured to force the user to pick his solution, the program itself will decide which correction means to take to satisfy his demands as in the sample above. Further, if a script change is desired in a pass of that program but it the stride is in a bad position to switch scripts, the intra-script corrections will be made. Then, in the next pass, the whole thing is recalculated again and the intra-script changes already while waiting for a script-switching point, stabilized the user and left a smaller problem to solve in this subsequent pass. Thus balancing corrections, (except those made by foot-plane adjustment which do require a pre-planting point in the script) never have to wait for a script change. Also, as just mentioned with foot-plane adjustments to accommodate balance on bad terrain, there are other intra-script processes that can't be executed in a few points of the walk cycle (particularly at that instant when both feet are on the ground). When that occurs, the MoveBody program will not add those particular adjustment values to the scripted joint-control point values being effected. Again, intra-script balancing such as waist bending is never delayed.

Also, in that code example, if the user indicated desired change in yaw is less than EzYaw (an implementer-determined amount of change in yaw easily accommodated within the script) and/or a desired change in stride length is less than EzStride, it will be handled by intra-script adjustments rather than changing scripts unless other factors (such as terrain or stride length). EzYaw and EzStride are global variables originally based on parameters set up by implementers for an acceptable intra-script change amount. In this example embodiment the EzYaw variable was treated as if there were only one set of joint control points to be concerned with and, in fact, intra-script yaw changes can be effected by just one (here the thigh rotator). However, in many embodiments EzYaw( ) will be an array whose parameters (related to joint-control point numbers) indicate the tolerance for each joint-control point the implementers of the current invention consider key to rotation. Also, in the called program MoveBody called from "PROCEDURE ExecuteScripts" above, these values are managed to be smaller in the amount of already achieved rotations in the same current stroke. At stroke change, they are returned to their configured values. This allows many adjustments to be effected in a single stride-stroke without the program forgetting the limits of how far the joint can rotate.

Finally, where the stride length is determined by the step recognition and automatic distance sensing means or viewing means cross-hair-aligned with upcoming step-up by user, etc., the stride length is recalculated to a precise length designed to automatically approach a step or curb with strides that leave the user in the precise position in front of the step, or other stride-switching opportunity, for performing the step-up or other significant change of stride operation.

Balancing Interface: The scripts and/or programmatic procedures that control movement also control balancing, as described herein, by recalling "good" attitude values as they were recorded in a script and/or as calculated in a programming procedure and/or responsive to balancing sensors. Thus, balancing is controlled for the user as detailed further below.

However, there are also embodiments where the users may want to balance themselves. For example, spinal injury patients who have full upper mobility can learn to balance for themselves while "riding" their legs and thus eliminate the need for much of the upper-body equipment. However, even the paraplegic who has no upper body control below the neck can, if desirous of controlling the balancing process or simply overriding the automatic balancing when desired, can do so by using an effective user interface. Example is made here of the upper-attitude guidance described above to allow the user to balance using positions of the head. As suggested above, the oral keyboard can be configured to handle changes in stride length and terrain freeing up the pitch and roll for the natural process of balancing. When you sense yourself falling forward, you naturally bend backwards and when tipping backwards we lean forward (decrease pitch) to regain our balance. Left and right (roll) work the same way. Using these natural instincts that are built into us, the current invention allows the upper-attitude guidance means to effect balancing by allowing the users to lean their heads intuitively and have the assistive clothing respond with appropriate balancing. User balancing programming retrieves the pitch and roll in degrees as in the code snippet above and responds with responsive body motion. In a perfect world, the waist (and/or other applicable joints), for example, would bend degree for degree with the head responsive on a 1:1 ratio with head attitude. This will work and the user can become comfortable with the intuitive interface. However, because not all actuators are calibrated by degrees and leveraging will be desired by some implementers, a conversion calculation appropriate to the actuation means is also applicable using obvious means. Thus, users have an intuitive means to balance as an override (activated by oral keyboard, voice response or other activation means) to the auto-balancing functions or simply to save money or wear less equipment for users who may also prefer to do more themselves. In the example using the upper-attitude guidance device, the head is used but eye position, voice response, etc. are also applicable options. The assistive clothing software and sensors also provide a means for the smooth transition from one script to another as is detailed with the other automatic functions below.

The oral keyboard or other communications means can, in addition to "click" based commands, be used for continuous as needed commands. For example, the user can, while walking forward, continue to take steps as long as one key remained depressed. This "action until release" functionality is also useful in managing motion to appropriate fixed positions to accomplish more sophisticated processes like meeting and grasping a glass. Using the above, the user can easily assume a standardized "sipping posture" position, make manual adjustments for precise positioning and contact with the glass, and then bring the glass smoothly and precisely to the lips, tip the glass and sip the drink at leisure.

In fact, a variety of functions benefit greatly from the ability to "bump" a limb's position just a little for fine adjustment by, for example, the tapping of a key in the oral keyboard, nodding the head slightly, etc. In the drinking from a glass example, the user, having reached the glass to the lips still would like to control how quickly it is tipped to avoid bathing in it. Certainly the current invention provides mechanisms for and implementers can and will provide menu options for the specific bumping of specific joints in small increments in a user indicated direction as an effective embodiment to provide an unlimited variety of user directed actions. However, even this simple example in a safe seated position involves 15+ joints operating synchronously with each joint moving at different speeds throughout a complex set of actions as the joints in the hand, wrist, elbow and shoulder move in harmony to control the pouring of a liquid in response to "bumps" i.e. taps on the key or continuous pressure over a period to advance the process just a little or just for a little while. While the prosthetics industry has struggled greatly with such issues, many special procedures can be set up by creative minds with the current invention. One such example means of managing extremely complex joint motion in tiny, user controllable increments without losing smoothness and synchronization is additionally illustrated here. The action cataloger performs the drinking script including both pickup and pouring. In that session he consumes the entire glass and then places the glass back down. A short value for timeslice is chosen at the keyboard during this data capture phase to enhance resolution as steps are broken into smaller pieces. During portions of the script where bumping is to be set up, either the cataloger or a person monitoring the session on a support workstation can depresses a key during that part of the session causing the capture software, while adding records to Positions.dbf to add, for example, a "B" (or a more space-efficient bit-level flag) to the Misc.field to flag records in that timeslice as positions amenable to bumping. Obviously, during a fast walking script, bumping is less applicable than in a secure seated position where changes in inertia responsive to such changes in velocity are not major factors. When these records are being executed (those flagged for bumping), user interface means are sensitive to, for example, the touching of a particular key on the oral keyboard to stop the process until it is bumped again. The user can continue to tap the key for very controlled progress of an already modeled or programmed process involving perfect synchronization of dozens of joints and can also continue to hold down the key for periods of controlled continuous progress along the script or process steps. Thus with a single key the user controls a complex set of motions.

Also, as alluded to above, the assistive clothing provides means for specific joint-control point control. This provides an unlimited variety of user actions to accommodate unplanned actions. While the user interface for choosing which joints to bump is not an issue (user menu's etc. are not peculiar to the current invention), joint retention is. When moving one joint-control point, the opposing joint-control point(s) will normally be moved as well in the opposite direction still maintaining the retention pressure as detailed above.

Special procedures are also supported by the current invention which execute these motions not by requiring the user to think of which joint-control points need to be moved and by how much but by simple left, right, up, down, in, out and twist left and right motions. Thus the user without hand or arm control can guide his hand precisely to a glass by, for example, choosing a drinking script that opens the hand into a wide, pre-grasping position and moves the hand and arm in the very general vicinity of where the glass will be (typically intentionally erring by falling significantly short of the glass). The next step of that script or process then calls a program responsive to the user's input and the user directs the hand to the pre-grasping position with the already cupped hand around the glass. When the user indicates the glass is located, the manual guiding program terminates returning control to the calling script which may continue or call a subsequent script in either case morphing the current joint positions to those of the next step and then continuing the script or process such as raising the glass to the user's lips, etc. using the example means above or other practical variations.

Examples of user input to identify desired directional changes are:

| | |
|---|---|
| Up and Down: | Head pitch |
| Left and Right: | Head roll |
| Forward and backwards: | Forward and backward on tongue-touchpad |
| Twist wrist in and out: | Left and right on tongue-touchpad |

Thus, for example, it, while advancing the tongue forward at a speed comfortable to the user, the user's head pitch tilted up and roll increased to the right, the hand would move up and to the right as it advance towards the objective at the user's desired speed. In one embodiment reflective of FIG. 19 and focusing on shoulders (there are several combinations that will accomplish the action and this is one of them), that change is effected as the rear over-the-shoulder tendon, in a modified tendon based system, retracts to raise the arm from the front, the lower posterior lateral tendon and the upper posterior tendon (there are two tendons in this embodiment used to raise the arm laterally from the top of the shoulder) pull left (causing the shoulder to rotate right) while the lower elbow tendon retracts the elbow towards extension along with additional retraction of all opposing tendons following the retraction rules and logic described above. Implementers can polish these example embodiments with smoothing logic The assistive clothing itself can be used to model calculations used to accomplish this effect. The shoulder movements, for example, were used above for left to right and up and down. Rather than researching and programming extensively to develop positional relationships of multiple joint-control points to accomplish a given directional movement on potentially asymmetric joints (such as this example), the action cataloger simply models, for example, from a seated hands-near-a-glass position, a motion directly upwards, preferably following a vertical ruler. The relationship of how much each joint-control point changed to accomplish that one dimensional movement is noted. This can be done for each of the dimensions (left, right, etc.) and used in a table based or purely programmatic conversion of directional requests to actual joint-control point adjustments needed. However, because the joints themselves often perform asymmetrically in practice (at different general stages of joint motion), for some joints (the shoulder being one), more precision with less implementer adjustment required is attained by modeling different stages independently to record data best applicable to the joint stage in which the user begins the motion.

More sophisticated variations of this process allows the user to simply align the crosshairs of the visual display means at the point on the glass of desired contact on a point on the hand, such as the "v" between the thumb and index finger, and the program will guide the hand to that grasping point optionally at a speed determined by the user through any of the user interface means before returning control to the remainder of the drinking or other script. This allows a user to simply look at a target object, move the hand precisely to it (at the speed indicated as the tongue-touchpad is slowly traversed in that direction) and release the tongue to allow the script to take over and pick up the object.

When eating at a table, users can orally switch modes (changing the function of user interface elements) and automatically and proportionally lean forward at the waist as they tilt their heads forward to better adjust body position. Thus the functionality of elements of the user interface are different for different points in the process by, for example, the imbedding of key assignments in Procedures.dbf records within the Misc field reassigning head attitudes, for example, to direct different actions). In coordination with other user inputs, the balancing response (here used to lean the body forward) can be turned off for some period. By matching the pitch and roll of the body to the relative pitch and roll of the head, as measured by attitude sensors and/or accelerometers, etc. optionally compared with fixed sensors below the neck or contact motion sensing devices, the user is not limited to motion in one direction but can lean forward and to the right, for example. Thus he can lean over and place his head precisely where he wants as the body flows in the same direction guided by the head. Also, since a person who is seated or standing has little need of yaw walking guidance, the same user can similarly twist the upper body at the waist (in the embodiment of FIG. 3 by rotating the waist ring) responsive to the yaw of the head. Since the arms move with the shoulders and the shoulders with the body, guiding the upper torso in any direction with the head provides an alternative means to fine tune where the user's hands actually contact a glass being picked up in a drinking glass script. This, like the hand and arm guidance discussed earlier, also allows the user to overcome small errors in the script or elements to be a little out of place such as the pencil he's picking up (he could actually write with a pencil using a writing script that worked from text entered at the oral keyboard or by verbal command) in a writing script or a fork he's picking up, etc.

User Speed Control. While there are many means of communicating changes in speed to the program (including voice commands and "keyboard" commands), this example embodiment uses a tooth mounted pressure sensitive sensor that reports, using the same communication means as the oral keyboard, an increased or decreased speed command to the program with increased pressure and reducing it all the way down to a complete stop with reduced pressure. As the user directed pressure increases, the timeslice of the current frame of the current script is reduced proportionate to the amount of change in pressure. As the pressure is reduced, the timeslice effected is proportionately more. When pressure is effectively 0, the timeslice becomes infinite stopping the program for further instructions. The script-recorded timeslice is the standard against which the changes are calculated upon.

An equation sample effecting such a change is:

$$D=RD/(P/C)$$

where D=actual duration of the current frame, RD=the recorded (scripted or default) duration for this frame, P=pressure of the sensor or other acceleration/position communication means and C=a constant reflecting a pressure typically falling in the normal operating pressure range of the activity which is selected to effect a comfortable range of speeds. As the pressure increases, D decreases (making the motion faster). As pressure decreases, D becomes larger (slowing). When P=0 the process stops to prevent division by 0 and because the user intends to stop. As already alluded to above, the same speed control can be indicated by the user with other means including tongue position on a touch-pad.

Automatic Applications:

Consideration has been given above to balancing under user direction. However, the current invention has extensive means for the automatic sensing of and solution to out of balance and a variety of other stability sensitive conditions.

It is a relatively simple matter to automatically balance something on a wheel. All that is required to sense a problem is to sense a non-vertical condition, move the other way in an amount proportional to the number of degrees from 90 and continue the process in a loop. Balancing a human being in the off-balance manner in which we traverse the earth is another matter altogether. The body is not only off balance much of the time but it's net vector is made up of arms, legs and torso all swinging in varying directions at varying speeds. And, rather than having a stable point of reference like a pair of wheels always in contact with the ground, the human legs and feet are off and on and turned in and out.

The current invention provides a variety of means working together to not only sense out-of-balance body attitudes that are good but also to identify those that are bad and sense them even before the out of balance condition actually exists in measurable form.

Adjustments: Overall Body Balance.

Though script switches would usually, by their very "already balanced model" nature, manage the bending of the waist and all the rest of the body to balance the body as inclines and even rolls change and even though the landing plane to foot attitude matching processes (detailed later) provides balance stability, an additional intra-script/intra-process layer of control provides additional flexibility and security.

When switching of scripts to match terrain slope, etc. and even additional intra-script adjustments of the foot and lower leg still require additional control (if implementers failed to create a smooth and broad enough spectrum of script choices) or when there doesn't happen to be a script that goes far enough for the particular situation at hand (unforeseen circumstances), an additional layer of control is provided intra-script.

It is possible for the foot to perfectly match the terrain and the full body script to be very close to perfect and there still be problems:

1. When close isn't close enough. It is possible that the script that best matches the conditions doesn't match it closely enough. This will result in conditions different from those recorded in the script. For example, when the attitude sensor on the back of the lower waist area returns pitch or roll values still differing from the script even though the landing zone met the foot perfectly and the script in use is the best (because the next one "up" the list exceeds the adjustment needed). Then, based on the degree of variance from the scripted pitch and/or roll (with the response calculation based on well known procedures for calculating a graduated response not unlike calculations above), an excess pitch, for example, would be met with an increased retraction of the anterior waist tendon (based on a simple table or algorithm based calculation reflecting the directly proportional relationship of magnitude of variance in attitude v.s. amount of response)) with a corresponding decrease of the retraction position of the opposing (posterior) waist tendon causing the user to bend over enough to more closely achieve the recorded attitude. In each subsequent frames (these frames can be visualized in one embodiment as individual passes through the main calling loop of the code snippet ExecuteScripts), subsequent comparisons of the now-refined-actual positions v.s. planned result in progressively finer adjustments as needed return the user to the perfect proper attitude and balance just as any normal person bends at the waist to balance. The head can also be tilted as a user interface to direct additional balance as already indicated but this is unnecessary for most applications. Roll differences still existing after other adjustments have been made below the waist (or when they are not being used as a user or developer option) would be similarly managed by adjusting the left and right waist tendons.
2. When something unexpected, such as being bumped by an external force, strong wind, a crumbling of the surface beneath the foot, etc. places the user "out of balance". For example, when an exceptionally strong wind hits the user in the face tipping him back slightly. In this case, an accelerometer or velocity sensor, like the one on the back of the lower waist area, registers a velocity or acceleration along the current motion vector significantly different from the one recorded in the script. As in 1 above, the system would either:
  a. Switch to a more forward leaning script in the same family or
  b. Adjust the angle of the waist and even the head/neck causing the user to "lean into" the wind just as any normal person would.
  c. Both.
3. When a script is not running but a position needs to be maintained. For example, when no walking or other motion scripts are being executed but a standing (or even a sitting) position is being maintained. With no such adjustments it is perfectly possible for even a sitting person to fall over. Here the positions being maintained become the "persistent script" and any deviation from them is controlled by intra-script adjustments. These adjustments can be limited to the waist as in this example but can also include the head, hips, legs and ankles, etc.

In a perfect world, since the action cataloguer was in balance as he stood and walked across the room, the user following precisely the same motions should be in balance in smooth terrain. As long as the user stays at home or wherever surfaces are flat, things can work out that well. However, people want to go wherever they want so, for those "out in the field" applications where floors aren't flat, etc., there are additional means. The attitude data stored in the example above records for each timeslice of each step the initial overall body attitude (and optionally many local body attitudes) and every change to it. To sense an out of balance condition is more difficult than it seems since many operations, like walking and running, require a temporary out of balance condition. There are existing balancing technologies of varying effectiveness (especially when dealing with legitimate and desirable out of balance conditions). Their failures are typically a failure to allow adequate flexibility in terrain particularly as directed by a user "on-the-fly", i.e. in real time as the situations develop. In addition to attitude sampling and response systems that attempt to keep the element upright at all times, the current invention has the advantage of knowing at a full body level (including any or all limbs and the torso), at any point in time, what joint/limb should be where. Thus the current invention continually compares the current attitude readings with the original readings from the action cataloguer (who was "in balance" even when his body was, to an attitude sensor, out of balance) to sense an imbalance situation which could be caused by anything including the slightest slope in the road. This does not preclude the use of older balance sensing mechanisms being used in the current invention but does provide a superior means for recognizing and dealing appropriately with any exception condition quickly, before the user finds himself on his face.

There are several sensed indications that an out of balance condition exists or is coming soon from other unexpected conditions. Some of them are listed below.

Out of Balance or Adjustment Needed Sensing Means:
1. When any of the attitude sensors record a pitch, roll or yaw value adequately inconsistent with the recorded value in the appropriate timeslice.
2. When an accelerometer on any part of the body records a different velocity along any of the pitch, roll or yaw vectors other than the one recorded for any frame.
3. When contact is made to a shoe sole located, or otherwise located, pressure sensor when there is no pressure recorded at that time in the process (in that frame) such as stepping on a sudden rise in the terrain.
4. When contact is not made to a pressure sensor that should have been per the recorded session (such as stepping into an unexpected decline or a hole).
5. When an optional toe mounted and/or knee mounted (or other strategic location including the lower back to allow the user, for example, to sit down smoothly in chairs of different heights) sonar or other distance sensor senses the closest element in the path as being closer or further away than recorded acceptable distance. This could be, for example, a sudden incline, a rock or a hole.

There are a variety of ways to adjust balance once an out of balance condition is sensed or predicted. Contact and pressure sensors are useful for timing, comparison and calibration. However, though they are also useful in the current invention for balance adjustments and impact prevention/control, the advance detection means of the distance sensors for the purpose of impact prevention/control are given more attention in this description for their obvious advantages of advance reaction.

In addition to the ability to switch scripts to adapt to incline and terrain, there are additional balancing controls that can operate within a script. These intra-script balancing processes, while not replacing other existing balancing techniques or those listed above or below, provide an understanding of an approach helpful in the applied use of the current invention.

The relationship of intra-script balancing procedures to on-the-fly script switches can be compared to a car's transmission. If you want to go 40 mph you need to get in, lets say, third gear. From here you fine tune the speed with the accelerator. You could go 40 mph in a lower gear perhaps by greatly exaggerating the accelerator (winding out the engine) but when that far from the intended range it's better to go ahead and shift. Intra-script balancing is comparable to the fine tuning of the accelerator while the on-the-fly script switches can be compared to the shifting of gears. After you "shift the gears" by changing to the appropriate script you have a range of adjustment within the script by adjusting joint angles to fine tune the balancing. While you could probably do with just intra-script balancing adjustments for many cases, for significant changes in terrain script switches provide full body adjustment to motion and terrain differences that affect the whole body and leave you with room for additional intra-script fine tuning balance adjustment as well.

Intra-script balancing can be effected manually by the user but can also be effected automatically.

Automatic intra-script adjustments can be based on sensed values that conflict with what should be expected based on the script such as an attitude in the current frame that conflicts significantly with the one recorded for that attitude sensor in that frame. Some categories of sensing adjustment needs are listed under "Out of Balance or Adjustment Needed Sensing Means" above. There is seemingly no limit to how complex you can make this process since any number of accelerometers, angle sensors, sonar sensors, etc. may be considered as part of and applicable to the current invention. A limited process of the current invention is described below as monitoring and responding in a limited but effective manner.

The sensors can be placed anywhere and aimed at any angle but in this example are foot (special shoe) mounted. Not all of these listed are necessary but all are useful.
1. One or two (to better sense impediments and preferably alternately cycled with different wavelengths to double reading speed) toe mounted distance sensors aimed at a relative pitch of 0 (straight ahead for a foot at rest on the ground).
2. One sensor on each side of the foot just behind the toes aimed at a relative pitch of −45, yaw 0 (forward and downward i.e. 45 degrees from the roll axis of the foot).
3. Two additional distance sensors placed near the heel on the side as close to a −90 degree pitch (i.e. perpendicular to the tangent to the earth when the foot is at rest and to the major roll axis of the foot) as the attachment means will comfortably allow. Placing one on each side of the heel allows a comparison distance to sense lateral inclines that would affect the roll stability of the user.
4. Another pair is placed near the heel at a pitch of −100 providing another valuable measure particularly as the heel comes down towards the terrain.
5. Front ball pressure sensors located on each sole just posterior to the toes registering contact with the walking surface as it returns the pressure value. One on each foot.
6. Heel pressure sensors located on the heel portion of each foot at terrain contact point.
7. Torso mounted attitude sensor located on the back of the lower side of the waist rotator so that it less affected by bends at the waist.
8. Foot mounted attitude sensors monitoring the pitch, roll and yaw of the length line of the foot (the roll axis) and the velocity of the foot along the measured vectors.

Any or all of these sensors can be used to capture information in scripts and capture it again as the script is executed so they can be compared and responded to appropriately. The current invention provides great latitude in the selection of and addition to the list of sensors above and the logic that responds to them.

For speed and data economy, these distance sensor records are recorded in the action cataloging process only when the distance sensed is less than a minimum value which (which can vary programmatically at different points in the cycle). Similarly, pressure sensors record (create cataloging records) only when actual pressure is registered. However, they are considered at all times during a user session to provide exception information whether or not anything is expected to be there to be measured.

Even within this category of automatic intra-script balancing with all the protections and controls above, there are several different and separable processes that can effect a better balancing control including:

Landing Zone Attitude and Distance PreScanning: The script in effect at the time just prior to planting the active foot could be the second (or 20$^{th}$ for that matter) script in effect in this cycle alone as scripts can be switched at common mile markers within a cycle as a means of adapting to changing conditions in the potentially hundreds of frames in a single cyclical script. Typically action cataloging sequences will be recorded on very smooth terrain at specific pitches and, optionally, at varying combinations of pitches and rolls. However, roll exceptions can typically be controlled when executing a script recorded at 0 roll (as shown below) making the creation of special scripts at odd rolls unnecessary. Zero roll in recorded cyclical walking scripts is assumed here. This allows easy comparison to a stable norm for easy detection of and response to exceptions. As the inactive foot swings to prepare to become the active foot and begins to reverse its direction slightly and lower itself into the planted position, known software procedures can treat this as a scan of the foot planting area using distance sensors like those above thus providing a pre-landing pitch and roll value for the calculated landing plane for the foot. Those known software procedures typically record readings over time to "map" an area. Similarly, this example embodiment uses the Positions.dbf data format for storing sensor readings tied to SeqNumbers to provide a time-based set of distance values that effect a "scan" of the area. A simple comparison of anticipated distance to actual distance at each point provides a simple means of comparing plan to actual in obvious programmatic logic. As applied to a landing zone, comparing the attributes of the thus scanned landing zone to the one modeled indicates changes in landing zone attributes. While all sensors (and others not listed here) can be used in especially deep algorithms to calculate landing zone distance from the foot's position, pitch and roll, adequate data from just 1 or 2 front mounted distance sensors along with the foot attitude sensors are both simple and adequate and will be considered here. Different applications and engineers will result in the use of many different means to use the current invention's sensing means to measure the landing zone plane. In this example we will create 2 virtual landing zone planes with one supporting the anterior ball joint area of the foot (this is the anterior landing plane) and the other supporting the heel area of the foot. Each of these sub-areas are broken into quadrants. The highest point in each quadrant is taken as the height of the quadrant and the triangle inscribed in space by the highest point in each of the highest 3 quadrants defines the landing zone sub-plane. Since the foot doesn't twist to accommodate differences in these 2 sub-plane plates, the pitch used is the average of the pitches for the 2 sub-planes (which can be thought of as a tangent to balance the foot upon) and the roll is the average of the 2 sub-plane roll values. However, as described in better detail elsewhere, for climbing steps and other conditions where the heel doesn't touch, only the anterior landing sub-plane is used to define the landing plane.

Multiple sensor arrays in excess of those listed above allow more points to be considered in the scan and can improve both speed (multiple sequential distance readings limits throughput) and accuracy. Also, while it is possible to scan ahead and read the frames ahead of the current position in a script to calculate at what point in the foot's preparatory to planting swing it is, in fact, "scanning" the foot planting area, in cyclical scripts this is unnecessary since the mile markers for this position in the swing where sensors are scanning the landing zone will already be known. In fact, when the action cataloger created the script (which can be modified at the keyboard later for extra fine tuning), values for landing zone pitch, roll and distance (on the aforesaid controlled terrain of appropriate attitude) can be saved as a single record with the appropriate sequence number reflecting the point (after the scan at cataloging) at which time it was calculated. There will, of course, be a record for each foot since a typical cycle includes both feet becoming the active foot. The landing zone plane, for the purpose of attitude scanning at least, is ordinarily based on the averaged values of the anterior landing plane and the posterior landing plane. However when, in the action cataloging process, there is a "square wave" change (significant change in distance while scanning from posterior landing zone to anterior landing zone such that long distances are experienced up to a point followed by sharply shorter distances after the recognizably square wave is encountered and the square wave occurs after passing the posterior landing zone), only the anterior landing sub-zone is used in the calculation of the landing zone attitude. This is particularly useful for climbing steps and very steep inclines where the action cataloger's heel never touches. A fixed point in the landing zone, here the lateral center of the anterior portion of the front ball joint area (where the foot typically first encounters a step when climbing stairs or steep inclines), is measured for distance by averaging (since there are 2 sensors in sensor 2 in this example) the two distances at that point in the scan. Typically in a cyclical scan, this point in the scan will be a certain mile marker point (as it is in this example) but it can also be defined as a percentage point of completion of the stroke, a specific sequence number, etc. Thus, significantly before the user's foot is planted, the program can calculate the current pitch and roll of the upcoming landing zone, the distance to it and also look in the script to see the model pitch, roll and distance thus easily calculating the relative differences in pitch, roll and distance. This provides exceptionally useful values indicating exactly what adjustments need to be made before the foot hits the terrain.

When a difference is sensed between the current landing zone for the currently active foot and the recorded landing zone (non-zero values for relative pitch, relative roll and relative distance), implementers may configure the transition to another script as explained in too much detail already. However, for most "foot" oriented incidents it is more practical to allow intra-script processing means to follow a simple set of rules to make responsive adjustments to a wide variety of situations. To do this, adjustment variables are created to be applied to temporarily adjusting the attitude of the affected limbs to better accommodate the terrain. Great detail is not required here to disclose to an experienced person how to make these adjustments but, for example, if the relative pitch of the actual landing zone was positive 3 degrees (small enough to affect only the ankle/foot attitude), an adjustment variable would be created for the anterior ankle actuator such that, when it was added to the current frame demanded position, would result in an additional tendon retraction to achieve an additional ankle pitch of 3 degrees. For moderate terrain aberrations, this is one of the purposes of the things the ankle does best as it protects the body's existing attitude by adjusting its own. Similarly, an adjustment variable would also be created for the posterior ankle actuator to ensure that it extends additionally just enough to allow the 3 degrees of increased pitch, etc. Minor adjustments to the left and right tendons in this example may also be profitable where the joint is asymmetrical. Thus, when the foot does impact the ground it encounters the ground with the foot attitude matching the attitude of the portion of the terrain it impacts consistent with the manner of contact intended (as modeled in the action cataloging process) and the body balance is preserved. Extensions of this approach to roll by changing primarily the left and right ankle adjustments to match a landing plane whose roll was non-zero are obvious. This provides not only a "surefooted" stable walk but helps maintain a stable balance even on uneven terrain as well.

Adjustments: Landing Zone Height Higher than Anticipated.

While individual sensor data can be used for adjustments, the virtual landing zone is used here for it's ease of application. Landing zone recognized and distance sensor (like 2 and 4 above) recognized discrepancies between the current values and the script have similar adjustment responses. For example, if any of these sensors indicate that the landing zone surface plane as calculated above is higher than planned, adjustments can be made by one of the following means:

a. The script can be switched to a more "high steping" script intra cycle as shown above in On The Fly Script Switches.

b. The height of the foot can be adjusted (raised) by the amount of the difference by creating adjustment variables for the knee and hip joints which will result in the raising of the foot by that amount. The adjustment variables created will, however, as understood by all in those in the robotics industry, result in adjustments to not only the hip and knee but to the ankle as well to increase the height of the foot without changing it's attitude.

c. Both. The majority of the adjustment can be made by switching to the appropriate script with minor adjustments, if necessary, using adjustment variables Adjustments: Trip and Stub Preventions: Controls on the Currently Inactive Foot.

The above landing zone height adjustments do not protect the user from impediments just forward of the landing zone but through which the foot must pass in the normal stroke or from impediments to the foot during the positioning swing prior to (anterior to) the landing zone. Also, in the step climbing process, uneven steps require height adjustments (they require square wave responsive angle adjustments too but that is considered separately below). When, for example, sensor 1, which scans in advance of the positioning swing, returns a value closer than the value recorded for that sensor in the recording of the script for that frame (as it scans from frame to frame) or if it records any value at all when none was recorded in the frame, that indicates a possible trip or stub condition anterior to the landing zone. This is dealt with differently based on where it occurs.

Case A: If this obstruction exists in the landing zone itself Nothing needed. It will be taken care of by the landing zone controls above.

Case B: If this is in the most anterior portion of the positioning swing, this mile marker or degree of completion identifiable position in the swing, while a very small portion of the swing, is vulnerable to kicking something even though it is outside (past) the landing zone. As soon as this condition is identified (and that can be made even earlier by adjusting the sensor angle if the equipment is too slow to respond) it's remedy can be begun immediately by one of several means including:

1. Switching to a script that purposely has no overswing for at least this cycle. (Incidentally, many walking scripts will have no overswing by their nature such as very steep inclines, steps and higher stepping scripts like those walking through high grass, etc.) Or 2. Negatively adjusting the frame demanded position of the knee and ankle (intra-script terrain adjustments). This can be done by creating adjustment variables that will be added (positively or negatively) to the values demanded by the frame. In this case it would create variables that would reduce the retraction value for the anterior knee tendon and increase the retraction value for the posterior knee tendon). Adjustment variables are also created for the ankle joint to maintain the foot's proper attitude while the knee's position is modified. These values would result in additional retraction of the anterior ankle tendon and the corresponding extension of the posterior ankle tendon. These adjustment variables will endure, and thus remain effective, until the frame identified by mile marker or degree of progress in which the foot would have normally already retreated behind the area now occupied by the impediment.

However, in the preferred embodiment of this option variable administered changes are implemented gradually as a percentage of the remaining distance to the point of calculated collision and then graduated to a return point. While there are many calculations that can effect a similar effect, the following is an example of one.

PD is the frame number (same as SeqNum if first SeqNum was 1) in which the impediment was discovered.

FI is the frame number where the foot was scripted to pass the point currently occupied by the impediment.

MP (a frame number) is prior to FI as the foot swings forward by enough frames to be considered a margin of error. The foot will stop at a point prior to FI by the amount of travel scripted to have been covered by between MP and F1 to allow a small distance between foot and impediment.

FR is the frame in the original script where the retreat from the overswing ends as the backwards motion of the foot is stopped by the heel planting on the terrain.

FM is the frame where the foot was scripted to reach its maximum forward extension.

$RP_{FT}$ is the retraction position for tendon T in Frame F.

$NR_{FT}$ is the newly calculated retraction amount for tendon T in frame F

At the time of discovery of the impediment, there are FM-PD frames in which to graduate the response. The advancement needs to be retarded to the joint positions in MP. At this point in the motion the affected joints are in a singular direction with no reversal of direction until just after FM. Now, the program wants to go through the same number of frames (and must to smoothly accommodate other body parts with scripted action in these frames) but arrive at a prior point, the point originally scripted for MP when actually executing frame FM. Thus, the positions of the anterior and posterior tendons for the hip, knee and ankle will be adjusted in frames PD+1 through FM proportionately. More specifically, these anterior tendons will have their change in retraction (from the previous frame) reduced and posterior tendons will have their retraction increased. One formula to accomplish this is below:

For any affected (hip, knee and ankle) tendon T in frame F (which is, by definition, between PD and FM) the new retraction amount for the tendon T is:

$$NR_{FT}=(RP_{FT}-RP_{F-1\ T})\times((RP_{MP\ T}-RP_{PD\ T})/(RP_{FM\ T}-RP_{PD\ T}))$$

i.e. the New Retraction for a given tendon T in a given frame F (between PD and FM) is:

the change in retraction in this frame as compared to the previous frame $(RP_{FT}-RP_{F-1\ T})$ times the relative originally scheduled change of MP-PD divided by the originally scheduled relative change of FM-PD). Though there are many other calculations capable of adequately adjusting the progress to end at MP such as:

$$NR_{FT}=RP_{FT}-(RP_{FM\ T}-RP_{MP\ T})/(MP-F)$$

which calculates the amount of stride shortening and divides by the number of frames left and subtracts it from the recorded degree or amount of retraction for each remaining frame up to MP. However, the approach in the preferred embodiment (the first equation) has the very substantial advantage of penalizing the amount of previously recorded advancement in each frame (which varies by the varying amount of advancement in each joint in each point in the stride) precisely for its momentary share of the shortfall thus maintaining the important synchronized relationship of all joint-control points consistent with the architecture of the rest of the assistive clothing process.

Thus the forward portion of the swing is smoothly terminated just prior to encountering the impediment. Thus the stride was shortened to avoid the impediment and, in fact, this provides an effective process for shortening a stride for any reason including intra-script stride adjustments to negotiate distances in walking or step scripts. In fact, this is the process used in the preferred embodiment by the program PreStride called by the main script execution looping program ExecuteScripts. Here, the calculations are made once, the proper adjustments for each is saved in the passed array StrideAdj( ).

When the automatically sensed condition that caused PreStride to create the intra-script adjustment array ceases to exist the array is simply set to 0 and will be ignored by MoveBody until it is repopulated.

However, for this impediment in the path example, there is another set of calculations and operations required since the script includes subsequent frames that reverse the path of the foot until it encounters the ground solidly. Actually, many scripts will not have an overswing that exceeds the landing zone but those don't need to be considered here. This description is specifically for those scripts that do include an overswing. The equation above provided the calculation of adjustment variables that caused the forward swing to terminate at MP, just prior to the impediment. However, if it is allowed to continue in a backwards direction between FM and FR as far as it was originally scripted to move between FM and FR, the foot would move too far backwards and miss part of the landing zone. Thus, for the frames FM+1 to FR, the following equation can be used to proportionately reduce the travel such that the foot terminates on the landing zone as it was originally scripted to. The new retraction amount for a tendon T in a frame F during the execution of frames FM+1 to FR will be:

$$NR_{FT}=(RP_{FT}-RP_{F-1\ T})\times((RP_{MP\ T}-RP_{FR\ T})/(RP_{FM\ T}-RP_{FR\ T}))$$

Thus the foot never quite reaches the impediment and, in fact, does just what any normal walking person would do when encountering such an impediment just beyond his landing plane i.e. avoid the overswing of the landing plane in the first place to avoid the impediment (except that the program never forgets to look out for it). The adjustment change variables have been mathematically directed to avoid the obstacle and return the foot to the proper location without destabilizing the user with sudden stops and starts. All the math makes the switching scripts option look even better but, in practice, there is usually the need, even with script switching, for adjustments for terrain that falls between the characteristics of scripts and this process provides that control.

Case C. The impediment appears as scanned to be before the scan reaches the landing zone: Note that the length of the effective landing zone is calculable by scanning the script frames. If the user is climbing steps it will begin with the frame where the square wave first indicated the step and end with the location of the most anterior portion of the foot comes into contact.

Sub Case 1: There is a square wave (this is a step which is optionally verifiable by a) the script if the user is running a step script and b) using step recognition of the anterior scans (steps can be recognized ahead by the distance sensors as the swinging foot scans the area for up to several feet ahead of the user such that the program knows when the next stride will encounter a step) or c) a square wave was sensed in the current frame or d) all 3. This is a step that is a little higher than anticipated. Thus the true landing zone is being identified incorrectly as an impediment. Raise the foot either by creating and managing adjustment variables, switching scripts for the rest of this cycle to a higher stepping script or both.

Sub Case 2: The impediment's height and position are such that they will not reach the arc created by the foot in the positioning swing. There is nothing to do since they will already be stepped over.

Sub Case 3: The impediment's height and position are such that they will reach and impede the arc created by the foot in the positioning swing. Raise the foot as above either by creating and managing adjustment variables, switching scripts for the rest of this cycle to a higher stepping script or both. If adjustment variables are used to raise the foot prior to encountering the obstacle, they should, ideally be managed as in Intra-Script Balancing described above i.e. the changes are graduated and reversed in a graduated manner after passing the impediment to return the foot to the correct attitude.

Adjustments: Landing Zone Height Lower than Anticipated.

Case D. Negative Impediments (Depressions in the Terrain):

When the landing zone is lower than anticipated

Also do lesser value where you switch to a less high-stepping script if it has occurred for 1 or 2 previous cycles Assumed: Sensor 1 returns a closer value than recorded for the frame.

Trend Watching Controls: In many cases above, the script may have been switched to accommodate terrain. This goes both ways as a smoother terrain with no impediments can automatically switch to a less high stepping script. This can be done either immediately when a new cycle recognizes a larger than needed clear area or the program can require that this condition continue for several cycles before switching back to a less forgiving low stepping script to reduce the number of changes.

Special provisions for climbing steps. When the sensors pick up a square wave indicating a step, the program can adjust foot position forward or backward based on the position of the square wave now as compared to the script. The position in the scanned landing plane of the original (model) square wave in the script can be calculated on the fly by reviewing the scan portion of the script. However, the script can also contain the location of the square wave in the action cataloging sequence in the action.dbf table which eliminates a calculation. Either way, if the currently measured square wave is x mm to the anterior of the recorded square wave, the foot will be moved x mm forward of the frame demanded position so that the edge of the step encounters the foot at the modeled position on the foot. Because alignment with steps is rarely perfect and because steps often spiral, twin sensors on each side of the foot in the scanning process make it possible to observe a difference in angle of the line of the square wave. If the angle of the edge of the step (seen here as the angle of the square wave line assumed between the two points scanned by the twin sensors encountering the square wave) appears to have a relative yaw of −5 degrees, the program can either:

a. Effect an adjustment process. This can be accomplished by effecting an additional relative yaw of −5 degrees on the ankle while the preplanted foot is in the air and then, once in firm contact with the step based on milemarkers and contact sensors and as soon as the other foot is out of contact with the previous step, and then rotating the now load bearing foot +5 degrees thus returning the foot precisely to the script's yaw (centric) and the body to the desired body yaw. This has the effect of twisting the body supported by that foot in line with the step while returning the body to the script's positions. For large angles that would push the limits of joint mobility, the same feat is accomplished by moving ½ the degrees of travel in the wrong direction and then the full correction which required a mobility from center of ½ as much.

Or b. Switch to another script in the sequence for spiraling steps. These can be switched in and out seamlessly such that if the stairs spiral at a continuing subtraction of yaw of 7 degrees and the action cataloger only created scripts for 5 and 10 degrees, the two scripts can be alternated in a closest match process to achieve the desired effect. Or c. Both. This allows better full body modeling and flexibility as well as fine tuned adjustments within the scripts. As illustrated in ExecuteScripts above, between script changes (which are ideally, for maximum smoothness, limited somewhat to nearby transition points), intra-script corrections are made between the changes of scripts which, depending on where the ideal angle falls, either makes one script work or smoothes the transition between them.

Thus it is frequently advantageous to use both. The script switch to get very close to the ideal script and the intra-script adjustments to fine tune.

Roll Adjustments. In a like manner, roll is controlled at the first level intra-script by adjusting the inside and outside ankle tendons to accommodate landing zone roll that differs from the current script. Script switches to a script with a roll closer to the current landing plane's roll, while not needed for most terrain and situations, is a useful means for dealing with extreme rolls that significantly effect the whole body. For example, if the user entered a roller derby on a highly banked track an appropriate script is the obvious choice.

When the automatic monitoring software senses a significant difference in the recorded script value and the one being returned currently, calculations are executed which create adjustment variable values that endure for different periods based on which sensors initiate them. Adjustment variables created in response to foot based sensors like those above and the landing plane calculations can be maintained and included as part of the calculation (added to the frame demanded joint angle value) as long as the foot sensing the condition remains the active foot. This allows slower sensing equipment's responses to be effective over a number of frames. However faster equipment is increasingly inexpensive and compact and, as described in this simple example embodiment, it is very effective to do a complete recalculation of needed adjustments with each frame (where adequate refresh of data is available) thus creating new adjustment variables to be used in the calculations for affected joints. Similarly, adjustment variables created in response to general body attitude sensors (like the torso mounted attitude sensors) are continually adjusted based on current reported general attitude values as they compare to recorded values.

In addition to and, where implementer desired, in combination with the intra-script adjustments (which adapt to circumstances without changing the script), inter-script automatic responses, where a new script is transitioned to by one of the means described above, provide the power to make massive changes in plan that an intra-script adaptation cannot make without the destructive complications such as the destabilizing effect of wholesale changes even to the point where they would, but for script switching, overpower the automatic balancing and other stabilizing controls.

Inter-script responses: To shift "gears" to the new script at an adequately parallel point in the stroke, this example embodiment moves first to the most logical record based on percentage of stroke finished or milemarkers (if available, they are not required). In the code snippet of a sample embodiment above, ExecuteScripts, simply calls the Transition program which simply checks the current script record image to see if the record is marked as a good transition point. If it is, it returns .T. and the script switching is permitted. The many obvious programmatic alternatives include testing for percentage of stroke completed, various points that are ideal and a couple that are least favorable to switching and using those criteria to determine when and if to switch scripts.

With the gears thus shifted (i.e. now that we're following a script more reflective of the terrain), all the other joints of the body will move into more appropriate position for the terrain. A rich set of parallel scripts or equally functional parallel programmatic processes with comfortable switching points will minimize or eliminate (depending on the number of scripts and the precision of the cross-entry points) any transition jerking. However, where this is not the case or in cases of unusual or large transitions such as automobile entry from standing or fall recovery scripts an intermediate morphing script or process to the positions of the first step of the new script or process may be inserted into the transition process by simple script ActionCode reference or programmatic control. In this case (increased incline), the user will be caused to lean forward more, incline the ankle joint to point the foot more upward and, in steeper incline scripts, bend the knees more as was modeled or programmed. This will all be natural and coordinated since it is matching a script modeled after a person comfortably negotiating a similar incline. This script switching can, of course, be done as much as is needed as a means of balancing. This switching of scripts can be manual or effected automatically which increases the smoothness of the transition by increasing the number of scripts in a family since the program can respond more quickly and often than a human user can do comfortably.

In addition to having a script series like the series above, you can have parallel series with terrain or other adapting characteristics. For example, if the user were on script 21 of the basic walking series just discussed (on a significant incline) and a rougher terrain was observed by the user (when this is being controlled manually by the user) or when the sensors picked up close proximity impediments (where they were not in the script for automatic script switching applications) the switch could be made instantly to script 21 of a parallel "high grass stepping" series picking up at the same milemarker position in the new script. This allows single keystroke or automatically sensed and effected transitioning to an equally "full-bodied" script (appropriately directing all affected joints) that is tuned to the appropriate incline and also best adapted to the terrain.

This shifting from one cyclical script to another as a means of adjusting to the environment and maintaining a steady balance has a number of other advantages not the least of which is that this script also "knows" the various body attitudes associated with a stable condition. Thus, this script which is better attuned to the conditions is able to recognize (by comparison with a known experience) and identify a problem and address it.

Responding to dips and bumps on landing zones: Although there are numerous approaches, a sequential approach beginning at where the rubber meets the road (the "shoe sole") is described here. This process includes adding to or subtracting from the scripted positions to accommodate the very local change in terrain. But it only modifies it while the foot is in contact with ground. As soon as the foot leaves the ground, the ankle, etc. return to the script's positions. There are also additional controls that can be effected at the ankle and above. For example, if the user places the heel of a foot on level ground but the front ball (by the toe) sensor doesn't touch ground as expected in the script because there is a slant down in the pavement, even though the lower leg is not yet out of it's desired position, the MoveBody program will create intra-script adjustments to extend the ankle which points the foot further down looking for ground just as a normal walker would do. This action was based on the front foot pressure sensor and can prevent the need for any further action from the sensor on the lower leg by keeping the lower leg where it belongs. Of course, if it contacts ground too quickly, it similarly points the foot (toe) upwards at the ankle to prevent stubbing the toe and possibly tripping.

However, if the change in incline or terrain as sensed either by the sole pressure sensors (as compared to the script) or the lower leg attitude sensors, is beyond the ability of the ankle and, optionally, tendons above the ankle to adjust, the hip and upper body will be at a pitch and/or roll different from the script. and thus the hip worn, vertically mounted attitude sensor senses a change in directional vector speed, the waist tendons are, operating independently of the ankle controls, used to balance from the waist to return the area below the waist to the script's attitude.

Thus, when in a balance sensitive standing or walking activity, extended balancing code can be activated which controls motion at the waist. There are many complex but obvious means to manage balance including those involving programmatic controlled adjustments of multiple limbs. However, in this sample embodiment, to minimize interference with other preprogrammed limb actions, only the user's waist joint (which functions like the wrist joint above with 4 position offsetting tendons) adds to or subtracts from the scripted angles to respond to out of balance conditions sensed as described below. In the simplest embodiment, if the user was walking uphill causing an out of balance situation, as data is compared to the recorded relationship with the central focus of gravity or otherwise sensed, the waist would be bent slightly in excess of the recorded values for the waist until the appropriate attitude below the waist is attained.

However, where even very localized terrain aberrations exceed the capacity of intra-script corrections supported by automatic balancing to manage, a safer, rough terrain, deep stepping script is switched to. This is illustrated in the example code embodiment ExecuteScripts as TerrainAutoCk is called to create adjustments but has the option through a responsive return of the passed parameter NActCode to force a new, safer script.

Step recognition and Auto-Positioning: The image scanned by the foot sensors and/or other distance sensors can recognize the square waves of steps ahead. The square wave refers to a scan (for example from a foot mounted distance sensor as it swept from horizontal up passing the first step of a staircase) over a vertical plane, such as the facing of a step, (with the predictable and only slightly changed distance throughout the planar part of the scan and the predictable relationship of the distance with the tangent of the current angle) suddenly followed by a longer distance. For efficiency, the sensor data history is continuously compiled and stored in push-and-pop memory registers (which keeps the last x readings and discards the oldest when a new one comes in) by a parallel process for quick access with historical context. Thus, for example, when PreStride is called by ExecuteScripts, it can scan the most recent distance readings and recognize a square wave by the predictable distance sensor pattern of a vertical planar target followed by a sudden change to a deeper distance. If that second distance is in the depth range associated with steps and follows a planar scan characteristic then the depth of the step is known and usable for automatic response. Other body mounted scanning sensors do augment the foot sensors. However, the user can also be the preferred source of warning of upcoming steps using any of the user interface tools above. A practical combination of the two is for the user to signal upcoming stairs and the equipment to only then be responsive to the special sensitivity to sensor readings, etc. related to the automatic user support described below. When the user and/or the equipment warns of upcoming steps or curbs, the processes below provide a means to handle many of the walking details for the user.

a. Distance-to-target automatic adjustments: This can be used to calculate the distance to the steps and adjust the walking script slightly so that the user doesn't have to make any manual positioning adjustments when he gets to the steps before switching or autoswito a step climbing script. That is important since the foot must be positioned properly before beginning a step climbing script. If the user was off by a half a step he would miss the step altogether and manual adjustments or "baby steps" to get into position for mounting steps is comparatively tedious. If, for example, the user indicated by a click on the oral keyboard that steps were directly ahead, the distance can be programmatically calculated. One means of distance calculation is from the current distance indicated by sensing means at the part of the stride where that sensor's pitch is near 0 and it's distance from the ground is 1 to 4 inches from the ground. Another of the many applicable means of measuring the distance is by simple triangulation based on head attitude as the user places the crosshairs of the visual display on the middle of the vertical plane of the first step. Then the distance to the upcoming steps is:

$$\text{Distance} = \tan \theta * H$$

where $\theta$ is the inverse value of the head pitch (which is negative when looking down as is normative for this application) thus $\theta$ is the same as the angle between the vertical line through the user's body defining the user's height and the line from the user's visual means and the target (first step). H is the y attitude value of the head-mounted attitude sensor (which can be adjusted for position of attachment on the head and can also be replaced by the user's adjusted height). This distance is, of course continually recalculated as the step or curb is approached and the approach modified to fit it since a staircase is rarely approached from a perfect perpendicular even when the user is guiding it smoothly by controlling head yaw.

With the distance thus calculated by either or both or any other means, the program simply determines by algorithm or simple calculation how much to increase or decrease the length of the stride which will then be effected through any of the stride adjustment means. One such example calculation in common programmatic form is below: NS, the normal stride for the script, is 14" and T (tolerance), the amount we can stray from that amount without causing problems that intra-script automatic adjustments won't easily handle, is 3", CS is the length of the current stride and D is the distance to the first step or curb.

Function StrideCalc
   * called by Crosshair which is called by ExecuteScripts. Also routinely called by
   * PreStride for background intra-script stride adjustments when Continuous Distance
   * Sensor Check has been turned on by the user for adjusting gait to upcoming script-
   * changing elements or obstacles automatically without requiring user input.

```
Parameter D,CS,NS,T        && Parameters sent from calling program
Remainder= (D / CS) - INT (D / CS)
if Remainder = 0
   exit    && already perfect
endif
Steps = INT( D / CS)       && calculate best tolerable gait length
NewStepLen = D / Steps
ShortStepLen = D / (Steps + 1)
LongStepLen = D / (Steps - 1)
CS = 0
if abs(NewStepLen-NS)<abs(ShortStepLen-NS)
```

-continued

```
and abs(NewStepLen-NS)<T
   if abs(NewStepLen-NS)<abs(LongStepLen-NS)
      CS = NewStepLen        && NewStep is least adj amt
                              and in tolerance
   else
      if abs(LongStepLen-NS)<T
         CS = LongStepLen
      else
         CS = NewStepLen
      endif
   endif
else     && NewStepLen is worse or out of tolerance so ShortStep is one
to beat
   if abs(ShortStepLen-NS)<abs(LongStepLen-NS) and
   abs(ShortStepLen-NS)<T
      CS = ShortStepLen
   else
      if abs(LongStepLen-NS)<T
         CS = LongStepLen
      else
         CS = ShortStepLen
      endif
   endif
endif
Return CS                  && returns the new stride length
```

This ability is also applicable to any other application where a specific point needs to be identified and precisely approached (without concerning the user) as a transition such as from one script or process to another.

b. Automatic adjustment of tangent to line of step to be climbed: The program, recognizing the angle of the line of the square wave by comparing the distances recorded by the left sensor and the right sensor (optionally on both feet to broaden the lateral differential for a more accurate angle calculation as the square waved scanned line progresses) and then triangulating, can automatically adjust yaw, using means like those described above, so that the user's yaw with respect to the step perfectly reflects the script's at the point of mounting steps, for example (which typically has the user perpendicular to the step). One means is the intra-script adjustment by foot-rotation above to reflect the desired change in yaw by rotation of a planted foot using ankle and/or thigh rotators as well as optional stepping-out and stepping-in procedures to achieve the rotation of the body the number of degrees required to make the angle to the target 90 degrees.

By combining the above, the current invention provides means for a user to give only general yaw directions, such as the direction the user looks towards (head yaw) and manage complex routes with changing terrain, obstacles and spiral staircases.

As described above, the user can indicate through a variety of user interface peripherals an upcoming step up and even have the system approach it precisely, smoothly and at a perpendicular angle. Additionally, the current invention provides means for automatic step recognition and close-quarters (while on the steps or right at the first step) response using distance sensing means or other distance calculation means to determine just when to automatically switch to a step climbing script and when to return to a walking script. This provides an element in an autopilot mode where the system is pointed (yaw directed) by the user and the rest is done automatically until the user intervenes with an adjustment tap on a key, changes a script or cancels the current script to make manual adjustments.

When a walking script or procedure is being executed, the anticipated distance ahead of the foot is known. In a typical action cataloging session of a walk on a relatively flat surface, for example, that distance at a point where the sensor's pitch is effectively 0 and altitude is just a few inches (known by attitude sensor reading and/or simply by where the user is in the script, i.e. SeqNumber) there is nothing anywhere near ahead and the reading can be set to a large default number by the action cataloger. However, when a user is following that repetitive script and approaches a 4" curb, that reading (distance) will be close and recognizably different from the scripted value. As the advancing foot that houses the sensor array continues forward and upward, a sharp, square-wave increase in distance will indicate the edge of the step. Since the measures being considered are themselves distances, calculation of the height of the first step to be overcome is elementary:

$$Height = D_1 * \tan \theta$$

where $D_1$ is the distance of the sensor reading in the timeslice just prior to the square wave and $\theta$ is the sensor's pitch at the same point. The value of $D_2$ (the distance just after the square wave) also tells the system whether the approaching obstacle is a curb (1 step) or the first of a series. The height data is used by both the intra-script adjustments (to determine how much to raise or lower the foot to land on the step) and inter-script adjustments (to pick a script for the particular type of step) in TerrainAutoCk (called by the example code ExecuteScripts).

The calculated depth of the steps:

$$Depth = D_2 - D_1$$

also provides the data needed by PreStride (called by ExecuteScripts) for both intra-script adjustments (how much to extend or shorten the stride to avoid tripping on short steps or missing the next step on deep steps) and script selection for inter-script adjustments. Similarly, monitoring the distances allows the processing means to know when to have the current invention resume a smooth walking stride. Other applications of distance sensing as applied to script switching and process intervention are disclosed elsewhere herein including applications to trip and dip responses (trip prevention over obstacles and managed responses to sudden dips).

Some necessary balance adjustments have nothing to do with terrain. If the user is a little more top-heavy, for example, that the action cataloger, the attitudes modeled may need adjustment. Using one of the user-interface means described above (such as the head-attitude driven upper-attitude device), the user can correct (override) an out of balance condition as a script or procedure is being practiced. Naturally, these necessary balance adjustments based on experience in a controlled environment can be programmatically saved by simply saving amended angle data (or other position information for other embodiments) over the original setting in the Positions.dbf table record for that joint in that timeslice (SeqNum) of the script being executed. Thus equipment can be automatically tuned to the individual user without programming or extensive professional help. Either the actual angle used (as amended by the user to keep balance) can be saved in the Positions.dbf table over the originally captured value or a calculated value can be overwritten to gradually tune the system to the individual. One calculated value means is, for example, when waist bending alone is selected by implementers as the user directed balancing means, to change the NewPosition value by $\frac{1}{4}^{th}$ the difference between the scripted position of each of the 4 waist tendons and their actual position in the last use. Thus, since, after each use the new values are saved in the NewPosition field. Thus each test pass would servo towards a norm without allowing any single use to have an excessive effect on the modified script. Retention amounts, because they will be added back with execution, are, of course, not included in the saved values and obvious means can be used to allow repetitive scripts to be run many times and the results averaged to smooth out one-try aberrations.

In either case, this provides the facility to know immediately when an out of balance condition is a problem and to remain in balance when unexpected circumstances occur. It also tunes the Positions.dbf table to accommodate consistent user reticence that might hinder actions (requiring learned system adjustment) and when the user and action cataloger simply have different weight or other body characteristics.

The current invention is even applicable, in a passive-until-needed version, to the provision of a safety net that protects people who are able to walk normally under their own power but are subject to sudden loss of strength, stumbling, fainting or spasms that can result in falls and other damage. Here, the actuators simply remain disengaged from the joint control points or the tendons or other connectors that contact them until they are needed. The joint position sensors, however, are never disengaged so that the processing means always has access to current position information. One such embodiment is a tendon-based system along the lines of FIG. 11. However, the larger, lower (as viewed) wheel of the joined wheel-set, is connected to the smaller rotary gear by a solenoid driven or otherwise switchable clutch as is commercially available which disengages the larger geared wheel from the smaller and thus separates the tendon cable from the hydraulic piston for normal, unfettered use. This allows the tendon cable to move freely only slightly resisted by a coil spring attached to the casing and the lower, larger wheel making that lower wheel action and the rolled tendon not unlike an old-style window shade return. The processing means decides that help is needed based on any one of multiple possible conditions.

Script based protection needed sensing: For example, even when passive the assistive clothing can track action "loosely" along a script. In other words, the software, as usual, cyclically passes through a specific, repetitive script (walking, for example). However, in passive mode the user determines where we are in the script instead of the other way around. The software first identifies the basic kind of action being taken (examples: walking, climbing stairs, standing and sitting). This is pretty easily done by considering in basic case logic the body attitude, waist position and relative position of the two feet with respect to each other. When, for example, the case logic first determines that the user is walking, it selects and switches to a basic walking script and skips down to a point in the repetitive, cyclical script most congruent with the current body attitudes and joint positions. Rather than making this script-location-pointer task difficult, the software uses a quick index seek and some simple case logic to instantly locate the record in the script table sequence for that particular joint-control point with the value for NewPosition closest to the one that actual knee joint-control point is currently reporting.

Example: Our objective is to pick the right script for what the user is doing and then find the right point in that script. This can be done with great speed by processing means but several values have to be calculated or acquired to do this. In one applicable calculation embodiment used as an example here, these values are:

Is user in Flexion or extension, what is the user's current stride length, what is the current terrain type based on the user's current gait, and what is the user's current change in yaw over the last timeslice (or averaged over the last few).

Is user in flexion or extension? The software that is tasked to synchronize the user's current gait status with a point in the walking script easily ascertains whether the user's right leg is in flexion or extension phase simply by comparing the last few readings over time from the position sensing means for a key joint or joints. Here we will use the joint-control point on the posterior-interior thigh-to-waist tendon. If it is in flexion, the last few readings will show retraction over time (position numbers becoming smaller over time) and the software will determine the global logical variable Flexion to be true. If not, the software will determine Flexion to be false. This is helpful because it is not enough to find a point in the gait sequence where the right leg is in a certain position. To be sure we're at the right point in the script we need to know if this is that point passed in flexion or that same point passed in extension.

What is the user's stride length? As mentioned above, the sensor's values are placed in push-and-pop historical memory registers by a special utility for faster access of current and recent historical information. By obvious means the recent record with the maximum point of flexion and the record for the maximum point of extension for a key joint or joints (here we will just use the anterior tendon control point of the right knee) are found and the difference in these two values is the stride length of the user's current natural gait. This falls into a range used to create the stride length values used in the AttitudeGuidance table used to select scripts in ExecuteScripts above. For this example we will assume it falls into range 4 (a moderate stride).

What is the terrain number? Similarly, the maximum altitude of the right foot sensor falls into a table-matchable range for terrain (the higher the stepping the higher the terrain number in the AttitudeGuidance table). However, where the user prefers not to wear that sensor on the feet, the maximum recent retraction of the right inside anterior thigh tendon provides a value usable for point of maximum foot altitude comparable to a table of those heights for the table selection of the user's current terrain. For this example we will use terrain="1" (moderate to uneven).

What is the user's current change in yaw? Then, the change in yaw between the last 2 timeslices from the sensor memory registers provides the user's current change in yaw in process. We will use 0.5 change in yaw (even if there is no record in AttitudeGuidance for this fractional value we will set "set near on" which will return the value closest to it and yaw is the low-end order criterion so it will not interfere with the seek on the other values). Then the following code can execute:

right foot landing and then the cycle repeats from the first record in the cyclical script again. Thus, if there are 200 records in the script and you are only considering, for simplicity, the right leg (which is practical), and you want to know if a given record showing a joint-control point position of A (indicative of some joint angle) is in the process of flexion or extension, this can be easily done by dividing the number of records by 2 and comparing to see if the SeqNum for the record you are on is greater than or equal to that number. If it is, the software will assume that the script record is in the second phase of the script (extension). If not, it will assume the record is in flexion.

The Positions.dbf table has an active index named FindPlace.idx sorted by ActionCode+JointNum+NewPosition+SeqNum.

Thus, if the script number (ActionCode) is 7654 and the name given to that joint-control position is 123 and the current upper anterior knee joint-control position is 1111.11 units then the software would simply perform the following commands:

```
SELE POSITIONS
SET INDEX TO FINDPLACE.IDX
SET NEAR ON && finds the closest matching record
IF FLEXION
    SET FILTER TO SeqNum < Midpoint
ELSE
    SET FILTER TO SeqNum < Midpoint
ENDIF
SEEK "7654123111111" && locates a record comparable to user's point
of gait
SET INDEX TO && release index. Other code uses difference sequence.
SET FILTER TO && kill filter
```

(Of course, this code is intended only to describe in a generally readable form the practicality of this application of the current invention and, for real programming elegance, faster code may be written including an index that already reflected the filter, etc.)

It is also a valid embodiment of the current invention to select scripts based on timeslice. However, in this example embodiment, the user's motion of the key joint control point

```
Select AttitudeGuidance
set order to AttitudeChange
CY = str(Y,10,2)              && this time y (yaw) = .5
Direction=sign(y)             && since yaw is positive (.5) it's sign and our direction is 1
Stride=str(StrideLength,1,1)  && here stride= 4 and Terrain already in string form as "1"
Set near on                   && finds closest match
seek Terrain + Direction + Stride + CY
do pickscript with AttitudeGuidance.ActionCode
```

The matching script is now open. Now the task is to find the point in that script parallel to the user's action.

Finding the right point in the script: In a cyclical walking script which is our example, because bipedals require an off balance condition to launch a walk, a quick "launch" cycle is typically included which can be a separate script that calls the repeating walking script which begins at an already off-balance point, for example precisely at right foot landing (end of extension for the right leg). This cyclical script will then, from the top, spend ½ of it's records in flexion achieving the point of left foot landing which, for the right leg indicates the end of flexion. The remaining ½ of the script represent the extension cycle for the right leg with said records taking us just prior to (in walking we used the posterior-interior thigh tendon) divided by the recorded timeslice for the script that best meets the other criteria is simply multiplied by the script's timeslice to obtain a calculated timeslice that is actually used (and is recalculated, for better accuracy and responsiveness to user changes with every stride).

When the assistive clothing is in passive mode, the software can continually re-find the current point in the script or, having once found it, follow along. To save space required to show how it could be tracked, in this illustration we will just let it continually re-find its position. However it is also practical to simply follow the script, making intra-script intra-stride corrections as necessary as illustrated above.

Thus, at any time in passive mode, the controlling software can know very closely where the user is in his script cycle. It is not imperative that it be absolutely precise because small timeslices make for small errors and we're dealing with ranges of tolerance anyway but the ability to be very precise is, nonetheless, there. Also, after the script location is identified, the index is reset to normal sequence number order. Thus, the software pointer is located in the natural point in the script for the user's actions which provides synchronized data on all joints (not just the right leg).

Now, each time the software relocates the appropriate point in the script, it has a wide array of information to indicate if there is a problem. In this current example the response is to call a stable position script and enforce it in normal (active i.e. non-passive) mode. However, the implementers or user could elect in such circumstances for the mode to simply switch to active and enforce the current script overriding any short spasms, etc. This is most appropriate, of course, in stable standing (where, with intra-script balance control a standing user in a spasm or when tipped slightly can simply maintain essentially the same pose), sitting and other already largely static positions.

Thus, by comparing key joint-control point values (such as those assigned to the knees and ankles) in the script (NewPosition) with the live reported values from those joint-control points within a tolerance, a slip, trip, bump, lower body spasms (since we chose lower body indicators in this example), etc. are quickly identified.

The length of the stride is not as key as it appears. If, for example, a shorter stride than the script calls for is being executed, even if the software chooses not to simply switch to a shorter stride script, the points in the shorter stride already reflect the middle area of the longer stride script (where the feet are closer together). Thus, the repeated search for a short user stride in a long stride script will be pretty successful in that it locates a point in the stride script where the body attitudes, particularly from the waist down, reflect those of the user. Intra-script corrections, as shown above, create adjustment values that in normal use would adjust the positions forced upon the user. Here, however, they are used to reconcile the script to the user. For example, if the user's stride is actually a bit longer than that for the script chosen (or if the user is just varying a bit from time to time in the normal gait), the intra-stride intra-script adjustments are still placed in arrays or other memory means as above but are now combined with the current user readings to compare with the static script. Thus, the current user status plus the appropriate value in the stride array is comparable to the scripted values and, if that is substantially untrue in the next timeslice it is calculably obvious simply by comparing the difference with a norm that something is wrong. If the new action fits no script, a corrective (stable position) script is effected as described above.

This ability to find a rich set of body attitudes and device readings, etc. that should be present, within tolerance parameters, at a point in the gait allows those tolerances to be set much smaller (tighter) than a more generalized approach which can make this approach much more sensitive thus catching a problem faster and more reliably.

However, because the correct positions of so many joints are known and because so many are affected by spasms or bumps and because there are additional means for sensing them (belos), these tolerances can be set very loosely and still be extremely effective in recognizing a problem quickly and before it has progressed too far.

Other means of recognizing a problem do not require the position in the script to be known. For example, by comparing 1. the change in position over time (speed) of any given joint-control point with norms for that joint-control point and/or
2. the pressure and change in pressure on a joint-control point with norms for that joint-control point By simple comparison of attitude sensor and accelerometer provided data with norms that can be effective even when not context sensitive, as they were above (for example a sudden jerk or an attitude combination of head and body with both beyond a vertical norm and without the other evidences of that being appropriate (such as the body attitude of someone sitting into a chair which does have an advanced head attitude but has a recognizable upper-body accelerometer reading towards a seated position and a lower-body accelerometer sensed rotation of the lower body), the software can recognize spasms, falls, fainting etc. and enlist the assistive clothing to rapidly engage and protect the user by switching to a stable position script even when a script has not yet been identified to match the user's actions or, optionally, when script matching is not being used at all.

When a problem is indicated, stepper based or similar actuator approaches can immediately begin to follow the morphing instructions of the software to a recovery position which can be the first record of the thus called recovery script. Tendon based embodiments, however, with the addition of clutch and spring as mentioned above, have to first advance the piston to the appropriate position for the current joint-control point value before it engages the clutch because, unlike rotary based actuators such as stepper motors, the stroke length is typically limited.

These recovery scripts, as described elsewhere, will typically assume a more crouched position with wider stance which is automatically modified as needed with intra-script adjustments responsive to foot sensors, etc. such as continuing to lower the foot beyond the anticipated ground-contact point in the script if contact is not sensed as described above. Since this process is sensitive to current action type (walking, climbing stairs, etc.), a different recovery position and/or script is available for each action type. However, even the general purpose default recovery positions for non-context sensitive recoveries can move to stable, full-foot-contact positions and then auto-balance using the interscript terrain and balancing adjustment processes described above. However, more elegant and much less noticeable recoveries are practical with context sensitive (script-followed) responses. Thus, when climbing stairs the recovery position can be more accurately context tuned to involve less left-right stance expansion and more leading foot ascension, responsive hand extension and waist contraction. Obviously, this protection is always available to non-passive assistive clothing users as well.

Similarly, assistive clothing provides means for protecting users from the joint degeneration that is commonly associated with altered or aberrant gaits due to injuries, arthritis or simple aging. The active assistive clothing user always maintains a proper gait because the assistive clothing determines the gait to a largely passive user. Also, however, to an active user, a normally passive version of assistive clothing can provide the same protections from defective gait.

Using the means described above or any of the many alternative programmatic and device supported means for locating an appropriate action script and a congruent position in it relative to the user's current activity and keeping up with or following that script as the user walks, etc. all of which are applicable to a variety of similar applications of the current invention, the assistive clothing can passively, as in passive fall and spasm protection above, "jump in" when needed to correct a defective gait. The assistive clothing's software, following the progress of a user through a congruent script, continuously compares each joint's positional data against that of the script's NewPosition values to obtain a difference. That simple numerical difference is then compared with a tolerance that may be, by implementer preference, a general set of norms (like a percentage of deviation) or a table of norms with a tolerance unique to each joint within each action type. If the difference in the current position with the recorded congruent position in the action script exceeds the norm tolerance, the assistive clothing engages (in the embodiment described earlier the actuator clutch engages), quickly moves that joint to the appropriate position and then, typically, immediately disengages.

Short timeslices and quick sensing of errors results in tiny adjustments effectively providing a motion channel that the user is required to stay within the limits of but that is unnoticable when the user's gait is proper within the norms. Note that, although the assistive clothing can simply adjust only the offending joint-control point, it is typically better for all the joint-control points for the affected joint to be simultaneously readjusted to the current positions indicated by the script. Normally, of course, since all of those joint-control points connect to the same joint, a mis-position in one always affects the opposing joint-control point and usually affects all the others anyway making a full adjustment of all points on the joint the preferred embodiment.

Also, although applications exist where longer persistence of interference are applicable, in this example use, the assistive clothing, acting on very short time slices, simply makes minimal adjustments (by catching the error before it gets far out of line), disengages and repeats the testing process.

Obviously, the smaller the tolerance settings the less passive the assistive clothing becomes. Set to 0, it might as well be active since human gait tends to vary a little. This provides an easily software scalable facility for not only preventing damage from a defective gait but also providing an easily scalable means to teach a good gait. The better job the user does following the physical therapist's prescribed gait, the less the equipment has to interfere.

Also, the assistive clothing can be equipped with sound, electro-stimulation or other interruptive means to indicate to the user that his gait slipped out of bounds and even help correct the gait without actuator interference. While this alarm and response is applicable to the normal assistive clothing assistive support function and the normally passive functions above, it is also applicable to embodiments of assistive clothing without active actuators, i.e. where the position tracking means are intact but there are not necessarily any actuators or, in some embodiments, there are not even any mechanical push/pull joint controls. This can be a much less expensive system and less constraining while being applicable to some who don't need support but only guidance and, optionally, a corrective stimulation where needed. One easily described embodiment involves the actuator of FIG. 11 with the cable, large wheel and spring assembly (in or beside the large wheel) described earlier but without the hydraulic actuator, clutch and gear. Thus, the tendons attached to joint-control points move easily (and cheaply) pulling only against a slight spring-load in the large wheel of the tendon and turning a position counter to keep the processing means apprised of the joint's current positions. Alternatively, other body-attachable joint position reporting means including but not limited to simple bend-indicator strips (or arrays of bend-indicator strips) over bend points in a joint which can perform the same joint attitude reporting function completely eliminating, where it is not needed for support, all joint control hardware.

Thus one embodiment providing a means for modeling ideal scripts and tracking a subsequent user's actions against them and/or comparing sensor values against norms for the purpose of sensing out of tolerance conditions applicable to the identification of defective gaits, both for modeling scripts and as worn by users, requires only processing means operatively connected to joint position sensors.

The passive warning sound and/or stimulation is useful in training the user even if the assistive clothing is completely passive (disengaged) as it continuously warns the user immediately upon digression from the appropriate gait which is particularly useful (and non-interfering with sudden non-standard or frivolous actions) after the more intensive training is successfully completed.

In addition to any form of recognizable alert such as a beep, for example, to warn the user of a defective gait, out of balance condition, etc., the software can, in addition to actuator response or, alternately, instead of adjusting with actuators (in a passive or non-existent actuator embodiment), correct the gait by electronic or other stimulation. Although there are any number of software means to support this hardware intervention, one such example is to inquire a simple table of stimulation responses for each part of each joint. Research has already established means to selectively contract and relax muscles and these, as well as new and refined data coming in regularly, are easily edited, maintained and used in a table based structure and/or an obvious programmatic process. Thus, for example, if the script requires a positive flexion adjustment of amplitude X on the anterior upper knee joint-control point (even without actuators it is convenient to use the same key joint control point location identifiers), the table record for that joint-control point's positive flexion response would indicate the proper (by effective locations) electrode(s) or other stimulation means to be implemented while the amplitude of the stimulation, which is relative both to the joint and the amount of correction needed (difference calculated between ideal and current position) can either be table driven or purely formulaic and optionally accuracy-refined by reference to a joint-control-point-load table indicative of the comparative loads upon each joint-control point at each point in the gait of the current action.

Thus, using norm-comparison and/or the script tracking and position comparison means already described to determine desired joint position changes to eliminate the thus-calculated differences from the scripted norm in coordination with tabular data and/or formulaic calculation of what stimulation point or combination of points when stimulated effect the desired force on that joint-control point, the current invention can, optionally without actuators or other active hardware control, enforce a healthy gait and protect the user from falling.

An alternative method uses a script or process that, instead of (or along with) using actuators to effect joint control, muscle/nerve stimulation is used instead. Using the same table structure as with normal actuators, the joint-control positions, etc. are handled the same way except that the means for achieving those scripted and tracked positions is by electro-stimulation replacing, for example, anterior thigh muscle stimulated contractions in place of anterior tendon retractions. Hybrid embodiments include a shared effort exists between muscle support and actuator support. Here, based on a wide variety of implementer chosen criteria, the power required to move the joint to the desired position is provided by the muscle with the actuator making up any shortfall or other shared effort embodiment.

This process can also, even without the spasm protection provided above from context-sensitive actuator stabilization, protect the user from injuries and embarrassment caused by spasms by offsetting those unscheduled motions with proactive spinal, nerve and/or muscle stimulation. A spasm is by definition an aberrance from a normative walking gait or other activity (including sitting) and, by enforcing that gait proactively with stimulation as described above, those spasms are controlled. The more violent the spasm, the more difference between the norms and the actual positions in the tiny time slices being monitored and thus the stronger the resistance thus effecting an amplitude responsive reaction to a spasm of any level. Here again, a hybrid including the shared control of muscle stimulation and the easily controllable, stabilizing hardware actuator adds another layer of smoothness and control. However, the sensor and stimulation alone approach is less expensive and cost is a major factor in the acceptance and general use of needed prosthetics.

Since sitting still, standing still, etc. are also action scripts, script based sensing of spasms can be an effective means to catch spasmodic activity before substantial motion has occurred. There is also, however, an additive sensing means that can be effective for sensing spasms for both mechanically active (actuators used to control spasms) and mechanically passive embodiments that can provide an additional source of problem identification or conveniently allow some of the scripted sensing means to be ignored. Even in a sitting-still script (which can be, essentially, a single Positions.dbf record for each joint-control position effecting a fixed body position with a tolerance for minor motion), it is impractical to script the arms and hands because, even in a sitting still script, humans move their arms, hands and, to a lesser degree) upper body continuously. Thus it will be common for certain areas to be exempt from script-based spasm or fall sensing depending solely on the action type.

Thus, for those with a vulnerability to spasms, a joint-control-point specific and action type specific maximum for acceleration and, separately, speed can be entered into a table or program which, even when a joint is not being monitored for congruence with a script, is, when exceeded, cause for the software to offset the motion by returning, in the narrow timeslice which is effective in smoothing responses, the joint to its previous position in the manner of joint manipulation described above and, unless a non-passive script is being enforced, disengaging immediately (but remaining vigilant in the very next timeslice). If the user's maximum's are set too low, they will be confined to gentle movements but these settings provide an easily scalable means of customizing the sensitivity to the needs of the user. (Velocity is, of course, calculated by the software as the numeric difference in the joint-control point's current position and the script's NewPosition field in the most recent previous record for that joint-control point divided by the length of a timeslice which is determined in the related table Actions.dbf)

Also, in embodiments where sensing means for torque and/or pressure against the joint-control point are present (applicable to tendon based examples and easily added to be part of most other embodiments), similar maximums and/or minimums for these can be set and enforced resulting in an even broader and more effective range of problem sensing means. This is valuable because having multiple sensing means allows the constraints for each to be set a little looser (more friendly) while still effectively sensing problems so that the assistive clothing can correct it.

The user, using any of the disclosed means for user interaction and the many others compatible with the current invention, can turn off, on and adjust parameters for any of the functions including fall prevention, spasm control and gait maintenance and/or support. The user can also use any such means in the current invention to morph to and/or freeze in a stable position. When instructed by the user to morph to a stable position, the software will morph as described above to a stable balanced position (script or process) sensitive to the action type (sitting, standing, etc.), perform any intra-script adjustments required to acquire full support limb contact with the ground and then, with those adjustments in place, correct any imbalance with intra-script balancing all of which are discussed above, and stay there (resist any user or external motion) until the user indicates that the spasm, imbalance or other condition causing the user (or a sensor-driven automatic process) to desire a suddenly stable, fixed position has passed.

Thus a normally passive and even a permanently mechanically passive (no physical actuators) embodiment of the current invention can not only provide warnings to teach normative walking, step climbing, etc. but can also help correct/enforce non-degenerative walking gaits. With adequate muscle stimulation, even these "stripped down" embodiments of assistive clothing without classic actuators can, by responsiveness to normative action scripts, support users by stimulation of muscles to facilitate or enable walking while protecting from falls.

This adds muscle strengthening and a lower level of spinal and supraspinal training or relearning of task and reflex complex muscle actions.

Applications also exist to teach batting, dancing, martial arts, etc. as the user "does it right" the first time every time as precisely as the expert acting as an action cataloguer did when the actions were captured in joint timeslice databases. Not surprisingly, training also takes active, passive and hybrid forms in the current invention.

In passive mode, the user wears adequate sensors as described above for position reporting to the program which is following a script. Unlike passive spasm and fall control, however, here the script isn't following the user's free actions but the script is in charge and the user is encouraged to get in line with the script. When the user digresses from the scripted position by more that a permitted norm (which can be a fixed amount based on joint angle or a context sensitive amount and can be enforced at the joint level such that every joint can have a different norm specific to the script or point in the script), the user is warned audibly, with a mild shock or other noticeable alarm means which may optionally be location of error specific. For example, in a golfing script using electric shock where the right-handed user bends the left (leading) arm too much, a mild shock may be directed to the upper inner elbow area (lower bicep) that is excessively in flexion to not only indicate that a problem exists but precisely where it is. If in excess extension, the stimulus can be placed where those excessively contracted muscles are (back bicep).

However, though that can be learned quickly by a user, the opposite may be more intuitive and equally part of the current invention. Here, instead of stimulating the offending, overworking muscle, the muscle opposing the offending muscle is stimulated. In the same example of left arm over-flexion, the back bicep would be stimulated thus contracting somewhat causing the arm to straighten out more in line with the script. Thus a. the user's mind feels the user's own muscles being caused to do "the right thing",
b. the process "slaps" the offending area singling it out like a good coach and c. capitalizes upon the irritant-avoidance element of human nature encouraging a less irritating swing with each practice swing, and
d. the user consciously and unconsciously knows what muscle should do a little more of what next time (since that is the one stimulated.
e. where the stimulation results in an appropriate muscle contraction, the stimulation itself actually helps the user model the more correct action This is also particularly applicable to walking rehabilitation, etc. where location specific alarms teach both at a conscious and unconscious level precisely where a change, for example in gait, needs to be made over and over again as the user walks.

Extended rehabilitation and simulation features. FIGS. 20-21 illustrate equipment originally documented in the provisional patent application 60/234,191 from which this application came. To understand how it works requires more understanding of how the assistive clothing works than how the additive assemblies of FIGS. 20 and 21 work which rotate the user in all dimensions and provide inertial simulation as well. FIG. 21 provides a side view of a basically horizontal user with arms pointing to the ceiling. The user has been rotated by the pitch control rail (A). Adjustments to roll is accomplished by G. While yaw is perceived more by visual means, which can be any of the display-glasses means, the feeling of turning is provided by the optional turntable E. Inertial response in the horizontal plane is provided by the moving platform F. FIG. 20 illustrated the additive rotational control of a "close-in rotator" for additive and tighter pitch control and reduction of unnecessary centrifugal inertial effects caused by the same accomplished pitch changes on a wider radius.

As already noted, what requires more understanding is how the assistive clothing causes the user to feel and act as if performing acts and doing work in a virtual environment. An unique factor is the synchronously and retention-supported firmly controlled nature of the joint-control point management. Thus, users could in theory (if bones were strong enough, etc.) have their right foot toes clamped into a vise and be held rigidly horizontal with no user effort while simply modeling a vertical standing script (ignoring, of course, balance controls). The point is that the joints are synchronously interdependent in a fashion that not only replicates action but the surrounding environment of those actions. Thus, a user in the assembly of FIG. 21 sitting in a chair script would feel the body's weight on the buttocks, against the back and the weight of the legs on the feet even though the user is actually hanging from the waist without any stress felt on the waist. When in a standing position, the weight would be felt on the feet, not the waist from which the body is actually suspended, because, by replicating the position of the joints to the standing script, the weight is actually being supported by the positionally supported feet. Should the user get on hands and knees, the weight would be felt on the knees and the hands are similarly shaped like the virtual floor against which the user feels the resistance of the actuators reflecting the shape of the floor on the user's hands. The optional ball-joint supported piston of FIG. 20 which replaces the posterior waist control tendon and provides firm back support for those applications (such as the horizontally suspended example shown in FIG. 21) where this takes pressure off the spine which, otherwise, would still support the user as controlled by the waist to upper-torso tendons around the spine, but at substantial stress to the spine. Though hydraulic actuators are illustrated here, FIGS. 20 and 21 illustrate means to rotate the user applicable to any of the assistive clothing assemblies and equipment.

Passive simulation: Touch sensitivity as captured, for example, by the fingertip sensors of FIG. 10 during the action cataloging (which here provides all of the foundation for a full simulation), is, for the user with no nerve damage to the area, replicated not by the array located on the neck as in FIG. 19A but by an array of the same technology (voice coil or other stimulation means) matching the capture array of FIG. 10 in layout (in fact looking much like it) such that the user feels not only the pressure of the fingertip that will not move beyond the virtual floor (in the hands and knees example above) but also details such as a grain of sand on the floor touching the action cataloger's fingertip assembly of FIG. 10. Users with no feeling where touch sensations originate in the action cataloging session (such as the fingertip example above) can learn to associate areas of sensed contact on another area of the body mapped in a logical or recognizable fashion. FIG. 19A illustrates one example where the stimulation matrix is adhered in close contact with the back of the neck to promote true transmission of sound, low-wave vibration and/or other stimulus to the skin area below it. It is laid out in a simple but easily learned fingers-of-the hand shaped matrix allowing the user to learn to recognize when a corresponding (here fairly general) area of a finger makes contact. Much more detail is possible but with complexity comes additional learning time. Thus the user with no feeling, for example in the hands, wearing assistive clothing, can "feel" his hands contacting surfaces (which, with wide ranging frequencies of sound from short shrill to low impact, can be richly qualitative) and the non-handicapped user immersed in a virtual environment can feel virtual objects in both hands (and elsewhere) with those sensations reproduced in the appropriate locations on the hands (parallel mapping).

The addition of visual capture means to record the action cataloger's view when modeling are fairly obvious and also documented in the foundational patent application. However, if the user's head attitude is out of line with respect to the scripted values and body attitudes this would create a false replication because the view would not precisely match the body positions and original positions. Thus the current invention moves the image on the display in the following manner. If, for example, the user display image is 100 degrees of the user's field of view, which reflects 100 degrees of yaw (50 degrees each way from center) and $$Screen RX = Screen X + (Script Y - (Y_C - R_Y)) * (Pixels/DegreeOfYaw)$$

$$Screen RY = Screen Y + (Script P - P_C) * (Pixels/DegreeOfPitch)$$

Where ScreenX and ScreenY are the X and Y locations on the display of a point (pixel) to be displayed on the user visual means using normal geometric nomenclature. The above equations adjust the normal location on the screen in the following manner. When the script is begun, unless something special about the attitudes is important to the function (like being facing due North to see a compass reading, etc.), the scripted yaw normally starts at 0. Since it is rare that the user's actual yaw with respect to due North (or other chosen anchor attitude) also happens to be zero, the relative yaw adjustment value ($R_Y$), which after subtracting the 0 is still equal to the current yaw value, is stored. Thus, when this value is immediately subtracted from the current actual yaw ($Y_C$), whether current yaw is positive or negative, it evaluates to zero (since we haven't moved yet). Thus, $Y_C - R_Y$ is the adjusted relative yaw. If it is different from the scripted yaw (ScriptY), then there is an error thus the first line creates a conversion of ScreenX to a proper relative offset, ScreenRX.

If, for example, the difference inside the parentheses is negative (if the user's head is turned too far to the right), then the image needs to be shifted to the left by that amount. Because any error is in terms of degrees it is then multiplied times the number of pixels per degree of yaw in the current equipement. Thus, the negative difference is added to the original screen X value to create an appropriately left-adjusted value and the screen image shifts to the left (in this example).

The vertical relative adjusted value for geometric Y on the screen, ScreenRY is simpler. The difference between the scripted pitch (ScriptP) and the current actual pitch ($P_C$) is converted to pixels and added to the original pixel vertical location (ScreenY) where the pixel would have otherwise been displayed. It should be noted that normally screen display is relative to a starting point and, where this is the case, only this starting point needs to be recalculated in each timeslice and forwarded to a video card that already handles the offset mapping thus avoiding the overhead of using the above calculations on every single pixel.

Thus, if the user's head moves down and to the left of where the relative scripted head attitude was, the image will move up and to the right from the planned (center) area of video memory stored (Oust as your view of this document does when you move your head down and to the right) accurately reflecting to the user the view according to the user's actual attitude. To avoid "running out of picture" when the user gets too far off track (and thus scrolls away from the center of the image seen by the action cataloger), a wider angle of capture can be stored which is of course mapped to wider video memory so that reasonable turns from recommended norms do not result in some gray space with no data on the left of the display, for example, when the users turn their heads to the left. Wide-angle lens or multiple overlapped cameras on the action cataloger's end provide a wide (and deep) image area subsequently mapped to a larger video memory area and thus a providing a wide range of viewer flexibility to "look around". Where cost or specific-to-the-application engineering constraints cause implementers to simply capture a natural video field of view by the action cataloging process, the user will be able to get off track, the image will move appropriately and naturally and the gray areas in the periphery, optionally highlighted by a colored border will be another user signal of an aberration from the recommended body positions.

Also, where wide periphery imaging is used as above to capture and save peripheral data, a golfing student, for example, could look down from the normal field of view and see the action cataloger's foot placement, club angle and grip on the club. Also, when using an overlaid partial rear-reflectance imaging visual means like those illustrated in FIGS. 13-17 where an image brightness has been chosen to make both the natural, through the lens image, and the partially reflected rear image overlap, the student's own hands, feet, club, etc. will be visible overlaid against that of the action cataloger for easy observation of differences even in the middle of the action. Thus, the rear brightness and/or the reflectance of the reflecting means (such as by variation of the angle or amount of coating) can be modified to take a very new trainee and show the cataloger only as the task is recapitulated in full body response, then the ratio of image brightness is changed to show 2 overlaid images so the user can try to repeat the action with strong overlaid imaging support and, finally, when competent, the user can become comfortable practicing with only the through-the lens visual image simply by changing the through-the-lens to reflected ratio to 1:0.

Thus, a full body replicatable virtual experience can be created without a simulator or virtual environment (or any of the enormous setup times and expenses associated with them) simply by an action cataloger following the normal script capturing process described herein. Then, when a user, either suspended by the equipment of FIGS. 20 and 21 (where that equipment simply replicates the pitch, roll and, optionally, yaw of the recorded attitude sensor readings) or simply wearing the assistive clothing and having that assembly follow the script on the user's body, the user experiences what the action cataloger did—and sometimes even more if they digress from the script.

Applications can include helping a rehabilitating patient learn to walk again (with fall protection either from the basic assistive clothing as the user walks or by being safely suspended by the equipment of FIGS. 20 and 21) or teaching a user to dance with a virtual partner.

Audio means are also easily addable to and synchronizable with the real time reproduction of action using commonly known means. Like the video means, the audio images are stored on disk like the .dbf script files (from which they are called up by notation in the memo field) but in a sound or wave format for ease of reproduction with off the shelf parts. The sound and video are both cued in advance (preferably called individually in the first few records of the script followed by a short delay for loading) to facilitate immediate playing when the script record indicating the beginning of the play time is executed in the script.

User full body immersion in classic virtual reality: Classic virtual applications: Additionally, these scripted body positions, attitude sensor readings, etc. can be replicated in a full virtual environment. One applicable virtual embodiment creates tensors for the limbs (typically hollow), joint-control points on those limbs and virtual tendons acting upon them, etc. to create a virtual body that then reports the very efficient joint-control point data to the assistive clothing. By responding to the joint angle changes reflected in these tensor joint-control points just as it would respond to position changes in a script, the assistive clothing positions the user's body responsive to the virtual environment greatly increasing the experience and applications of the simulation process. Integration of obvious visual and sensory means provide an effective passive simulation means integrates the visual with the actual full-body balance (sensed by a user actually supported in the virtual positions), feeling of impact, sound, etc. that can be used for instructive simulation (teaching a perfect golf swing, etc.) or to help a rehabilitating patient recover by virtually directed and fall-protected walking.

Active classic simulation: Similar to and using elements of the passive simulation just above, the joint-control point data of the assistive clothing worn, for example, by an action cataloger, can also direct parallel changes on the comparable virtual joint-control points. Thus the assistive clothing can be used to direct actions in a virtual environment as well as respond to them. This sets the stage for true full-body, two way virtual interaction where the virtual environment affects the user and the user affects the virtual environment.

As documented in the foundational patent application and described herein, the assistive clothing can also optionally be programmed to provide degrees of resistive pressure in a direction rather than forcing a position in that direction. While, under the right circumstances, this accomplishes the same goal of joint position control, it additionally allows the user to feel a precise amount of weight, resistance to motion, etc. and, optionally, overcome it with user responsive force.

Thus the assistive clothing allows the user to sit on virtual chairs, climb virtual mountains, swing from virtual trees (with the FIG. 21 assembly) and feel the shape and pressure of the tree in hand, etc. This is because, as long as the virtual means sends the forces applied upon virtual tensor positions (understood as or converted into joint-control point values) to the assistive clothing processing means, the assistive clothing will do its part and cause the user to feel those pressures towards the desired positions on joint-control points on the user simply by following the streaming data as a normal script. And, when the assistive clothing processing means reports for each cycle the current joint-control positions to the virtual means, the virtual means applies these forces to the tensors resulting in the proper responsive virtual action to user actions.

Thus, just as the local user in the foundational patent application directed the remote unit through the virtual interface (the computing means between them), the assistive clothing user's equipment (comparable to the "local" in the foundational patent) both responds to and directs the virtual body (directly comparable to the "remote" of the prior patent application).

More applications of the new virtual means: Both simulation means above (1. simple replay of a modeled script with pressure values and 2. an interface between the assistive clothing and a virtual environment) allow the user to feel and sit on non-existent chairs and hold non-existent burdens while feeling the weight of them etc. The simple replay method, for example, of an action cataloger swinging a golf club replays a script which includes the pressure on each joint-control point (using any of the already discussed pressure sensing means). As the cataloger's hand gripped the club, each finger exerted a known amount of pressure in the process of flexion and this pressure value is recorded in the script. Then, when the script is run in passive mode, the user feels the shape of the club in each hand and experiences the "perfect swing" as the positions of the script are forcibly executed.

However, when the same script is run in user-directed mode, the initial positions of the script are forcibly assumed but, from that point, it is the pressures of the script (not the positions) that are replicated allowing the user to diverge from the path in a practice attempt to see if the previous action was learned (if not, the corrective stimulations, etc. above can be effected). These pressures are replicated, in the tendon-based example, by the opposing tendon(s). Thus if the middle hand of FIG. 1 was open with the palm facing upwards and a heavy weight in the hand requires a retraction pressure on the actuator of tendon A of X psi (or, for stepper or other non-hydraulic actuator means a calculated comparable value) to maintain the weight without bending, in replay it is the opposing tendon (C) which will retract with a force of X psi (or calculated equivalent) placing that weight on the user. By recording the values of the user-directed session and replaying those user directed positions in position-effected mode (making the user do it slowly just as it was quickly) with a higher value for timeslice, the user can see and feel in slow motion where the user's action varied from the professional model complete with the warnings and/or stimulations already covered.

Thus, without need of a virtual simulator, a professionally action cataloged golf swing or any action to be learned can first be experienced in perfection complete with the feel, for example, of the golf club shape in hand and the video view that the action cataloger had including the exact position of the club at each point. Then, in user-directed mode, the user feels both the shape and the weight of the club while attempting to swing like the pro towards the still properly placed video golf ball. Aberrations from the perfect swing are responded to by any of the means already covered. Additively or alternatively, the script can include specific points (records) in the script or specific periods (like every 100 timeslices) in which it switches from user-directed (pressure replication) to forcible replay (position replication) noticeably bumping the user back into the proper groove. Scripts and/or programs can also, as already covered, include tolerances allowing an acceptable variance to highlight only significant aberrations.

This is not to say that there are no advantages to the ease of interface to classic virtual reality means.

In fact, using the sports applications example again, in the example of the interface to a tensor or other-based classic virtual reality environment, the user would not only be able to see a pitched baseball coming but when the tensor for the bat overlapped virtual space with the tensor for the ball, the impact can be felt in the full-body reaction of the assistive clothing using the normal means discussed above and the tensor baseball can be seen heading over a virtual fence. There can be substantial advantages to using the assistive clothing for total immersion into a classical virtual environment. However, the ability to create from scratch a completely new virtual session in any environment with no stage or props required in either capture or replication in just the time it takes to put on the equipment and model an action and the ability to immediately reproduce and react to that experience in a full-body, full-visual, full sound, true balance virtual experience is a substantial new advantage as well.

Active training and physical therapy and applications to Physical Therapy: In addition to allowing the disabled to care for themselves and even travel, the same invention allows the user to go through extensive therapeutic routines (without the continuous aid of a physical therapist), exercise unresponsive muscles and improve circulation, retrain spinal and supraspinal based muscle and muscle group controls, protect the training user from falls (even during spasms or seizures), eliminate painful and session-shortening crutch tiring and sores and greatly extend the scope of therapy by reducing the discomfort, exhaustion and expense.

Following action capture sequences as described above, the assistive clothing wearer can be taken through the most complex physical therapy routines with precision. For example, the action cataloguer takes the role of the disabled by wearing the assistive clothing while a qualified therapist takes the action cataloguer through the physical therapy process including nuances of the full body condition including speed of motion and, optionally, pressure. That therapy is reduced to database tables as documented above. Then, even in a relaxed sleep state, the user, wearing the assistive clothing of the current invention can regain lost body mobility and improve circulation. Because the treatment can be spread out over more time (there is no professional standing by who needs to be somewhere else), the mobility advancement per minute can be reduced substantially.

It is well known that games distract the user from the pain of exertion and can increase therapy session length without wearying the patient. Thus, the user wearing the unique body-control and sensing equipment and the visual means described above can, using either of the virtual simulation interfaces described above can play games performing actions that the user is not actually able to do unaided as yet such as walking and even running.

It is also well known that repetitive, rhythmic training such as body weight support walking, helps retrain coordinated muscle activity. However, by improving the repetitive and rhythmic nature of the training with assistive clothing that faithfully repeats the action in an environment where the conditions really are consistent every time as the action is repeated, that learning can be accelerated. Also, by that faithful repetition, the impaired spinal reflex modulation of spinal cord injury patients that contribute to damaging and unstable gaits can be improved. It can be further improved with the coordinated synchronization of the assistive clothing and stimulation means.

Electro-stimulation: Also, existing research has shown that, in patients who have no use of muscles, electronically stimulated muscles can be retracted, sustained and relaxed in a controlled fashion that exercises the muscles and retrains the spinal and supraspinal muscle controls. However, a medium is still needed to allow easy and precise capture of fluid, natural-gait scripts that can then be used with precision assistive means to guide and support the user in a precise but fluid gait that is precisely consistent with the stimulation provided both in terms of time of stimulation with the respect to the precise point in the action and the precision positioning of the limb when the stimulation occurs. Even a slightly abnormal or less than precision controlled gait, stimulation timing or amplitude control can not only result in joint degeneration from the aberrant gait and potential falls but can also cause a rapidly accelerating out-of-synchronization condition by contributing to the gait error with a stimulation intended for a different joint position or even a very slightly different point in time. In bipedal walking which requires an already out-of-balance condition unfriendly to a push when a pull is demanded, this is a recipe for problems that require unproductive corrective controls that can add to user exhaustion.

The assistive clothing of the current invention provides the precision recapitulated gait in a scripted medium and provides synchronized precision application of electronic, pharmacological and other nerve, spinal, supraspinal and/or muscle stimuli at the precise point in time and position and with power applicable to tiny timeslices in the stroke for additional precision. While protected by the fall-control means and supported as needed by the assistive clothing apparatus, the muscles themselves can thus be caused to provide some or all of the support and locomotion means.

For example, in a simple, repeating script of a normalized 2-step cyclical gait, as the processing means is cyclically processing the data records of those positions over time it can also process records in the same table sorted identically by sequence and thus time and direct the stimulation means. Although the current invention places no restrictions on how this stimulation data must be arranged, a sample format is illustrated below using special records in the normal Positions.dbf table. By simply inserting records in the sequence of events stored in Positions.dbf, these records, when encountered by the program scanning these records simply passes the information to the stimulation means or, for broader compatibility and more safety, programmatically creates commands that are already compatible with existing stimulation systems thus assuring the synchronization of the stimulation to the gait and yet being in control of such stimulation for safety. That is because, for safety reasons, when suspicious of a "tilt" (impending fall) condition, a trip (for example, in a walking sequence), a spasm (sensed from out-of-norm-for-that-point-in-the-gait pressure levels sensed on joints) or other unsafe condition, the assistive clothing processor reserves the programmatic option to override (discontinue temporarily) these muscle stimulations and/or reinsert an alternative set of those stimulations to match a recovery script. For example, in a "tilt" condition (where the overall attitude of the user varies significantly from the recorded body attitude of the modeler or where the attitude simply exceeds limits defined for the sequence itself), the processing means will typically morph to a recovery script appropriate for the action which will either have not stimulation cues to stimulation means or a special set supportive of the recovery script.

Positions.dbf:

| ActionCode | JointNum | SeqNumber | NewPosition | Pressure | Misc |
|---|---|---|---|---|---|
| 171 | 0177 | 71 | 257000 | 00000200 | #(>1 |

Example of one stimulation record format. Here, simply for debugging and ease of script and software maintenance, the JointNum=0177 actually does refer to a specific joint that is connected or related to the muscle or group to be stimulated. Otherwise, it can be ignored as the routine sequence unfolds. ActionCode and SeqNum are also playing their normal role. However, important stimulation data is contained in other fields. The first 4 characters of NewPosition identifies a specific target stimulation area. The first 2 characters of Misc are duration of stimulation (convertible to decimal ASCII thus rendering over 65,000 possible ticks of duration. All the remaining fields (including JointNum which is non-critical here) can be used to store other stimulation specific data (such as charge amplitude, HZ, etc.) which can either be passed to stimulation means or programmatically converted to existing input formats for the stimulation means and ported to it.

The duration of the stimulation is optional since the many time slices could be used to provide very short stimulations concatenated over time. However, for economy of data storage and simplicity of scripting, the duration variable may be included telling whatever existing or future stimulation mechanism how long to continue the exact same amount of stimulation either by direct porting of duration or the creation of time-spaced, stimulation-means compatible input commands.

Also, the same invention can provide a "safety net" allowing the user freedom to provide his own power (or some of it) while using balance controls, including both balance recovery programming based on default norms for a function and adherence to scripted attitudes and accelerations for continuous balance control and context specific recovery scripts for conditions further out of the desired range to assure that he doesn't fall. This independence with safety, in addition to the improvement in patient spirit, can greatly extend the amount of care the individual receives. By receiving care whenever the patient wants it and for as long as the patient wants it, more training time is available to the user. However, that would be useless if the process were too tiring or damaging for the patient to put in those hours. Fortunately, the process replaces the need for typical "crutch therapy" that strengthens the wrong set of muscles (arms), wears out the user, wears sores in the armpits and teaches an unnatural gait that can be damaging. The assistive clothing supports the user, allows the user to direct its support as it teaches a perfect gait and replaces the "crutch therapy" with assisted walking that exercises the muscles the patient will be needing.

But that is not what is claimed.

What is claimed is:

1. A user interface comprising:
   a sensor located in the mouth sensitive to at least the locations of its contact with the tongue;
   a device to receive data;
   a power provision component for providing power to in-mouth components; and
   a processing facility, operatively connected to said sensor and to said device to receive data, for at least calculating, from the plurality of essentially simultaneously sensed points of tongue contact with said sensor, a single value representative of the approximate location of the tongue on the surface of the sensor and for providing at least data relative to said value to said device to receive data thus enabling a user to at least communicate a desired movement along a path related to the path of the tongue over the sensor's surface.

2. The user interface of claim 1 wherein said processing facility recognizes initiation and termination of tongue contacts as event input analogous to the clicks and releases of mouse buttons enabling operations equivalent to those performed with computer mice.

3. The user interface of claim 1 wherein said processing facility, in addition to said position, recognizes initiation and termination of tongue contacts as event input for directing said device to receive data analogously as a computer touchpad.

4. The user interface of claim 1 wherein
said processing facility creates the data provided to said device to receive data in a form already properly formatted to direct said device to receive data;
whereby a plug-and-play compatibility may be enabled allowing the replacement of a computer pointing device with a hands-free alternative.

5. The user interface of claim 1 wherein the processing facility is located in the mouth.

6. The user interface of claim 1 wherein the processing facility tasks are a selected one of the group comprising a) located outside the mouth and b) shared by processing facilities in the mouth and processing facilities outside the mouth.

7. The user interface of claim 1 wherein a magnitude of area of tongue contact on said sensor may be recognized as a magnitude; whereby, an additional source of input data is provided.

8. The user interface of claim 1 further comprising:
buttons for use as data entry keys.

9. A user interface comprising:
a sensor located in the mouth whose surface is sensitive to at least the locations of its contact with the tongue;
a device to be controlled;
a power provision component for providing power to components; and
a processing facility operatively connected to said sensor and to said device to be controlled for generating, from said sensor's output, at least directional data responsive to the path of the tongue's movement on the surface of said sensor and, by at least providing said data to said device to be controlled, directing said device to be controlled analogously as a computer touchpad.

10. A user input device comprising:
a sensor located in the mouth sensitive to locations of tongue contact;
a processing component, operatively connected to said sensor and to a device to receive data, for at least identifying from sensor data the approximate location of the tongue on the sensor and communicating, to said device to receive data, at least data that can be used to provide guidance relative to the speed with which the tongue moved on the sensor and the direction of that movement.

11. A user input device comprising:
a sensor in the mouth for sensing at least the approximate location of the tongue on the sensor;
a securing facility for securing the position of in-mouth components;
a device to be directed;

a processing facility, operatively connected to said sensor and having an operative connection with said device to be directed, for calculating and providing to said device to be controlled data responsive to tongue contact and the directions of tongue movement over said sensor based on said sensor's data; whereby devices are provided the kind of data provided by computer touchpads but without requiring the use of hands.

12. The user input device of claim 11 wherein the data provided to said device to be controlled is formatted by processing facility to match the preferred data format of said device to be controlled; whereby an existing interface can be more easily replaced with this hands-free one.

13. A user interface comprising:
a sensor located in the mouth for sensing at least the location of the tongue on the sensor
a securing device for securing the user interface's in-mouth components;
a power provision component for providing power to in-mouth components;
a processing component, operatively connected to said sensor and to a device to be controlled, for at least identifying, from the portion of the sensor in contact with the tongue, a point representative of the approximate location of the tongue on the sensor and communicating, to said device to be controlled, at least data relatable to a distance and direction relative to the distance the tongue moves on the sensor and the direction of that movement; whereby devices can be directed without need of hands and said user interface can be used to replace mice and pointing devices.

14. A user interface comprising:
a sensor located in the mouth for sensing at least the location of the tongue;
a securing device for securing the user interface's in-mouth components;
a processing component, operatively connected to said sensor and to a device to receive data, for at least calculating, from the portion of the sensor in contact with the tongue,
a reference point responsive to the approximate location of the tongue on the sensor and communicating, to said device to receive data, at least positional data responsive to the relative position of the tongue on the sensor; whereby
said positional data contains data indicative of a selected one of the group comprising a) a point in an area, b) a point on a line and c) both a and b, allowing the hands-free device to be used to replace conventional mice, touchpads, sliders and pointing devices.

15. A user interface comprising:
a plurality of sensors, which may be a plurality of sensitive locations on a single component, located in the mouth sensitive to at least the presence of tongue contact and arrayed in essentially a row and column pattern;
a securing component for securing said plurality of sensors in the mouth;
a device to be controlled;
a processing facility, operatively connected to said plurality of sensors and to said device to be controlled, for determining at least a representative location in an area spatially comparable to at least the approximate location of at least one said sensor incurring tongue contact and providing, to said device to use data, data, including data responsive to said representative location, in order to direct said device to be controlled analogously as a computer touchpad.

16. A user interface comprising:
a sensor assembly located in the mouth having locations of sensitivity to tongue contact whose known spatial arrangement enables the capture of at least relative location data based on where the tongue contacts the sensor assembly;
a power provision component for providing power to in-mouth components;
at least one device to receive data; and
a processing facility, operatively connected to said sensor assembly and to said at least one device to receive data, for at least providing, to said at least one device to receive data, data responsive to said relative location data; whereby
devices are provided the kind of data provided by computer touchpads but without requiring the use of hands.

17. A user interface comprising:
a sensor located in the mouth for sensing at least the locations of its contact with the tongue;
a power provision component for providing power to components;
a device to receive data; and
a processing facility, operatively connected to said sensor and to said device to receive data, for identifying at least, from the plurality of points of potentially simultaneous tongue contact on said sensor, a single relative spatial location based upon the approximate location of the tongue on the sensor and for providing, to said device to receive data, data including said relative spatial location.

18. A user interface comprising:
a touchpad sensor located in the mouth for sensing at least the locations of tongue contact with said touchpad sensor,
a power provision component for providing power to components as needed;
a device to receive data;
a processing facility, operatively connected to said touchpad sensor and to said device to receive data, for identifying at least a representative value for an approximation of where on the touchpad sensor contact is made, and for providing to said device to receive data, data including data based on said representative value, and directing said device to receive data analogously as a computer touchpad.

19. A user interface comprising:
a sensor assembly located in the mouth sensitive to at least the locations of tongue contact; and
a securing element for securing said sensor assembly and other in-mouth components; and
a sending component for sending data;
a receiving component for receiving data from said sending component;
a device to receive data operatively connected to said receiving component;
at least one power provision facility for providing power to components;
a first processing component for receiving data from said sensor assembly, for identifying from said received data at least a single value indicative of the approximate location of the tongue on said sensor assembly, and for sending processed data that is at least indicative of said approximate location to said device to receive data via the sending element.

20. The user interface of claim 19 further comprising:
a second processing component for sharing the processing load wherein part of the processing otherwise performed by said first processing component may be performed by said second processing component with said second processing component being operatively connected to both said receiving component and said device to receive data.

21. A user interface comprising:
a sensor assembly with a plurality of sensitive locations located in the mouth sensitive to at least the locations of tongue contact with said sensor assembly;
a device to be controlled; and
a processing facility, operatively connected to said sensor assembly and to said device to be controlled, for processing signals from said sensor assembly into at least data indicative of a position relative to the portion of said sensor assembly that is in contact with the tongue and providing data, based upon said position, to said device to be controlled for the direction of said device to be controlled analogously as a computer touchpad.

22. The user interface of claim 21 wherein a value indicative of at least the approximate size of said portion of said sensor assembly that is in contact with the tongue is conveyed to said device to be controlled for the provision, to said device to be controlled, of not only the location-related information that computer touchpads and mice provide but also data that is useful as an additional communicated value.

23. A user interface comprising:
a plurality of sensors located in the mouth sensitive to contact with the tongue;
a housing for securing in-mouth user interface components;
a device to receive data;
a power facility for providing power to user interface components;
a processing facility, operatively connected to said plurality of sensors and to a device to receive data, for calculating, from the output of said plurality of sensors, at least data related to the area of tongue contact on said plurality of sensors and for providing data, including said data related to the area of tongue contact, to said device to receive data.

24. The user interface of claim 23 wherein said processing facility calculates a value representative of at least the approximate location of the tongue on said plurality of sensors, said value being analogous to the locational data captured by computer touchpads, and directs said device to receive data analogously as a computer touchpad.

25. A user interface comprising:
a plurality of sensors located in the mouth sensitive to contact with the tongue;
a housing for securing in-mouth user interface components;
a device to be controlled; and
a processing facility, operatively connected to said plurality of sensors and to said device to be controlled, for generating and providing to said device to be controlled instructions for said device to be controlled that are already in a format accepted by said device to be controlled with said instructions based on positional data drawn from the at least approximate location of portions of the area populated by the said plurality of sensors that are in contact with the tongue; whereby
a device to be controlled can be directed with actions of the tongue and without necessary additional data conversion.

26. A user interface comprising:
a sensor located in the mouth sensitive to at least location of tongue contact on the sensor;

a power facility for providing power to user interface components;

a device to receive data; and a processing facility, operatively connected to said sensor and to a device to receive data, for calculating, from the output of said sensor, a value relative to the distance from at least an approximate location for the tongue on said sensor to at least one reference point on said sensor's sensitive area and delivering at least data based on said value to said device to receive data enabling a user to at least communicate a spatial reference to said device to receive data based upon contact with the tongue on a user-chosen point on the sensor.

27. The user interface of claim 26 wherein a user can select a point in one dimension by touching the tongue to a point between two sides of said sensor's sensitive area.

28. The user interface of claim 27 wherein a user can select a point in two dimensions by touching the tongue to a point with a chosen distance between the two-dimensional boundaries of said sensor's sensitive area.

29. The user interface of claim 27 wherein said processing facility recognizes initiation and termination of contacts between tongue and said sensor as event data and, using said event data and data associated with said value, directs said device to receive data analogously as a computer touchpad.

30. The user interface of claim 27 wherein said processing facility recognizes initiation and termination of contacts between tongue and said sensor as event data and, using said event data and data associated with said value, directs said device to receive data analogously as a computer mouse.

31. A user interface comprising:
a sensor located in the mouth of a user for sensing at least the locations of its contact with the tongue;
a housing in the mouth for securing in-mouth components,
a worn video display;
a device to receive data; and
a processing facility, operatively connected to said sensor and operatively connected to said worn video display, for at least recognizing user directional instructions communicated by at least the path of tongue movement over said sensor and for controlling image display on said worn video display responsive to said instructions.

32. The user interface of claim 31 wherein said processing facility interprets initiation and termination of contact between the tongue and said sensor as events analogous to computer touchpad tap and drag commands and directs said worn display analogously as a computer touchpad responding to screen-displayed options.

33. A user interface comprising:
a sensor located in the mouth sensitive to the locations of its contact with the tongue;
a securing facility for securing in-mouth components;
a device to receive data; and
a processing facility, operatively connected to said sensor and to a device to receive data, for calculating, from the plurality of essentially simultaneously sensed points of tongue contact with said sensor, a single positional value representative of the approximate location of the tongue on the surface of the sensor adjusted to offset at least the results of non-planarities in the shape of the sensor array by at least linearizing readings responsive to curved paths on the known shape, and for providing data responsive to said positional value to the device to receive data; whereby a user can control a device with actions of the tongue on a sensor that is not perfectly shaped approximately as if it was because the processing facility has adjusted the data.

34. A user interface comprising:
a plurality of sensors located in the mouth, which may be a plurality of sensitive locations on a single component, sensitive to the location of the tongue; and
a head-position sensor for measuring the current position of the head;
a device to be controlled; and
a processing facility, operatively connected to said plurality of sensors, said head-position sensor, and said device to be controlled, for calculating, from the plurality of essentially simultaneously sensed points of tongue contact with said sensor, a single positional value representative of the approximate location of the tongue on the surface of the sensor and for recognizing, from the head-position, spatial instructions associated with head-positions, and for communicating data responsive to both head-position and said positional value to direct said device to be controlled.

35. A user interface for controlling a body comprising:
a sensor located in the mouth sensitive to the locations of its contact with the tongue;
at least one body-controlling component, responsive to electronic direction, for controlling the activity of at least one body part;
a processing facility, operatively connected to said sensor and to said body-controlling component, for calculating, from the plurality of essentially simultaneously sensed points of tongue contact with said sensor, a single positional value representative of the approximate location of the tongue on the surface of the sensor and creating and sending commands based on said positional value to said at least one body-controlling component to direct said at least one body part.

36. A user interface comprising:
a sensor located in the mouth sensitive to the locations of contact with the tongue;
at least one component to be directed;
a processing facility, operatively connected to said sensor and to said at least one component to be directed, for generating a value, based upon where the tongue is touching said sensor, and for directing said at least one component to be directed to follow a set of steps, and for modifying the execution of said set of steps responsive to said value thus allowing the user to change the execution in essentially real time; whereby
a potentially extremely complex set of steps can be accomplished with less required attention by the user since the user may only need to make adjustments to steps being executed.

37. A user interface comprising:
at least one sensor located in the mouth sensitive to contact with the tongue;
an eye tracking component for identifying at least one value responsive to where the user is looking;
a device to directed; and
a processing facility, operatively connected to said at least one sensor, to said eye tracking component and to said device to be directed, for, in response to a tongue contact, at least directing said device to be directed to perform an action and determining what that action should be based on at least a known meaning for said at least one value at the time of said tongue contact; whereby said processing facilities can determine what actions to direct based specifically upon the user's eye-fixation-identified context at the time of said tongue contact.

38. A method for controlling a device comprising the steps of:

1. placing in the mouth a housing which contains a sensor sensitive to locations of its contact with the tongue
2. contacting said sensor with the tongue at a user-desired location and, where applicable, moving it,
3. processing data from said sensor to identify, from the plurality of points on said sensor that are in contact with the tongue, a single reference location value indicative of where the tongue is contacting said sensor,
4. communicating control signals, that are responsive to at least said single reference location value, to a device to be controlled
5. responding, at said device to be controlled, with the action indicated by said single reference location.

* * * * *